US012797571B2

(12) United States Patent
Lau et al.

(10) Patent No.: US 12,797,571 B2
(45) Date of Patent: *Nov. 17, 2026

(54) CONNECTORS FOR CONDUITS

(71) Applicant: Fisher & Paykel Healthcare Limited, Auckland (NZ)

(72) Inventors: Andrew Chi Lup Lau, Auckland (NZ); Richard Daniel Panara, Auckland (NZ); Laurence Gulliver, Auckland (NZ); Sooji Hope Clarkson, Auckland (NZ); Jason Allan Klenner, Auckland (NZ); Andrew Paul Maxwell Salmon, Auckland (NZ); Brent Ian Laing, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/399,898

(22) Filed: Aug. 11, 2021

(65) Prior Publication Data

US 2021/0402126 A1 Dec. 30, 2021

Related U.S. Application Data

(63) Continuation of application No. 15/756,953, filed as application No. PCT/IB2016/055258 on Sep. 2, 2016.

(Continued)

(51) Int. Cl.

*A61M 16/08* (2006.01)
*A61M 16/10* (2006.01)

(Continued)

(52) U.S. Cl.

CPC .... *A61M 16/0816* (2013.01); *A61M 16/0825* (2014.02); *A61M 16/0875* (2013.01);

(Continued)

(58) Field of Classification Search

CPC .............. A61M 16/08; A61M 16/0816; A61M 16/0825; A61M 16/0875; A61M 16/10;

(Continued)

(56) References Cited

U.S. PATENT DOCUMENTS

| | | | |
|---|---|---|---|
| 132,604 | A | 10/1872 | Smith et al. |
| 327,877 | A | 10/1885 | Hodges |

(Continued)

FOREIGN PATENT DOCUMENTS

| | | | |
|---|---|---|---|
| CN | 2652420 | Y | 11/2004 |
| CN | 1628870 | | 6/2005 |

(Continued)

OTHER PUBLICATIONS

Fisher & Paykel Healthcare Limited, Junior Tube and Chamber Kit brochure, 900PT531, 2012, 4 pp.

(Continued)

*Primary Examiner* — Victoria Murphy
*Assistant Examiner* — Sara K Toich
(74) *Attorney, Agent, or Firm* — VIA LLP

(57) ABSTRACT

This invention relates to connectors to be provided into fluid communication or engagement either directly with, or via a component to be associated with, a terminal end of a breathing conduit. In at least one embodiment, the connector comprises a body having a first end and a second end, and an internal lumen for the passage of gas between the ends. The first end engageable with a terminal end of a conduit or a component to be associated therewith. The second end engageable with another connector. An internal surface of the body at the second end comprises internal connection features for connection with another connector to be received internally therein. An external surface of the body comprises one or more external alignment feature(s) for (Continued)

aligning the connector or another connection into an aligned orientation for connection therebetween.

35 Claims, 35 Drawing Sheets

Related U.S. Application Data

(60) Provisional application No. 62/347,965, filed on Jun. 9, 2016, provisional application No. 62/214,643, filed on Sep. 4, 2015.

(51) Int. Cl.
*A61M 16/16* (2006.01)
*F16L 37/248* (2006.01)

(52) U.S. Cl.
CPC ...... *A61M 16/1095* (2014.02); *A61M 16/161* (2014.02); *A61M 2205/3368* (2013.01); *A61M 2205/584* (2013.01); *F16L 37/248* (2013.01)

(58) Field of Classification Search
CPC .............. A61M 16/1095; A61M 16/16; A61M 16/161; A61M 39/10; A61M 2039/1027; A61M 15/002; A61M 15/006; A61M 11/001; A61M 16/01; A61M 16/18; A61M 16/109; A61J 1/1481; A61J 1/1487; A61J 1/2048; A61J 1/2058; A61J 1/2065; A24F 40/40; A24F 40/42; A24F 40/44; A24F 40/46; A24F 40/48; F16L 37/248; F16L 37/252
See application file for complete search history.

(56) References Cited

U.S. PATENT DOCUMENTS 643,358 A 2/1900 Konold
778,936 A 1/1905 Witmond
1,080,674 A 12/1913 Berg
1,130,726 A 3/1915 Greve
1,194,793 A 8/1916 Styers
1,673,338 A 6/1928 Mitchell
1,880,098 A 9/1932 Mair
1,916,449 A 7/1933 Tompkins
2,124,474 A 7/1938 Scholtes
2,479,580 A 8/1949 Marco
2,727,759 A 12/1955 Elliott
2,910,308 A 10/1959 Carr
3,092,409 A 6/1963 Murray
3,287,031 A 11/1966 Simmons et al.
3,323,774 A 6/1967 Wilson
3,513,844 A 5/1970 Smith
3,601,361 A 8/1971 Hundhausen et al.
3,813,115 A 5/1974 French
3,815,754 A 6/1974 Rosenberg
3,870,238 A 3/1975 Sellars
3,932,153 A 1/1976 Byrns
4,036,616 A 7/1977 Byrs
4,111,514 A 9/1978 Brishka et al.
4,128,407 A 12/1978 Chapel
4,161,949 A * 7/1979 Thanawalla .......... A61J 1/2089 604/905
4,211,439 A * 7/1980 Moldestad ............ F16L 37/113 285/376
D267,199 S 12/1982 Koenig
4,386,948 A 6/1983 Choksi
4,443,028 A 4/1984 Hayes
4,446,869 A 5/1984 Knodle
4,584,997 A 4/1986 Delong
4,589,684 A 5/1986 Nowacki et al.
4,601,495 A 7/1986 Webb
4,601,497 A 7/1986 Bartholomew
4,661,110 A 4/1987 Fortier et al.
4,676,241 A 6/1987 Webb et al.
4,758,023 A 7/1988 Vermillion
4,773,448 A 9/1988 Francis
D300,271 S 3/1989 Rudolph et al.
D300,272 S 3/1989 Rudolph et al.
D302,040 S 7/1989 Lambert et al.
4,936,841 A * 6/1990 Aoki .................... A61J 1/2089 604/82
5,005,571 A 4/1991 Dietz
5,009,252 A 4/1991 Faughn
5,040,527 A 8/1991 Larson et al.
5,064,226 A 11/1991 Klas
D328,033 S 7/1992 DiGuiseppi
5,158,569 A 10/1992 Strickland et al.
5,169,180 A 12/1992 Villani et al.
5,230,727 A 7/1993 Pound
5,281,206 A 1/1994 Lopez
5,335,656 A 8/1994 Bowe et al.
5,378,025 A * 1/1995 Szabo ................ F16L 37/0982 285/39
D362,718 S 9/1995 Deily et al.
D363,541 S 10/1995 Cottone, Sr. et al.
5,456,676 A 10/1995 Nelson et al.
5,460,172 A 10/1995 Eckerbom
5,529,284 A 6/1996 Berger et al.
5,584,997 A 12/1996 Yagihashi et al.
5,620,427 A 4/1997 Werschmidt et al.
5,718,143 A 2/1998 Clowes
5,725,258 A 3/1998 Kujawski
5,725,511 A 3/1998 Urrutia
5,735,271 A 4/1998 Lorenzen et al.
5,738,142 A 4/1998 Eike et al.
5,738,143 A * 4/1998 Faughn ................ F16L 37/113 137/614.03
5,741,084 A 4/1998 Del Rio et al.
D395,502 S 6/1998 Deily et al.
5,901,705 A 5/1999 Leagre
D424,687 S 5/2000 Hoenig et al.
D427,308 S 6/2000 Zinger
6,099,519 A 8/2000 Olsen
D431,634 S 10/2000 Mantz
D439,326 S 3/2001 Hecker et al.
D443,863 S 6/2001 Maccarone
D449,107 S 10/2001 Madsen
6,402,207 B1 6/2002 Segal et al.
6,439,234 B1 8/2002 Curti et al.
6,484,724 B1 11/2002 Sloan
D466,607 S 12/2002 Cise
D468,015 S 12/2002 Horppu
D471,262 S 3/2003 Kozu
D472,316 S 3/2003 Douglas et al.
D472,630 S 4/2003 Douglas et al.
6,561,549 B1 5/2003 Moris et al.
D476,232 S 6/2003 Maus et al.
6,581,974 B1 6/2003 Ragner et al.
6,803,496 B2 10/2004 Elder et al.
6,893,055 B2 5/2005 Thomas et al.
6,915,705 B1 7/2005 Truitt
6,932,390 B1 8/2005 Gretz
6,953,354 B2 10/2005 Edirisuriya
7,007,694 B2 3/2006 Aylsworth et al.
D522,109 S 5/2006 White
D522,360 S 6/2006 Caserta
7,201,167 B2 4/2007 Fink et al.
D543,620 S 5/2007 Chu et al.
D547,657 S 7/2007 Tacchella
D551,340 S 9/2007 Wood et al.
7,263,994 B2 9/2007 Gradon et al.
7,267,121 B2 9/2007 Ivri
D553,005 S 10/2007 Py
7,290,541 B2 11/2007 Ivri et al.
D556,899 S 12/2007 Veliss et al.
D557,414 S 12/2007 Wentling
7,306,121 B2 12/2007 Ophardt
7,311,752 B2 12/2007 Tepper
D565,731 S 4/2008 Eisenkolb et al.
D570,457 S 6/2008 Brown
7,406,966 B2 8/2008 Wondka
7,458,615 B2 12/2008 White et al.

(56) References Cited

U.S. PATENT DOCUMENTS

D586,907 S 2/2009 Judson
D586,911 S 2/2009 McAuley et al.
7,484,769 B2 2/2009 Domash et al.
D600,343 S 9/2009 Degabriele et al.
D606,494 S 12/2009 Holliday
D609,091 S 2/2010 Dubach
D612,481 S 3/2010 Reid et al.
7,785,300 B2 8/2010 Ishii et al.
D627,059 S 11/2010 Wood et al.
D628,288 S 11/2010 Row
D629,891 S 12/2010 Virr
D630,732 S 1/2011 Lev et al.
D631,452 S 1/2011 DeGross et al.
D631,542 S 1/2011 DeGross
7,874,596 B2 * 1/2011 Kertesz ............... F16L 37/0985
285/383
D637,713 S 5/2011 Nord et al.
7,946,291 B2 5/2011 Fink et al.
D645,547 S 9/2011 Lombardi et al.
8,020,551 B2 9/2011 Virr et al.
8,092,409 B2 * 1/2012 Mros ...................... A61H 1/008
601/151
D654,573 S 2/2012 Lombardi et al.
D656,231 S 3/2012 Henry et al.
8,186,352 B2 5/2012 Gunaratnam et al.
D661,785 S 6/2012 Johnson
8,256,459 B2 9/2012 Tesluk et al.
8,257,286 B2 * 9/2012 Meyer ................... F16B 7/0413
601/148
8,287,517 B2 10/2012 Hanlon et al.
8,317,203 B2 11/2012 Hermle et al.
D672,037 S 12/2012 Miller
8,376,412 B2 2/2013 Johnson
D677,789 S 3/2013 Row
8,397,727 B2 3/2013 Ng et al.
D682,415 S 5/2013 Mogensen et al.
8,439,039 B2 5/2013 Gunaratnam et al.
D685,463 S 7/2013 Veliss et al.
8,485,193 B2 7/2013 Worley
8,534,278 B2 9/2013 Colman et al.
D691,712 S 10/2013 Judson et al.
D691,717 S 10/2013 McLean et al.
D692,555 S 10/2013 Maksym et al.
D695,890 S 12/2013 Bowden et al.
D697,200 S 1/2014 Mahaffy
D698,440 S 1/2014 Lombardi, III
8,622,057 B2 1/2014 Ujhazy et al.
8,684,979 B2 4/2014 Deighan
D707,355 S 6/2014 Bow
8,741,220 B2 6/2014 O'Donnell et al.
D709,996 S 7/2014 Yu
8,770,190 B2 * 7/2014 Doherty ................... A62B 9/04
128/200.24
D710,695 S 8/2014 Pritikin
8,814,849 B1 8/2014 Winsor
8,870,238 B2 10/2014 Robert et al.
D717,942 S 11/2014 Neff et al.
D719,650 S 12/2014 Arinobe
8,960,727 B2 2/2015 Kendrick
D724,720 S 3/2015 O'Connor et al.
8,967,144 B2 3/2015 Lurie
D726,287 S 4/2015 Steele
D727,492 S 4/2015 Scampoli
9,010,330 B2 4/2015 Barlow et al.
D732,664 S 6/2015 Woehr
D735,038 S 7/2015 Tamarindo
D735,326 S 7/2015 Gulliver
D736,906 S 8/2015 Schultz
D736,914 S 8/2015 Schultz
D737,953 S 9/2015 Wells
D737,963 S 9/2015 Srinivasan et al.
9,132,252 B2 9/2015 Barlow et al.
9,188,267 B2 11/2015 Fansler et al.
D746,416 S 12/2015 Bariar
D747,471 S 1/2016 Gulliver et al.
D747,794 S 1/2016 Greenberg et al.
D750,239 S 2/2016 Pappalardo
9,259,535 B2 2/2016 Anderson
D751,687 S 3/2016 Daly
D757,259 S 5/2016 Duck
D757,933 S 5/2016 Lev et al.
D759,486 S 6/2016 Ingram
9,385,257 B2 7/2016 Aono et al.
D762,843 S 8/2016 Formica
D764,049 S 8/2016 Cullen et al.
9,440,040 B2 9/2016 Klasek et al.
D768,285 S 10/2016 Reed
D771,247 S 11/2016 Shinohara et al.
9,480,809 B2 11/2016 Guney et al.
D777,317 S 1/2017 Soual et al.
D777,324 S 1/2017 Nguyen
D781,417 S 3/2017 Ingram
D784,525 S 4/2017 Nguyen
D785,161 S 4/2017 Dravitzki et al.
D785,789 S 5/2017 Turturro et al.
D787,053 S 5/2017 Huang et al.
D787,054 S 5/2017 Rini et al.
D787,661 S 5/2017 Edwards et al.
D790,054 S 6/2017 Prentice et al.
9,669,181 B2 6/2017 Miller et al.
9,675,774 B2 6/2017 Cipollone
D791,310 S 7/2017 Maurice
D791,938 S 7/2017 Becker
D791,939 S 7/2017 Turturro et al.
D792,584 S 7/2017 Ingram et al.
D792,586 S 7/2017 Becker
D794,184 S 8/2017 Smith et al.
D794,781 S 8/2017 Gilbert et al.
D800,895 S 10/2017 Prentice
D804,023 S 11/2017 Huang et al.
9,808,612 B2 11/2017 Gulliver et al.
D804,661 S 12/2017 Shoji et al.
D805,629 S 12/2017 Fiorenza
D805,630 S 12/2017 Formica
D807,995 S 1/2018 Maeckelberghe et al.
D808,516 S 1/2018 Edwards
9,868,001 B2 1/2018 Walker et al.
9,879,807 B2 1/2018 Brugger et al.
D809,656 S 2/2018 Lau et al.
9,884,176 B2 2/2018 Fangrow
D816,216 S 4/2018 Gulliver et al.
D825,749 S 8/2018 Huang et al.
D827,125 S 8/2018 Nilsson
D827,126 S 8/2018 Nilsson et al.
D832,431 S 10/2018 Turturro
D834,533 S 11/2018 Maroney
D834,712 S 11/2018 Gulliver et al.
D835,260 S 12/2018 Lisberg
D837,743 S 1/2019 Maroney
D841,147 S 2/2019 McCool et al.
D841,148 S 2/2019 Stoks et al.
D847,326 S 4/2019 Eury
10,245,407 B2 4/2019 Osborne
10,265,492 B2 4/2019 Amarasinghe et al.
D847,752 S 5/2019 Barrefelt
D849,232 S 5/2019 Formica
D849,242 S 5/2019 Wilson
D849,931 S 5/2019 Prentice
D852,356 S 6/2019 Steele et al.
10,322,254 B2 6/2019 Fong et al.
D852,949 S 7/2019 Klenner et al.
10,335,583 B2 7/2019 Gulliver et al.
D855,794 S 8/2019 Gray
D856,510 S 8/2019 Scheirlinck
D857,880 S 8/2019 Lau et al.
D860,445 S 9/2019 Ho
D861,162 S 9/2019 Gulliver et al.
D863,545 S 10/2019 Dantanarayana
10,449,320 B2 10/2019 Miller
D867,583 S 11/2019 Yang et al.
D867,586 S 11/2019 Kemps
D867,587 S 11/2019 Holtz et al.
D870,878 S 12/2019 Wilson
D875,242 S 2/2020 Gordon

(56) References Cited

U.S. PATENT DOCUMENTS

D876,617 S 2/2020 Scheirlinck et al.
D878,546 S 3/2020 Formica et al.
D878,549 S 3/2020 Wilson
D879,953 S 3/2020 Ljunglof et al.
D879,956 S 3/2020 Klenner
10,576,233 B2 3/2020 Harwood
D880,686 S 4/2020 Stoks et al.
D887,577 S 6/2020 Shor et al.
D893,016 S 8/2020 Wilson
D893,024 S 8/2020 Whiteside
D894,376 S 8/2020 Boyes
D895,103 S 9/2020 Dantanarayana
D896,758 S 9/2020 Watkins
D896,929 S 9/2020 Vranish
10,786,663 B2 9/2020 Lauer
D899,590 S 10/2020 Gulliver et al.
10,792,486 B2 10/2020 Nelson
D901,673 S 11/2020 Gordon
D903,121 S 11/2020 Chan
10,835,733 B1 11/2020 Gulliver et al.
D909,564 S 2/2021 Bogan
D910,840 S 2/2021 Klenner et al.
D917,690 S 4/2021 Lau et al.
D923,169 S 6/2021 McCool et al.
D923,768 S 6/2021 Maeckelberghe et al.
D924,154 S 7/2021 Dykas et al.
D924,377 S 7/2021 Kwak et al.
D925,734 S 7/2021 Park
11,052,236 B2 7/2021 Gulliver et al.
D928,925 S 8/2021 Lei
D928,948 S 8/2021 Gulliver et al.
D928,949 S 8/2021 Gulliver et al.
D930,184 S 9/2021 Johnson
D933,815 S 10/2021 Eves et al.
D938,016 S 12/2021 Eves et al.
D940,861 S 1/2022 Mosen et al.
11,224,728 B2 1/2022 Ignon
D944,936 S 3/2022 Chaves et al.
D944,939 S 3/2022 Chaves
D947,133 S 3/2022 Byrne
D948,027 S 4/2022 Babbage et al.
D949,294 S 4/2022 Chandler
D949,295 S 4/2022 Chaves
D958,968 S 7/2022 Hobbs
D968,587 S 11/2022 Holyoake
D970,721 S 11/2022 Ros Fabrega et al.
11,504,099 B1 11/2022 Smith et al.
D973,862 S 12/2022 How
D973,887 S 12/2022 Rohde, II et al.
D974,551 S 1/2023 Mosen et al.
D975,839 S 1/2023 Kuo
D977,087 S 1/2023 Siew
D983,353 S 4/2023 Babbage et al.
D984,639 S 4/2023 Fang
D988,500 S 6/2023 Ishikawa
D995,758 S 8/2023 McDermott et al.
D1,006,981 S 12/2023 Berney et al.
2001/0004970 A1 6/2001 Hollister
2001/0029949 A1 10/2001 Blackhurst et al.
2001/0031819 A1 10/2001 Iwata et al.
2002/0017302 A1 2/2002 Fukunaga et al.
2002/0112730 A1* 8/2002 Dutkiewicz ......... A61M 16/085 128/207.18
2002/0149200 A1* 10/2002 Fumioka ................. F16L 37/23 285/81
2002/0173748 A1 11/2002 McConnell
2003/0116963 A1* 6/2003 Teuscher ........... A61M 16/0816 285/179
2003/0136932 A1* 7/2003 Doyle ................. A61M 39/045 251/149.1
2004/0090066 A1 5/2004 Hoffmann
2004/0103686 A1 6/2004 Fehr et al.
2004/0108218 A1 6/2004 Stubergh
2004/0156915 A1* 8/2004 Harman ............... B65D 83/425 424/600
2004/0261797 A1 12/2004 White et al.
2005/0011524 A1 1/2005 Thomlinson et al.
2005/0028822 A1 2/2005 Sleeper et al.
2005/0077726 A1* 4/2005 White ............... A61M 16/1095 285/272
2005/0085794 A1 4/2005 Denoth et al.
2005/0188990 A1 9/2005 Fukunaga
2005/0283114 A1 12/2005 Bresina
2006/0107958 A1 5/2006 Sleeper
2006/0107960 A1 5/2006 Smart
2006/0113690 A1 6/2006 Huddart
2006/0157056 A1 7/2006 Burk
2007/0043334 A1 2/2007 Guala
2007/0088327 A1 4/2007 Guala
2007/0163588 A1 7/2007 Hebrank et al.
2007/0169825 A1 7/2007 Packham et al.
2007/0175473 A1 8/2007 Lewis et al.
2007/0255258 A1 11/2007 Matlock
2007/0276356 A1* 11/2007 Downing .............. A61M 39/12 604/535
2008/0041391 A1 2/2008 Worley
2008/0093846 A1 4/2008 Sparks et al.
2008/0105257 A1 5/2008 Klasek
2008/0142019 A1 6/2008 Lewis et al.
2008/0183153 A1 7/2008 Enns
2008/0190436 A1 8/2008 Jaffe et al.
2008/0214990 A1 9/2008 Smutney et al.
2008/0236577 A1 10/2008 Power
2008/0264413 A1 10/2008 Doherty
2008/0287920 A1 11/2008 Fangrow et al.
2009/0101147 A1 4/2009 Landis et al.
2009/0120434 A1 5/2009 Smith et al.
2009/0223523 A1 9/2009 Chang
2009/0223963 A1 9/2009 Bisio
2009/0240178 A1* 9/2009 Hanlon ................. F16L 37/098 601/151
2009/0266357 A1 10/2009 Varis et al.
2009/0299158 A1 12/2009 Boatner et al.
2010/0043789 A1 2/2010 Fine et al.
2010/0116272 A1 5/2010 Row et al.
2010/0148500 A1 6/2010 Uehara et al.
2010/0163051 A1 7/2010 Brewer et al.
2010/0168600 A1 7/2010 Adriance et al.
2010/0192957 A1 8/2010 Hobson et al.
2010/0206310 A1 8/2010 Matsubara et al.
2010/0242961 A1 9/2010 Mougel et al.
2010/0301596 A1* 12/2010 Amann ............... F16L 37/0985 285/31
2011/0009849 A1* 1/2011 Christensen .......... A61M 39/10 604/540
2011/0067704 A1* 3/2011 Kooij ................ A61M 16/0858 128/207.18
2011/0071504 A1 3/2011 Saltell
2011/0074148 A1* 3/2011 Imai ...................... A61M 39/26 285/308
2011/0120472 A1 5/2011 Lee et al.
2011/0139151 A1 6/2011 Burns
2011/0139826 A1 6/2011 Hair
2011/0148097 A1 6/2011 Ping
2011/0162644 A1 7/2011 Ujhazy et al.
2011/0240031 A1 10/2011 Jaffre
2011/0253136 A1 10/2011 Sweeney et al.
2011/0265796 A1 11/2011 Amarasinghe et al.
2012/0157914 A1* 6/2012 Stroup .................. A61M 39/10 604/207
2012/0172830 A1* 7/2012 Yokoyama ............ A61J 1/2089 604/413
2012/0247477 A1 10/2012 Stephenson et al.
2012/0305001 A1 12/2012 Tatkov
2013/0037030 A1 2/2013 Matula
2013/0079730 A1 3/2013 Mosler
2013/0104888 A1 5/2013 Landis et al.
2013/0133651 A1 5/2013 Barker et al.
2013/0167841 A1 7/2013 Sheffer et al.
2013/0245611 A1* 9/2013 Bonnet ................. A61M 39/10 604/535

(56) References Cited

U.S. PATENT DOCUMENTS

| | | | | |
|---|---|---|---|---|
| 2013/0255670 | A1 | 10/2013 | Ott et al. | |
| 2013/0264821 | A1 | 10/2013 | Duck | |
| 2013/0270820 | A1* | 10/2013 | Py | A61M 5/162 285/330 |
| 2013/0284167 | A1 | 10/2013 | Porteous et al. | |
| 2013/0292592 | A1* | 11/2013 | Py | B65B 39/001 251/149.6 |
| 2014/0000626 | A1 | 1/2014 | O'Connor et al. | |
| 2014/0014108 | A1 | 1/2014 | Dillard | |
| 2014/0053846 | A1 | 2/2014 | Wood | |
| 2014/0144438 | A1 | 5/2014 | Klasek | |
| 2014/0158127 | A1* | 6/2014 | Boucher | A61M 11/00 128/203.22 |
| 2014/0191501 | A1 | 7/2014 | Brugger et al. | |
| 2014/0200475 | A1 | 7/2014 | Rubin | |
| 2014/0238401 | A1 | 8/2014 | Paschall | |
| 2014/0261416 | A1 | 9/2014 | Arcilla et al. | |
| 2014/0305433 | A1* | 10/2014 | Rothermel | A61M 16/06 128/202.27 |
| 2014/0338669 | A1 | 11/2014 | Zhao et al. | |
| 2014/0373841 | A1 | 12/2014 | Nashed | |
| 2015/0021909 | A1* | 1/2015 | Gulliver | A61M 16/085 285/319 |
| 2015/0059745 | A1 | 3/2015 | Barker et al. | |
| 2015/0068519 | A1 | 3/2015 | Bambrilla | |
| 2015/0083121 | A1 | 3/2015 | Fisher | |
| 2015/0128944 | A1 | 5/2015 | Buechi | |
| 2015/0167877 | A1* | 6/2015 | Kendrick | A61M 16/0816 285/93 |
| 2015/0209568 | A1 | 7/2015 | Rosenquist | |
| 2015/0290416 | A1 | 10/2015 | Klasek | |
| 2015/0306332 | A1 | 10/2015 | Bafile et al. | |
| 2015/0320949 | A1 | 11/2015 | Jaffe | |
| 2015/0320962 | A1 | 11/2015 | Bafile et al. | |
| 2016/0001031 | A1 | 1/2016 | Laing et al. | |
| 2016/0038701 | A1 | 2/2016 | White et al. | |
| 2016/0082218 | A1 | 3/2016 | Lau | |
| 2016/0106913 | A1 | 4/2016 | Ng et al. | |
| 2016/0131292 | A1 | 5/2016 | Decker | |
| 2016/0193440 | A1 | 7/2016 | Sheffer et al. | |
| 2016/0199634 | A1* | 7/2016 | Gagliardoni | A61M 39/26 251/149.1 |
| 2016/0228668 | A1 | 8/2016 | Martin | |
| 2016/0287824 | A1 | 10/2016 | Chang | |
| 2016/0305574 | A1 | 10/2016 | Burdge | |
| 2017/0036007 | A1* | 2/2017 | Hallisey | A61M 39/26 |
| 2017/0065788 | A1 | 3/2017 | Chou | |
| 2017/0065789 | A1 | 3/2017 | Reed | |
| 2017/0197055 | A1 | 7/2017 | Moody | |
| 2017/0333662 | A1 | 11/2017 | Ovinsky et al. | |
| 2017/0361051 | A1 | 12/2017 | Eifler | |
| 2018/0064901 | A1 | 3/2018 | Colman | |
| 2018/0078728 | A1 | 3/2018 | Holyoake et al. | |
| 2018/0085544 | A1 | 3/2018 | Holyoake | |
| 2018/0117270 | A1 | 5/2018 | Bassin | |
| 2018/0140819 | A1 | 5/2018 | Yang | |
| 2018/0200148 | A1 | 7/2018 | Sanders | |
| 2019/0002344 | A1 | 1/2019 | Guo | |
| 2019/0022344 | A1 | 1/2019 | Lau et al. | |
| 2019/0151842 | A1 | 5/2019 | Williams et al. | |
| 2019/0167935 | A1 | 6/2019 | Siew et al. | |
| 2019/0381268 | A1 | 12/2019 | Colman | |
| 2020/0129724 | A1 | 4/2020 | Nelson | |
| 2021/0205589 | A1 | 7/2021 | Dong | |
| 2021/0322706 | A1 | 10/2021 | Lau et al. | |
| 2021/0361924 | A1 | 11/2021 | Gulliver et al. | |
| 2021/0402127 | A1 | 12/2021 | Lau et al. | |
| 2023/0021629 | A1 | 1/2023 | Ranjitsingh | |
| 2023/0147017 | A1 | 5/2023 | Holyoake | |

FOREIGN PATENT DOCUMENTS

| | | | |
|---|---|---|---|
| CN | 101365509 | | 2/2009 |
| CN | 101468222 | | 7/2009 |
| CN | 101686749 | | 3/2010 |
| CN | 201775849 | | 3/2011 |
| CN | 102019014 | | 4/2011 |
| CN | 102655807 | | 9/2012 |
| CN | 104420891 | | 3/2015 |
| DE | 3709122 | | 9/1988 |
| DE | 19615290 | | 1/1998 |
| DE | 102007063556 | | 7/2009 |
| EM | 000254420-0014 | | 11/2004 |
| EM | 008110019-0001 | | 9/2020 |
| EM | 008110019-0002 | | 9/2020 |
| EP | 1 068 889 | | 1/2001 |
| EP | 1 181 945 | | 2/2002 |
| EP | 0 809 768 | | 7/2002 |
| EP | 1 277 488 | | 1/2003 |
| EP | 1 314 446 | | 5/2003 |
| EP | 1 403 838 | | 3/2004 |
| EP | 1 408 313 | | 4/2004 |
| EP | 1 479 405 | | 11/2004 |
| EP | 1 481 702 | | 12/2004 |
| EP | 1 520 599 | | 4/2005 |
| EP | 1 023 912 | B1 | 11/2005 |
| EP | 1 449 502 | | 12/2007 |
| EP | 1 933 074 | | 6/2018 |
| EP | 2 906 287 | | 6/2019 |
| EP | 2 877 224 | | 9/2020 |
| EP | 2 925 396 | | 9/2020 |
| GB | 1563359 | | 3/1980 |
| GB | 2328260 | | 2/1999 |
| JP | 09-028806 | | 2/1997 |
| JP | 2002-126094 | | 5/2002 |
| JP | 2007-236567 | | 9/2007 |
| JP | 2009160031 | | 7/2009 |
| JP | D1639030 | | 8/2019 |
| JP | D1723039 | | 8/2022 |
| JP | D1737290 | | 2/2023 |
| KR | 1020040103139 | | 12/2004 |
| MY | 13-1228-0303-0001 | | 8/2014 |
| TW | 223055-0001 | | 1/2023 |
| TW | 2264550001 | | 3/2023 |
| WO | WO 90/014122 | | 11/1990 |
| WO | WO 94/004211 | | 3/1994 |
| WO | WO 97/015376 | | 5/1997 |
| WO | 9748433 | | 12/1997 |
| WO | WO 99/012598 | | 3/1999 |
| WO | WO 03/082406 | | 10/2003 |
| WO | 2003090827 | | 11/2003 |
| WO | WO 04/108218 | | 12/2004 |
| WO | WO 05/018524 | | 3/2005 |
| WO | WO 05/079670 | | 9/2005 |
| WO | WO 05/102431 | | 11/2005 |
| WO | WO 07/019625 | | 2/2007 |
| WO | WO 07/024812 | | 3/2007 |
| WO | 2008094532 | | 8/2008 |
| WO | 2008144298 | | 11/2008 |
| WO | WO 08/144447 | | 11/2008 |
| WO | WO 09/094532 | | 7/2009 |
| WO | WO 09/146484 | | 12/2009 |
| WO | WO 11/062510 | | 5/2011 |
| WO | WO 11/079226 | | 6/2011 |
| WO | WO 12/052903 | | 4/2012 |
| WO | WO 13/022356 | | 2/2013 |
| WO | WO 13/088439 | | 6/2013 |
| WO | WO 13/127474 | | 9/2013 |
| WO | WO 14/015382 | | 1/2014 |
| WO | WO 14/077706 | | 5/2014 |
| WO | WO 14/097145 | | 6/2014 |
| WO | WO 14/129912 | | 8/2014 |
| WO | WO 2014/205513 | | 12/2014 |
| WO | WO 15/038014 | | 3/2015 |
| WO | WO 2015/142192 | | 9/2015 |
| WO | WO 16/157101 | | 10/2016 |
| WO | WO 16/157105 | | 10/2016 |

OTHER PUBLICATIONS

Photos of current commercial connector illustrated in reference 1, 3 pages.

(56) References Cited

OTHER PUBLICATIONS

Salter Labs, "Air-Q Intubating Laryngeal Airways (ILA) The every-day airway that's ready for the unexpected."; Dec. 2018; 8 pages.
Huapa Mini hose connector for CPAP hose CPAP accessories Resmed air nasal masks, Amazon.com, first posted Oct. 9, 2018, https://amzn.to/3x62sdy, 8 pp.
Pall Corporation, Jun. 10, 2019, Multiple-Patient-Use Anesthesia Circuits, product description, 5 pp.
JML Medical, Adaptor One Way Valve 220D×221D w/Oxygen Stem, Teleflex, [Post date unknown], downloaded May 19, 2022, https://www.jmlmed.com/collections/respiratory-products/products/one-way-valve-by-teleflex, 2 pp.
New Leaf Home Medical, Pressure Line Adaptor for Ventilation Accessories, Medline, [Post date Unknown], downloaded May 19, 2022 https://newleafhomemedical.com/pressure-line-adaptor-for-ventilation-accessories/, 1 p.
RC Medical Incorporated, Hudson Dual Spray MDI Adaptor, CS/50, [Post date: Post date unknown], downloaded, May 19, 2022, https://www.rcmedical.com/viewProduct.cfm?productID=871, 1 p.
Fisher & Paykel ICON ThermoSmart Heated CPAP Tubing, 6 Foot, Fisher & Paykel, [Post date unknown], [Site seen Mar. 23, 2023], Seen at URL: https://helpmedicalsupplies.com/products/6-thermosmart-heated-hose-tubing-for-f-p-icon-cpap-machine?variant= 9981444522099 (Year: 2023), 1 p.
Replacement Non-Heated Hose Tubing for Fisher & Paykel SleepStyle Auto CPAP Machine, Fisher & Paykel, .cpapstoreusa.com, [Post Date: Jun. 26, 2022], [Site seen Mar. 23, 2023], Seen at URL: https://www.cpapstoreusa.com/product/ replacement-non-heated-hose-tubing-for-fisher-paykel-sleepstyle-auto-cpap-machine/ (Year: 2022), 1 p.
Replacement Tube Assembly for WIS_P, IBEET Short Tube Supplies-Quick Release & 360-Degree Rotatable, IBEET, Amazon.com, [Post date: Oct. 28, 2021], Seen at URL: https://www.amazon.com/Replacement-Tube-Assembly-Short-Supplies/dp/ B09GM12TMG (Year: 2021), 4 pp.
AQR Safety Connection, Staubli, [Post date: Nov. 29, 2023], [Site seen Aug. 9, 2023], Seen at URL: https://www.staubli.com/fr/en/fluid-connectors/products/quick-and-dry-disconnect-couplings/breathing-air.html (Year: 2023).
Prestan Rescue Mask Adapters 50 Pack, Prestan, heartsmart.com, [Post date: unknown], [Site seen Aug. 9, 2023], Seen at URL:+ https://www.heartsmart.com/prestan-rescue-mask-adapters-p (Year: 2023).
China National Intellectual Property Administration, Rejection Decision, Application No. 201710181804.X, dated Sep. 1, 2020, in 8 pages.
Chinese Patent Office, Notification Letter of Review Opinion, Taiwan Design Application No. 109304590, dated Jan. 6, 2021 in 4 pages.
Combined Search and Examination Report in corresponding United Kingdom Patent Application No. GB 10800268.3, dated Jan. 25, 2018, in 6 pages.
European Patent Office, Examination Report, Application No. 16840949.8, dated Feb. 16, 2021 in 4 pages.
Examination Report for Australian Patent Application 2016314616, dated Apr. 30, 2020; 4 pages.
Examination Report for GB1803152.6, dated May 26, 2020, 2 pages.
Examination Report for JP2018-512159, dated Aug. 20, 2020, 15 pages total with machine translation.
Examination Report in corresponding Australian Patent Application No. 2017202180, dated Aug. 31, 2018, in 3 pages.
Examination Report in corresponding Chinese Patent Application No. 201710181804.X, dated May 29, 2019, in 8 pages.
Examination Report in corresponding United Kingdom Patent Application No. 1800268.3, dated Jul. 3, 2018, in 2 pages.
Examination Report in corresponding United Kingdom Patent Application No. 1807231.4, dated Aug. 31, 2018, in 2 pages.
Examination Report in corresponding United Kingdom Patent Application No. 1810896.9, dated Nov. 20, 2018, in 5 pages.
Examination Report in corresponding United Kingdom Patent Application No. GB 10800268.3, dated Jun. 8, 2018, in 3 pages.
Extended European Search Report issued in App. No. EP24179119, dated Oct. 15, 2024, 8 pages.
Extended Search Report in corresponding European Patent Application No. 17195173.4, dated May 22, 2018, in 13 pages.
GB Intellectual Property Office, Examination Report under Section 18(3), Application No. GB1803152.6, dated Oct. 26, 2020, in 2 pages.
International Search Report, PCT/IB2016/055258, dated Nov. 14, 2016, in 4 pages.
Japanese Patent Office, Notice of Reasons of Refusal, Official Action, Japanese Application No. 2019-2233563, dated Feb. 25, 2021, in 9 pages.
JML Medical, Adaptor One Way Valve 220Dx221 D w/Oxygen Stem, Teleflex, [Post date unknown], downloaded May 19, 2022, https://www.jmlmed.com/collections/respiratory-products/products/one-way-valve-by-teleflex, 2 pp.
Notification of First Office Action, CN Application No. 201680060677.1, dated Mar. 19, 2020, 7 pages.
Office Action in corresponding Australian Patent Application No. 2017202180, dated Jul. 19, 2019, in 3 pages.
Office Action in corresponding Canadian Patent Application No. 2,844,802, dated Jun. 12, 2019, in 4 pages.
Office Action in corresponding Canadian Patent Application No. 2844802, dated Jun. 6, 2018, in 4 pages.
Office Action in corresponding Japanese Patent Application No. 2014-524961, dated Nov. 8, 2017, in 2 pages.
Office Action in corresponding United Kingdom Patent Application No. 1807231.4, dated Jun. 19, 2018, in 9 pages.
PCT Application No. PCT/NZ2012/000142 International Preliminary Report on Patentability mailed Feb. 14, 2014 in 6 pages.
PCT Application No. PCT/NZ2012/000142 International Search Report and Written Opinion Mailed Jan. 22, 2013, in 14 pages.
Photos of current commercial connector illustrated in reference 1, 3 pages. [Assume the date 2012 for examination purposes. ].
Supplementary European Search Report, European Patent Office, Application No. EP 16 84 0949, dated Jan. 17, 2019, in 3 pages.
The State Intellectual Property Office of People's Republic of China, First Office Action; Application No. 201680060677.1, dated Mar. 19, 2020; 26 pages.
Thomas Scientific, Coupling Insert, In-Line Hose Barb, [Post date: unknown], [Site seen Nov. 21, 2023], https://www.thomassci.com/Laboratory-Supplies/Tubing-Connectors/_/Coupling-Insert-In-Line-Hose-Barb-Straight-Thru2, accessed Nov. 21, 2023.
Korean Office Action (including English translation) issued in App. No. KR20247009276 dated Jan. 26, 2026 (pp. 1-18).

* cited by examiner

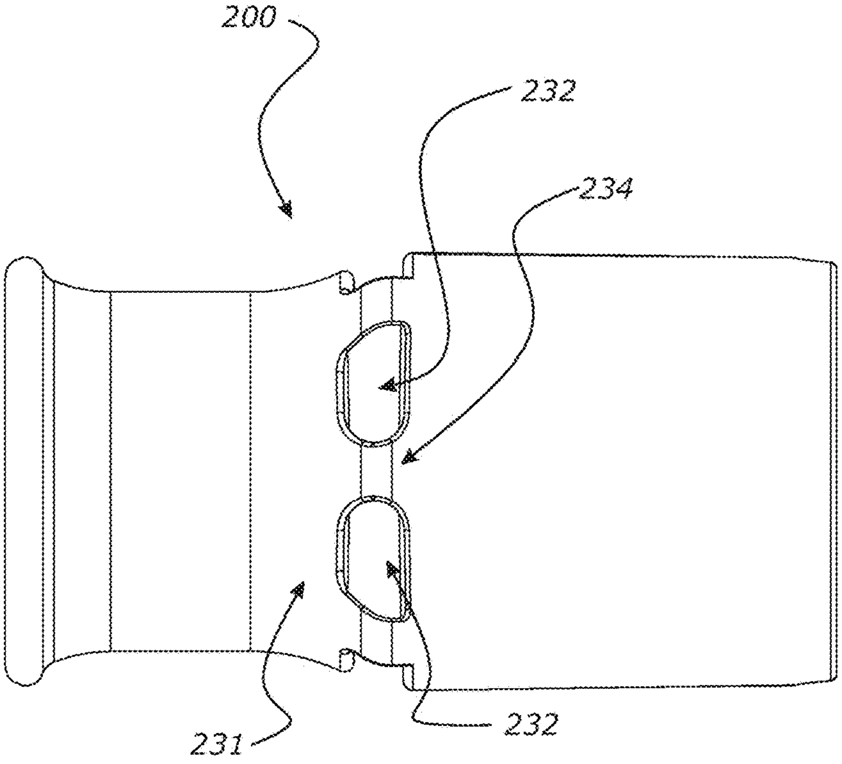
FIGURE 28B1
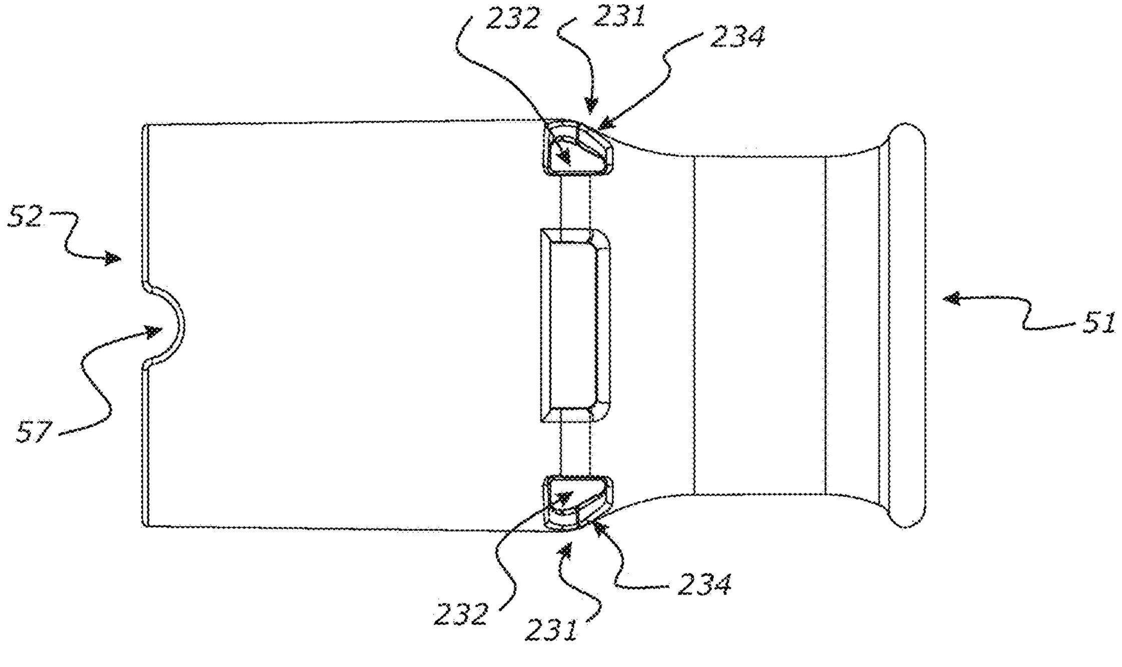
FIGURE 28B2

CONNECTORS FOR CONDUITS

FIELD OF THE INVENTION

The present invention relates to connectors for use in breathing circuits, more particularly, though not solely, to connectors to be used at the terminal end of a breathing conduit.

BACKGROUND TO THE INVENTION

Providing connectors for the terminal ends of breathing conduit is of importance for the continued and safe delivery of gas therapies to patients.

For example, humidified or other gases may be transported via a series of conduits to provide for a breathing circuit, supplying the gas to a patient interface, such as for example to nasal cannula, mouthpieces, full face masks, nasal masks. Different conduits may be used in different parts of the breathing circuit.

For example, conduit most closely associated with the patient may be of small diameter and may need to be more flexible, whilst conduit further away from the patient can be of a larger diameter, less flexible and may include electronics, such as heaters or other sensing circuitry.

Given the sequencing of different conduits, and the variety of patient interfaces that may be attached to these different conduits, a connector or system of connectors which helps a user make a correct connector connection finds particular advantage.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is therefore an object of the present invention to provide a connector or system of connectors which will go at least some way towards addressing the foregoing problems or which will at least provide the industry and/or public with a useful choice.

At times, an airflow source may need to be removed or replaced, or a patient interface may need to be removed from a breathing circuit, or other conduit forming a part of a breathing circuit may need to be replaced. If detaching the particular component (e.g. conduit or a patient interface) from the circuit is difficult or time consuming, such detachments may adversely impact on the maintenance or continued delivery of a gas therapy to a patient, or may become a frustration for the person making such a detachment. Further, in emergencies, a slow or difficult connection mechanism can potentially place the patient's health in danger. Thus, a conduit connector that provides a "quick-connect" or "quick-release" capability, and yet which facilitates the rapid and correct alignment and connection of a new connector, as well as facilitating interchangeability of components, can provide greater comfort and/or safety for the patient.

In a first aspect, there is provided a connector to be provided at a terminal end of a breathing conduit, the connector comprising:

a body, the body comprising a first end and a second end, the body internally defining a lumen for the passage of gas therethrough between each of the first and second ends, the first end, in use, being engaged or engageable with the terminal end of the breathing conduit or at least a component to be associated with the terminal end of the breathing tube, and the second end, in use, to be engaged or engageable with another connector, and wherein an internal surface of the body comprises one or more internal connection features configured for connection with said another connector which may be received internally therein, and wherein an external surface of the body comprises one or more external alignment feature(s) configured for aligning said connector or another connection into an externally aligned connection therebetween.

In a second aspect, there is provided a connector to be provided at a terminal end of a breathing conduit, the connector comprising:

a body, the body comprising a first end and a second end, the body internally defining a lumen for the passage of gas therethrough between each of the first and second ends, the first end, in use, being engaged or engageable with the terminal end of the breathing conduit or at least a component to be associated with the terminal end of the breathing tube, and the second end, in use, to be engaged or engageable with another connector, and wherein an internal surface of the body comprises one or more internal connection features configured for connection with said another connector which may be received internally therein, and wherein one or more external visual aid(s) is/are configured for, in use, providing an externally visible guide for alignment of said connector or another connector into an aligned connection therebetween.

According to the above first and second aspects, there is provided one or more additional features described by the optional configurations below.

The one or more internal connection features may be surface feature(s) that extend radially inward from the surface of an internal side wall of the body.

The one or more internal connection features may comprise one or more tabs.

The one or more tab(s) may be a raised protrusion.

The internal connection features may be oriented so as to be radially aligned with said one or more external alignment features and/or said one or more external visual aids.

There may be a pair of said internal connection features.

At least one (optionally one) of said internal connection features may comprise a longitudinally extensive channel or recess, said channel or recess may be configured to locate, retain, or position a printed circuit board (PCB) arrangement.

The internal surface may comprise one or more internal alignment features configured for aligning at least one connection feature of another connector to be received internally thereof into an aligned connection orientation therewith.

Said internal surface may comprise one or more internal alignment features configured to, in use, rotatably orient a male connection feature of another connector into an aligned connection orientation for connection with the connector, or at least into connection with, said one or more internal connection features located on or about the internal surface of the body.

The internal alignment feature(s) may be surface feature (s) that extend radially inward from the surface of an internal side wall of the body.

The internal alignment feature(s) may comprise one or more tab(s).

The one or more tab(s) may be a raised protrusion.

The one or more tab(s) may comprise a pair of shoulders, sloping away from each other and away from an end of the tab at the intersection of the shoulders, the end of the tab located substantially more toward a terminal end of the second end of the connector than the shoulders.

The internal alignment feature(s) may be one or more ribs extending substantially in a longitudinal direction of said connector and along said internal surface, optionally being a surface of an internal side wall of the body.

The internal alignment features may comprise: 1-10 ribs, or 2-8 ribs, or 4-6 ribs, or 2 ribs, or 3 ribs, or 4 ribs, or 6 ribs, or 8 ribs, or 10 ribs.

Two or more sets of internal alignment features may be provided on or about the internal surface of the body, optionally there are two sets of alignment features.

Each said set of internal alignment may comprise an equal number of internal alignment features as another set.

The internal surface may comprise two of said internal alignment features.

The internal alignment features may, in use, rotatably align a pair of fingers extending from another connector when inserted into or placed into engagement or surface contact with said internal surface of the connector.

The first end may be configured for engagement with the terminal end of the breathing conduit.

The first end may comprise a sleeved portion to be attached to the terminal end of the breathing conduit and to form a pneumatic connection therewith.

At least a part of said sleeved portion may be insertable into or to be located or housed within an interior surface or the lumen of the terminal end of the breathing conduit.

At least a part of said sleeved portion may be receivable upon or to be located or housed upon an exterior surface of the terminal end of the breathing conduit.

The external alignment feature(s) and/or the external visual aid(s) may comprise one or more external surface features extending radially outwardly from the outer surface of an external side wall of the body.

The external alignment feature(s) may comprise one or more tab(s).

The one or more tab(s) may be a raised protrusion.

The external alignment feature(s) may be one or more rib(s) (or protrusion(s)) extending substantially in a longitudinal direction with the connector and along said external surface, optionally being a surface of an external side wall of the body.

The at least one, or each rib or protrusion may comprise a pair of shoulders, said shoulders sloping away from each other and away from an end of the rib or protrusion at the intersection of the shoulders, the end of the rib or protrusion located substantially more toward a terminal end of the second end of the connector than the shoulders.

The at least one, or each rib or protrusion may be substantially tongue shaped, and/or substantially triangular and/or substantially tapers toward an end.

The external alignment features may comprise: 1-10 ribs, or 2-8 ribs, or 4-6 ribs, or 2 ribs, or 3 ribs, or 4 ribs, or 6 ribs, or 8 ribs, or 10 ribs.

External alignment features may be spaced, arrayed or arranged evenly or equidistantly from each other about the circumference or a radius of the external surface.

The external alignment feature may be a projection of a length that extends in a substantially longitudinal direction of said connector and along said external surface, and a height of said projection from the external surface varies along said length.

The height of said external alignment feature may taper along said length.

The height of said projection may either:

a. reduces in a direction extending from a base of the external alignment feature toward a terminal end of the second end of the connector, or b. increases in a direction extending from a base of the external alignment feature toward a terminal end of the second end of the connector.

Provided substantially at or toward a base of a or each said external alignment feature may be a stepped protrusion, the stepped protrusion being a more radially outwardly extending projection than an adjacent portion of the external alignment feature.

The stepped projection may be configured to be co-located or co-locatable for keying with a reciprocally shaped recess or cut-out of at least a part of a sleeved portion of another connector when brought to bear into connection therewith during a connection between the connector and said another connector.

The stepped projection may be configured to act as a key to reciprocally locate with a reciprocally shaped recess or cut-out of a component brought into connection therewith.

Provided substantially at or toward a base of a or each said external alignment feature may be a recess or cut-out, the recess or cut-out configured for receiving a protrusion or projection of a reciprocally shaped portion of another connector.

The recess or cut-out may be configured to be co-located or co-locatable for keying with a reciprocal protrusion or projection of at least a part of a sleeved portion of another connector when brought to bear into connection therewith during a connection between the connector and said another connector.

The recess or cut-out may be configured to act as a keyway to reciprocally locate with a reciprocally shaped protrusion or projection of a component brought into connection therewith.

The stepped protrusion or recess or cut-out may be of the following shapes or profiles for locating with or receiving a substantially reciprocally shaped recess or cut-out, or a protrusion or projection: semi-circular, triangular, rectangular or other recti-linear or geometric shapes, elliptical, wedge shaped.

A radially extensive flange or lip may project from the external surface of the body.

Said flange or lip may substantially defines a stop end for a point or length of maximum engagement of another connector when made with the external surface of the connector.

Said flange or lip may comprise one or both of:

i. one or more radially and/or longitudinally recessed or grooved regions, or ii. one or more radially and/or longitudinally extending projection regions.

Said flange or lip may be longitudinally extensive so as to be configured for an engagement with the terminal end of the breathing conduit.

A sheath, optionally may be an overmoulded sheath, providing for a pneumatic engagement of an external surface of the body with a terminal end of a breathing tube, optionally the sheath pneumatically engages the first end of the connector with the terminal end of a breathing tube.

Said sheath may comprise one or both of:

i. one or more radially and/or longitudinally recessed or grooved regions, or ii. one or more radially and/or longitudinally extending projection regions.

Said recessed or grooved regions and/or said extending projection regions of said sheath may be wholly or at least partially aligned with said recessed or grooved regions and/or said extending projection regions of said flange or lip.

An internal surface of the body, optionally toward the second end of the connector, may be configured to locate, retain, or position a printed circuit board (PCB) arrangement.

The PCB facilities circuitry may be for: control, sensing (e.g. temperature, humidity, flow rate), heating (e.g. heater wires) or other electronic components for a breathing conduit to be used as a part of a breathing circuit.

The connector may provide for a plurality of separate sealing surfaces upon which separate connections with separate another connectors may be made, optionally there may be two separate sealing surfaces to accommodate two different connectors.

The connector may be configured to provide a first separate sealing surface when a separate connection is made thereto by another connector, the first sealing surface defined by one or both of:

a side wall surface of a radially extensive flange or lip projecting from the external surface of the body, said side wall to face a terminal end face of another connector which may be brought to bear substantially upon said side wall, or an inner surface, substantially at or toward the terminal end of the second end of the connector when brought to bear upon a radially outward facing surface of another connector, such as a radially outwardly facing surface of another connector.

The connector may be configured to provide a body of the second end, for sealing upon a second sealing surface of another connector, the second sealing surface defined by:

an internal side wall surface provided substantially at or toward a base end of the second end of the another connector, in use, the body of the second end of the connector being brought to bear substantially upon the internal side wall surface or a location along the internal side wall surface at or toward the base end of another connector.

The connector may be configured to provide a body of the second end for sealing upon a third sealing surface of another connector, the third sealing surface defined by:

an internal side wall surface of a protrusion extending radially inwardly of the internal side wall surface of the second end of the another connector, when said body of the second end of the is brought to bear substantially upon the surface or a location along the surface of the protrusion of the another connector.

The connector may be configured to provide a body of the second end for sealing upon a fourth sealing surface of another connector, the fourth sealing surface defined by:

an internal side wall surface of the second end of the another connector, where the internal side wall surface extends as a shoulder radially outwardly from one or more male connection features (such as one or more locking fingers), a part of the body of the second end of the connector being brought to bear substantially upon a radially outward surface of the shoulder.

The connector may be configured to provide a body of the second end for sealing upon a fifth sealing surface of another connector, the fifth sealing surface defined by:

a radially outward surface of one or more male connection features, in particular a radially outward surface of one or more locking fingers located within a second end of the another connector.

Where the connector may be configured to provide a body of the second end, for sealing upon a sixth sealing surface of another connector, the sixth sealing surface may be defined by one or both of:

a lateral face or ledge of a shoulder extending radially outwardly from one or more male connection features, in particular a radially outwardly extensive face or ledge extending radially outwardly from one or more locking fingers located within a second end of another connector, or a lateral face or a base extending as a floor between an outward periphery of a shoulder extending radially outwardly from one or more male connection features of another connector, such a lateral face or base extending as a floor being located within a second end of the another connector.

The or an external alignment feature(s) of the connector may be shaped or configured to:

prevent connection of the internal connection features of the connector with another connector, when the external alignment feature(s) of the connector and an external alignment feature of another connector are in an unaligned orientation, and/or allow connection of the internal connection features of the connector with another connector, when the external alignment feature(s) of the connector and an external alignment feature of another connector are in an aligned orientation.

In a third aspect, there is provided a connector to be provided at a terminal end of a breathing conduit, the connector comprising:

a body, the body comprising a first end and a second end, the body internally defining a lumen for the passage of gas therethrough between each of the first and second ends, the first end, in use, being engaged or engageable with the terminal end of the breathing conduit or at least a component to be associated with the terminal end of the breathing tube, and the second end, in use, to be engaged or engageable with another connector, and wherein an internal surface of the body comprises one or more internal male connection features extending therein configured for connection with a female end or female part of another connector receivable of said male connection features, the male internal connection features comprising one or more (optionally a pair) of locking fingers, and wherein the connector further comprises one or both of:

a. surrounding of the one or more internal male connection features is an outer wall, an exterior surface of the outer wall being tapered, tapered in a direction substantially longitudinally with the connector, b. surrounding of the one or more internal male connection features is an outer wall, the outer or at least an exterior surface of the outer wall, comprising one or more external alignment feature(s) configured for aligning said connector or another connection into an externally aligned connection therebetween, and/or one or more external visual aid(s) is/are configured for, in use, providing an externally visible guide for alignment of said connector or another connector into an aligned connection therebetween.

In a fourth aspect, there is provided a connector to be provided at a terminal end of a breathing conduit, the connector comprising:

a body, the body comprising a first end and a second end, the body internally defining a lumen for the passage of gas therethrough between each of the first and second ends, the first end, in use, being engaged or engageable with the terminal end of the breathing conduit or at least a component to be associated with the terminal end of the breathing tube, and the second end, in use, to be engaged or engageable with another connector, and wherein an internal surface of the body comprises one or more internal male connection features extending therein configured for connection with a female end or female part of another connector receivable of said male connection features, the male internal connection features comprising one or more (optionally a pair) of locking fingers, and wherein the connector further comprises an outer wall surrounding of the one or more internal male connection features is an outer wall, an exterior surface of the outer wall being tapered, tapered in a direction substantially longitudinally with the connector, In a fifth aspect, there is provided a connector to be provided at a terminal end of a breathing conduit, the connector comprising:

a body, the body comprising a first end and a second end, the body internally defining a lumen for the passage of gas therethrough between each of the first and second ends, the first end, in use, being engaged or engageable with the terminal end of the breathing conduit or at least a component to be associated with the terminal end of the breathing tube, and the second end, in use, to be engaged or engageable with another connector, and wherein an internal surface of the body comprises one or more internal male connection features extending therein configured for connection with a female end or female part of another connector receivable of said male connection features, the male internal connection features comprising one or more (optionally a pair) of locking fingers, and wherein the connector further comprises an outer wall surrounding of the one or more internal male connection features, the outer or at least an exterior surface of the outer wall, comprising:

one or more external alignment feature(s) configured for aligning the outer wall of said connector, or said connector, or another connection into an externally aligned connection therebetween, and/or one or more external visual aid(s) is/are configured for, in use, providing an externally visible guide for alignment of said connector or another connector into an aligned connection therebetween.

According to the above third, fourth, and fifth aspects, there is provided one or more additional features described by the optional configurations above or below.

A diameter of the second end's outer wall may be smallest at a terminal end of the second end, with the diameter increasing in a direction extending away from the terminal end of the second end towards the first end.

The one or more locking fingers may be housed substantially within the second end of the connector.

A space may be defined between an outer surface of the one or more internal male connection features and an inner surface of the outer wall.

The outer wall may comprise one or more alignment feature(s) and/or one or more external visual aid(s), the one or more alignment feature(s) configured for aligning of said outer wall and said connector, or another connection, into an aligned connection therebetween, and/or the one or more external visual aid(s) is/are configured for, in use, providing an externally visible guide for alignment of said connector or another connector into an aligned connection therebetween.

Said one or more internal male connection features may be oriented so as to be radially aligned with said one or more external alignment features and/or said one or more external visual aids.

The external alignment feature(s) may comprise one or more cut-outs in a terminal end face of the outer wall of the second end, said cut-outs configured to be received by a substantially reciprocally shaped portion on a connector to which said outer wall is to be placed into contact.

External alignment features may be spaced, arrayed or arranged evenly or equidistantly from each other about the circumference a terminal end face of the outer wall of the second end.

The external alignment features may be configured to be co-located or co-locatable for keying with a reciprocally shaped projection of a sleeved portion of another connector when brought to bear into connection therewith during a connection between a terminal face of the second end of the connector and said another connector.

Said locking fingers may comprise a recess on an outer surface of each said finger, said recess to receive an internal connection feature, such as a raised protrusion that may extend in a radially inward direction toward said recess or a tab, of another connector configured for connection thereto.

The recess may be shaped for receipt of the internal connection feature of another connector.

A tip of said locking fingers may be of an at least partially chamfered configuration.

Provided at a terminal face of the outer wall of the second end of the connector may be a recess or cut-out, the recess or cut-out configured for receiving or being placed into connection with a protrusion or projection of a reciprocally shaped portion of another connector.

The recess or cut-out may be configured to be co-located or co-locatable for keying with a reciprocally protrusion or projection of at least a part of a sleeved portion of another connector when brought to bear into connection therewith during a connection between the connector and said another connector.

The recess or cut-out may be configured to act as a keyway to reciprocally locate with a reciprocally shaped protrusion or projection of a component brought into connection therewith.

Provided substantially at or toward a terminal face of the outer wall of the second end of the connector may be a longitudinally extensive protrusion, the protrusion being a more longitudinally extending projection than an adjacent portion of the terminal face of the outer wall of the second end of the connector.

The protrusion may be configured to be co-located or co-locatable for keying with a reciprocally shaped recess or cut-out of at least a part of a portion of another connector when brought to bear into connection therewith during a connection between the connector and said another connector.

The protrusion may be configured to act as a key to reciprocally locate with a reciprocally shaped recess or cut-out of a component brought into connection therewith.

The alignment feature may be a recess or cut-out of the following shapes or profiles for locating with or receiving a substantially reciprocally shaped protrusion or projection of another connector: semi-circular, triangular, rectangular or other recti-linear or geometric shapes, elliptical, wedge shaped.

The outer wall may be a sleeve, configured for use as a 22 mm male taper connector to another connector comprising a female connection facility.

The outer wall may be a sleeve, configured for use as a 22 mm female taper connector to another connector comprising a male connection facility.

The connector body may be formed of Polycarbonate (PC), Polyethylene (PE), Acrylonitrile Butadiene Styrene (ABS) or polypropylene (PP).

The body of the connector may comprise an outwardly flared portion located at the first end of the connector.

The internal surface of the second end of the body further may comprise a protrusion for an engagement (e.g. interference fit) with a commensurately shaped portion of another connector to be received by or within the internal surface bounded by the outer wall.

The protrusion may extend as a shoulder radially outwardly from the one or more locking fingers, optionally also extending longitudinally in a direction toward an open end of the second end of the connector.

The protrusion may extend as a shoulder radially outwardly from one or both of:

- the one or more locking fingers,
- a base extending as a floor from the inner surface of the outer wall,
- optionally the shoulder extends longitudinally in a direction toward an open end of the second end of the connector.

A space may be defined between a radially outward surface of the shoulder and an inner surface of the outer wall, said space receivable of a terminal end of another connector, the terminal end of the another connector received as an interference fit between the outward surface of the shoulder and the inner surface of the outer wall.

Substantially adjacent to, or at least in part abutting the shoulder and the inner surface of the outer wall, may be a base, the base extending as a floor between an outward periphery of the shoulder and the inner surface of the wall.

The base may define a sealing surface upon with a terminal end or a face of a terminal end of another connector may become engaged therewith, optionally forming a pneumatic connection.

A cuff may be provided about the first end of the connector body, and optionally at least partially overlapping of a portion of the second end of the connector body.

The cuff may be pre-formed or may be an overmoulded material overmoulded about the connector body.

The cuff may be dimensioned to as to provide for a relatively smooth or uninterrupted outer surface contour with an exterior surface of the outer wall substantially abutting or substantially adjacent to an intersection with the cuff.

Said cuff may comprise an indicator of size of the connector upon which it is provided, or for a particular component or size of a component to be associated with the connector (optionally the component being a patient interface, such as a nasal cannula).

The cuff may be colour-coded as an indicator of a connector size or for a particular component or size of component to be associated with the connector (optionally the component being a patient interface, such as a nasal cannula).

The cuff may be dimensioned to transition from a substantially circular exterior surface contour form, when substantially abutting or substantially adjacent to or with an exterior surface of the outer wall of the connector, to a substantially square exterior surface contour form provided substantially (optionally wholly) about the first end of the connector body.

The cuff may extend from the second end of the connector body to overlap upon an exterior surface of a breathing tube to which said connector is to be, in use, engaged or be engageable, or said cuff extends to overlap upon at least a portion of a component to be associated with the terminal end of the breathing tube.

The cuff may be an elastic or elasticised material, optionally being a silicone or thermoplastic elastomers (TPE).

The body of the connector may comprise at least one recess or groove shaped to receive one or more splines on an inner surface of the cuff.

A swivel-type connector component may be, in use, connected with the first end of the connector.

The swivel-type connector may be configured to connect with the terminal end of a conduit, and the swivel-type connector is configured to connect to the body of the connector.

The connector may comprise at least one retaining protrusion, the retaining protrusion extending in a radially inward direction from the body of the connector.

The retaining protrusion may comprise one or both of:

- a ramped surface optionally ramped away from the first end of the body
- a surface substantially perpendicular to the inner wall of a body of the connector.

The connector may comprise at least one attachment arm.

The attachment may comprise the at least one retaining protrusion.

The at least one attachment arm may be cantilevered relative to the body of the connector to allow for flexibility of the attachment arm in at least a direction radial to the body of the connector optionally radially inward, outward or both.

The connector may comprise at least one cut-out region located around at least part of the attachment arm. The cut-out region promoting flexibility in a radial direction.

The connector may comprise a pair of attachment arms.

The attachment arm may be located within the recess or groove shaped to receive a spline on an inner surface of a cuff.

The body of the connector or the attachment arm may comprise a recess to receive part of said swivel-type connector component.

The swivel-type connector component may connect to the conduit via a thread.

The swivel-type connector may connect to the first end such that relative movement of the connector body and swivel-type connector is allowed rotationally, yet prevented axially.

The swivel-type connector may comprise a surface or surfaces which form(s) a rotatable seal with the inner surface of the connector body.

The connector may be configured to provide a first separate surface for sealing upon when a separate connection is made thereto by another connector, the first surface defined by:

a terminal face of the second end of the connector when brought to bear upon a flange or lip (or shoulder) that projects outwardly or away from an external surface of the body of another connector.

The connector may be configured to provide a second separate surface for sealing upon when a separate connection is made thereto by another connector, the second surface defined by:

an internal side wall surface provided substantially at or toward a base end of the second end of the connector, a part of another connector (such as a lip or flange, optionally which may include a shoulder) being brought to bear substantially upon the internal side wall surface or a location along the internal side wall surface at or toward the base end.

The connector may be configured to provide a third separate surface for sealing upon when a separate connection is made thereto by another connector, the third surface defined by:

an internal side wall surface of a protrusion extending radially inwardly of the internal side wall surface of the second end, a part of another connector (such as a lip or flange, optionally which may include a shoulder) being brought to bear substantially upon the surface or a location along the surface of the protrusion.

The connector may be configured to provide a fourth separate surface for sealing upon when a separate connection is made thereto by another connector, the fourth surface defined by:

an internal side wall surface of the second end of the connector, where the internal side wall surface extends as a shoulder radially outwardly from said one or more male connection features (such as the one or more locking fingers), a part of another connector (such as a lip or flange, optionally which may include a shoulder) being brought to bear substantially upon a radially outward surface of the shoulder.

The connector may be configured to provide a fifth separate surface for sealing upon when a separate connection is made thereto by another connector, the fifth surface defined by:

a radially outward surface of the one or more male connection features, in particular a radially outward surface of one or more locking fingers located within the second end of the connector.

The connector may be configured to provide a sixth separate surface for sealing upon when a separate connection is made thereto by another connector, the sixth surface defined by one or both of:

a lateral face or ledge of a shoulder extending radially outwardly from the one or more male connection features, in particular a radially outwardly extensive face or ledge extending radially outwardly from one or more locking fingers located within the second end of the connector, or a lateral face or the base extending as a floor between an outward periphery of a shoulder extending radially outwardly from one or more male connection features, and the inner surface of the wall.

The or an external alignment feature(s) of the connector may be shaped or configured to:

prevent connection of the internal connection features of the connector with another connector, when the external alignment feature(s) of the connector and an external alignment feature of another connector are in an unaligned orientation, and/or allow connection of the internal connection features of the connector with another connector, when the external alignment feature(s) of the connector and an external alignment feature of another connector are in an aligned orientation.

In a sixth aspect, there is provided a connector for use with a conduit to supply gases to a user comprising:

a body, the body comprising a first end and a second end, the body internally defining a lumen for the passage of gas therethrough between each of the first and second ends, the first end, in use, being engaged or engageable with the terminal end of the breathing conduit or at least a component to be associated with the terminal end of the breathing tube, and the second end, in use, to be engaged or engageable with another connector, and wherein an external surface of the body comprises a cuff provided at least substantially about the first end of the connector body (optionally at least partially overlapping of a portion of the second end of the connector body), said cuff extending substantially longitudinally down at least a part of a length of the breathing tube to be engaged or engageable with the first end, and wherein said cuff is an elasticised or elastic-type material.

According to the above aspect, there is provided one or more additional features described by the optional configurations above or below.

Overlap of said cuff with a said breathing tube may facilitate for at least in part a relief of strain otherwise imparted to an engagement or connection made between the breathing tube and said first end or a component to be associated with said first end.

A diameter of the second end's outer wall may be smallest at a terminal end of the second end, with the diameter increasing in a direction extending away from the terminal end of the second end towards the first end.

The one or more locking fingers may be housed substantially within the second end of the connector.

A space may be defined between an outer surface of the one or more internal male connection features and an inner surface of the outer wall.

The outer wall may comprise one or more alignment feature(s) and/or one or more external visual aid(s), the one or more alignment feature(s) configured for aligning of said outer wall and said connector, or another connection, into an aligned connection therebetween, and/or the one or more external visual aid(s) is/are configured for, in use, providing an externally visible guide for alignment of said connector or another connector into an aligned connection therebetween.

Said locking fingers may comprise a recess on an outer surface of each said finger, said recess to receiving an internal connection feature, such as a raised protrusion that may extend in a radially inward direction toward said recess or a tab, of another connector configured for connection thereto.

The recess may be shaped for receipt of the internal connection feature of another connector.

A tip of said locking fingers may be of an at least partially chamfered configuration.

Provided at a terminal face of the outer wall of the second end of the connector may be a recess or cut-out, the recess or cut-out configured for receiving a protrusion or projection of a reciprocally shaped portion of another connector.

The recess or cut-out may be configured to be co-located or co-locatable for keying with a reciprocally protrusion or projection of at least a part of a sleeved portion of another connector when brought to bear into connection therewith during a connection between the connector and said another connector.

The recess or cut-out may be configured to act as a keyway to reciprocally locate with a reciprocally shaped protrusion or projection of a component brought into connection therewith.

Provided substantially at or toward a terminal face of the outer wall of the second end of the connector may be a longitudinally extensive protrusion, the protrusion being a more longitudinally extending projection than an adjacent portion of the terminal face of the outer wall of the second end of the connector.

The protrusion may be configured to be co-located or co-locatable for keying with a reciprocally shaped recess or cut-out of at least a part of a portion of another connector when brought to bear into connection therewith during a connection between the connector and said another connector.

The protrusion may be configured to act as a key to reciprocally locate with a reciprocally shaped recess or cut-out of a component brought into connection therewith.

The stepped protrusion or recess or cut-out may be of the following shapes or profiles for locating with or receiving a substantially reciprocally shaped recess or cut-out, or a protrusion or projection: semi-circular, triangular, rectangular or other recti-linear or geometric shapes, elliptical, wedge shaped.

The outer wall may be a sleeve, configured for use as a 22 mm male taper connector to another connector comprising a female connection facility.

The outer wall may be a sleeve, configured for use as a 22 female taper connector to another connector comprising a male connection facility.

The connector body may be formed of Polycarbonate (PC), Polyethylene (PE), Acrylonitrile Butadiene Styrene (ABS) or polypropylene (PP).

The internal surface of the second end of the body further may comprise a protrusion for an engagement (e.g. an interference fit) with a commensurately shaped portion of another connector to be received by or within the internal surface bounded by the outer wall.

The protrusion may extend as a shoulder radially outwardly from the one or more locking fingers, optionally also extending longitudinally in a direction toward an open end of the second end of the connector.

The protrusion may extend as a shoulder radially outwardly from one or both of:

- the one or more locking fingers,
- a base extending as a floor from the inner surface of the outer wall, optionally the shoulder extends longitudinally in a direction toward an open end of the second end of the connector.

A space may be defined between a radially outward surface of the shoulder and an inner surface of the outer wall, said space receivable of a terminal end of another connector, the terminal end of the another connector received as an interference fit between the outward surface of the shoulder and the inner surface of the outer wall.

Substantially adjacent to, or at least in part abutting the shoulder and the inner surface of the outer wall, may be a base, the base extending as a floor between an outward periphery of the shoulder and the inner surface of the wall.

The base may define a sealing surface upon with a terminal end or a face of a terminal end of another connector may become engaged therewith, optionally forming a pneumatic connection.

A cuff may be provided about the first end of the connector body, and optionally at least partially overlapping of a portion of the second end of the connector body.

The cuff may be a pre-formed or an overmoulded material overmoulded about the connector body.

The cuff may be dimensioned to as to provide for a relatively smooth or uninterrupted outer surface contour with an exterior surface of the outer wall substantially abutting or substantially adjacent to an intersection with the cuff.

Said cuff may comprise an indicator of size of the connector upon which it is provided, or for a particular component or size of a component to be associated with the connector (optionally the component being a patient interface, such as a nasal cannula).

The cuff may be colour-coded as an indicator of a connector size or for a particular component or size of component to be associated with the connector (optionally the component being a patient interface, such as a nasal cannula).

The cuff may be dimensioned to transition from a substantially circular exterior surface contour form, when substantially abutting or substantially adjacent to or with an exterior surface of the outer wall of the connector, to a substantially square exterior surface contour form provided substantially (optionally wholly) about the first end of the connector body.

The body of the connector may comprise at least one recess or groove shaped to receive one or more splines on an inner surface of the cuff.

A swivel-type connector component may be, in use, connected the body of the connector.

The swivel-type connector may be configured to connect with the terminal end of a conduit, and the swivel-type connector is configured to connect with the body of the connector.

The connector may comprise at least one retaining protrusion, the retaining protrusion extending in a radially inward direction from the body of the connector.

The retaining protrusion may comprise one or both of:

- a ramped surface optionally ramped away from the first end of the body
- a surface substantially perpendicular to the inner wall of a body of the connector.

The connector may comprise at least one attachment arm.

The attachment may comprise the at least one retaining protrusion.

The at least one attachment arm may be cantilevered relative to the body of the connector to allow for flexibility of the attachment arm in at least a direction radial to the body of the connector optionally radially inward, outward or both.

The connector may comprise at least one cut-out region located around at least part of the attachment arm. The cut-out region promoting flexibility in a radial direction.

The connector may comprise a pair of attachment arms.

The attachment arm may be located within the recess or groove shaped to receive a spline on an inner surface of a cuff.

The body of the connector or the attachment arm may comprise a recess to receive part of said swivel-type connector component.

The swivel-type connector component may connect to the conduit via a thread.

The swivel-type connector may connect to the first end such that relative movement of the connector body and swivel-type connector is allowed rotationally, yet prevented axially.

The swivel-type connector may comprise a surface or surfaces which form(s) a rotatable seal with the inner surface of the connector body.

The or an external alignment feature(s) of the connector may be shaped or configured to:

- prevent connection of the internal connection features of the connector with another connector, when the external alignment feature(s) of the connector and an external alignment feature of another connector are in an unaligned orientation, and/or
- allow connection of the internal connection features of the connector with another connector, when the external alignment feature(s) of the connector and an external alignment feature of another connector are in an aligned orientation.

In a seventh aspect, there is provided a connector of the first or second aspects, wherein said another connector is configured to be engaged or engagable with the connector.

In an eighth aspect, there is provided a connector, wherein said connector is configured to be engaged or engageable with a second connector the second connector being defined by the connector of the first or second aspects.

The connector may seal with at least one of the following surfaces of the second connector:

- an external surface of the body,
- a side wall of a radially extensive flange or lip,
- an external surface of a cuff provided about the first end of the connector body.

In a ninth aspect, there is provided a connector to be provided at a terminal end of a breathing conduit, the connector comprising:

- a body, the body comprising a first end and a second end,
- the first end, in use, being engaged or engageable with the terminal end of the breathing conduit or at least a component to be associated with the terminal end of the breathing tube, and
- the second end, in use, to be engaged or engageable with a second connector, and
- wherein an internal surface of the body comprises one or more internal connection and/or alignment features configured for connection with said second connector which may be received internally therein, and
- wherein the one or more internal connection and/or alignment features comprise at least one of:
- a protrusion or rib projecting radially inward
- a recess projecting radially outward from a notional or actual internal wall or surface.

The alignment features may be configured to align the connector with second connector The connection features may be configured to facilitate connection between said connector and second connector.

The connection and/or alignment features may provide for, at least in part, sealing, or a sealing surface, between the connector and second connector.

At least one of the ribs or protrusions of the connector may be configured to match with corresponding recesses (for example recesses of a cuff or sleeve) second connector, and/or at least one recess of the connector is configured to match with corresponding ribs or protrusions of second connector The one or more internal connection and/or alignment feature(s) may be to be co-located or co-locatable for keying with a reciprocally shaped projection or recess of a portion of second connector The at least one of the ribs and/or recesses may be arranged circumferentially around the internal surface of the connector, optionally the ribs and/or protrusions are spaced equidistantly around the circumference of the internal surface of the connector.

There may be one or more or a plurality of ribs and/or recesses, optionally there are 2, or 3, or 4, or 5, or 6 ribs and/or recesses.

There may be 4 ribs.

The at least one protrusion or rib may extend in a substantially longitudinal direction along the internal surface of the body.

The at least one protrusion or rib may extend substantially from at or near a terminal end of the second end of the connector in a direction toward the first end of the connector.

At least one recess may be located in a side wall or an internal surface of the body of the connector, the at least one recess configured to accommodate an associated projection (s) of said second connector when said second connector is brought into a mating or connection with said connector.

The connector may be configured to provide at least a first internal surface for sealing upon an external part of a said second connector, when a connection or mating is made thereto by or with said second connector, the first internal surface is provided by a circumferential portion of the internal surface of the body, optionally said circumferential portion located at or near the second end of the body of the connector and provided so as to be substantially continuously and substantially circumferentially locatable about an external part of a said second connector to which the first internal surface is to be put into connection or a mating arrangement therewith.

The alignment or connection feature may form at least part of the first internal surface of the body The at least one protrusion or rib may form at least part of the first internal surface.

At least one protrusion or rib may extend in a substantially longitudinal direction along a side wall of the first internal surface.

The at least one protrusion or rib may extend substantially from at or near a terminal end of the second end of the connector in a direction toward the first end of the connector.

The first internal surface may be substantially curved when viewed in cross section The profile of the first internal surface (e.g. the radius of curvature and location of a curve of the first internal surface) may match an external profile (e.g. an external curve or curvature) of a cuff of a said second connector.

The at least one alignment or connection feature (optionally a protrusion or rib) is/are of a sufficient dimension so as to, in use, extend substantially to an outer-most apex of the external profile of the second connector.

The at least one alignment or connection feature (optionally a protrusion or rib) may be of a sufficient dimension so as to, in use, extend substantially to a position between the outer-most apex of the external profile of a cuff of the second connector and the end of the cuff nearest the terminal end of the second connector.

The at least one alignment or connection feature (optionally a protrusion or rib) may be of a sufficient dimension so as to, in use, extend substantially to a position between the outer-most apex of the external profile of a cuff of the second connector and the end of the cuff nearest the end of the second connector connected to a conduit.

The connector may be configured to provide a second internal surface for sealing upon when a connection or mating is made thereto by or with said second connector, the second surface defined by a substantially radially extensive flange or lip projecting radially inward from the internal surface of the body as a side wall surface, said side wall surface providing a face.

The face may be of a dimension sufficient to seal upon a respective face of a said second connector.

The face may be configured to provide for a substantially planar surface upon which a portion or a surface of a said second connector can mate or engage therewith.

The face may be oriented to substantially face toward said second end of said connector.

The face may be configured to mate or seal upon a side wall, or ledge, or lip or base, or end of a second connector.

The radially extensive flange or lip may comprise at least one of said internal connection or alignment feature.

The at least one connection or alignment feature may be a rib or protrusion

The face may comprise one or more internal connection and/or alignment feature(s), the internal connection and/or alignment feature(s) is/are to be co-located or co-locatable for keying with a reciprocally shaped projection or recess of a portion of second connector At least one recess may be located in a side wall or an internal surface of the connector, the at least one recess to accommodate projections of said second connector.

The recess may be a depression or other surface relief feature provided upon the face.

The depression or other surface relief feature may be a cut-out of the face.

The recess may be configured to accommodate or be receivable of an associated projection or other shaped feature of a said second connector when said second connector is brought into a mating or connection with said second internal surface.

At least one protrusion may be located in a side wall or an internal surface of the connector, the at least one protrusion to accommodate recesses of said second connector.

The connector may be configured to provide at least a third internal surface for sealing upon an external part of a said second connector, when a connection or mating is made thereto by or with said second connector, the third internal surface is provided by a circumferential portion of the internal surface of the body, optionally said circumferential portion located at or near the first end of the body, or at or near the second end of the body of the connector and provided so as to be substantially continuously and substantially circumferentially locatable about an external part of a said second connector to which the third internal surface is to be put into connection or a mating arrangement therewith.

The alignment or connection feature may form at least part of the third internal surface of the body The at least one recess may form at least part of the third internal surface.

The at least one recess may be shaped so as to accommodate projections of said second connector.

The recess may comprise a pair of shoulders, sloping away from each other and away from an end at the intersection of the shoulders, the end of the recess located substantially more toward the first end of the connector than the shoulders.

The at least one recess may be substantially tongue shaped, and/or substantially triangular and/or substantially tapers toward an end.

The recess may be a longitudinal channel.

The connector may comprise one or more sealing surface (s), the one or more sealing surface(s) defined by one or more of:

a first sealing surface as described above, a second sealing surface as described above, a third sealing surface as described above.

An adapter may be configured to facilitate connection between two connectors, wherein the connector of any of the first to ninth aspects is provided as part of the adapter.

A breathing conduit assembly, may comprise:

a breathing conduit, and a connector of any of the first to ninth aspects, wherein the connector is coupled to, or associated with, or associated to the breathing conduit.

The or an external alignment feature(s) of the connector may be shaped or configured to:

prevent connection of the internal connection features of the connector with another connector, when the external alignment feature(s) of the connector and an external alignment feature of another connector are in an unaligned orientation, and/or allow connection of the internal connection features of the connector with another connector, when the external alignment feature(s) of the connector and an external alignment feature of another connector are in an aligned orientation.

In a tenth aspect, there is provided a connector assembly, the connector assembly comprising a first connector and a second connector, the first connector for connection with the second connector, the first connector comprising:

a first connector body, the first connector body comprising a first end and a second end, the first connector body internally defining a lumen for the passage of gas therethrough between each of the first and second ends, the first end, in use, being engaged or engageable with a terminal end of a breathing conduit or a component to be associated with the terminal end of the breathing conduit, and the second end, in use, to be engaged or engageable with the second connector, and wherein an internal surface of the body comprises one or more internal connection features, and wherein an external surface of the body comprises one or more external alignment feature(s);

the second connector comprising:

a second connector body, the second connector body comprising a first end and a second end, the body internally defining a lumen for the passage of gas therethrough between each of the first and second ends, the first end, in use, being engaged or engageable with the terminal end of the breathing conduit or component to be associated with the terminal end of the breathing tube, and the second end, in use, to be engaged or engageable with the first connector, and wherein an internal surface of the body comprises one or more internal connection features an outer wall surrounding of the one or more internal connection features, the outer wall or at least an exterior surface of the outer wall comprising one or more external alignment feature(s);

wherein when the external alignment feature(s) of the first connector, and the external alignment feature(s) of the second connector are in an aligned orientation the internal connection features of the first connector, and the internal connection features of the second connector are oriented for connection.

When the external alignment feature(s) of the first connector, and the external alignment feature(s) of the second connector are in an unaligned orientation, the internal connection features of the first connector, and the internal connection features of the second connector are prevented from connection.

The first connector may be defined by the connector of the first and second aspects.

The second connector may be defined by the connector of any one of the third, fourth or fifth aspects.

The internal connection features of the first connector or the second connector may be male connection features and optionally comprise one or more (optionally a pair) of locking fingers.

The internal connection features of the first connector or the second connector may comprising one or more (optionally a pair) of locking fingers.

The first and/or second connectors may comprise one or more external visual aid(s) is/are configured for, in use, providing an externally visible guide for alignment of said connectors into an aligned connection therebetween.

An exterior surface of the outer wall of the first and/or second connector(s) may be tapered in a direction substantially longitudinally with the connector.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIG. 3 is a side view of the connector of FIG. 2, while

FIG. 28B1 shows a side view of the connector of FIG. 28A.

FIG. 28B2 shows a top view of the connector of FIG. 28A.

FIG. 33A shows how a body of a connector upon which a cuff is to be used may include a groove or other recess for receiving a spline or other projection of a cuff, while

FIG. 34A is another connector embodiment, shown as a perspective view, while

DETAILED DESCRIPTION OF PREFERRED EMBODIMENTS

Figure 1:
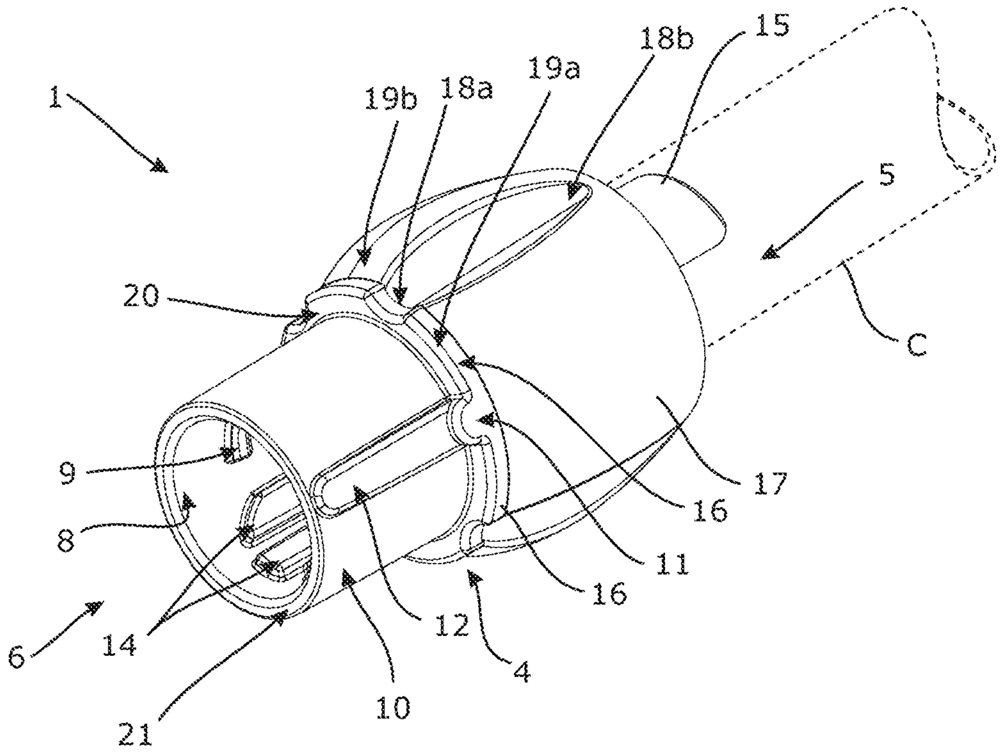
FIG. 1 is a perspective view of a connector from a second end (connector connecting end).

Provision of new and different connectors, particularly with a focus on improving useability as well as the correct alignment of connectors which are to be connected together, can improve patient safety in the successful and maintained delivery of gas therapies, such as delivery of humidified gas or other gas to a patient.

With reference to FIGS. 1-20, there is provided a connector 1 to be provided at a terminal end of a breathing conduit (indicated as C in the figures). The breathing conduit may be a medical breathing conduit. The connector 1 comprises a body 4 having a first end 5 and a second end 6. The body 4 itself internally defines a lumen 7 for the passage of gas therethrough between each of the first and second ends 5, 6. It will be appreciated that depending on the flow of gas through the lumen, the ends 5, 6 of the connector 1 may each be considered to be either upstream or downstream of the other end when placed into a breathing circuit, for example the direction of gas flow will determine whether an end 5 is fluidly upstream or downstream of the other end 6.

The first end 5, in use, being engaged or engageable with the terminal end of a breathing conduit 3 or at least a component to be associated with the terminal end of the breathing tube.

Figure 26:
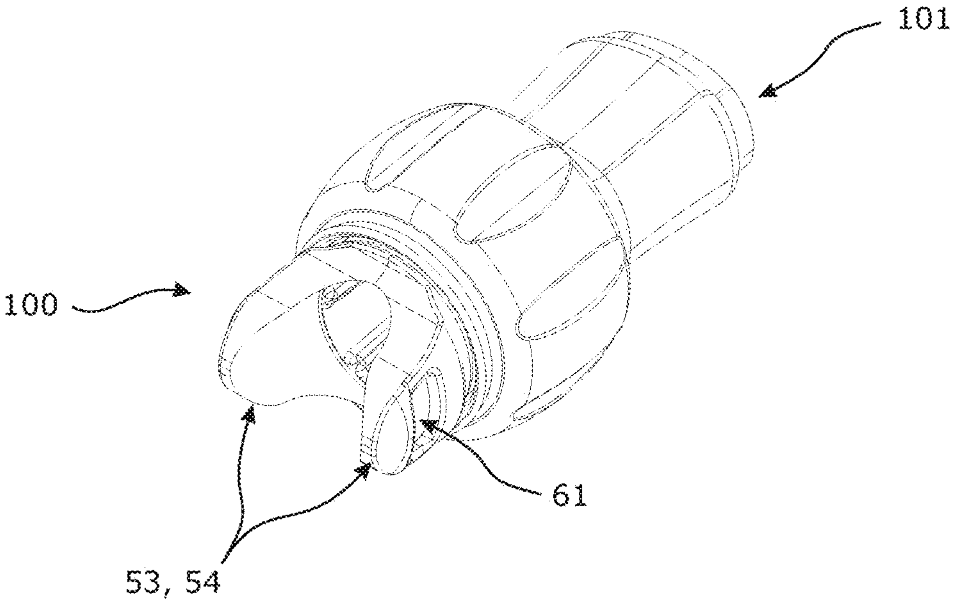
FIGS. 26-27 show a known connector having male connecting features in the form of a pair of locking fingers, such a connector able to be brought into engagement with the connector of FIG. 1 in a similar manner to that shown by FIGS. 21-23.
Figure 27:
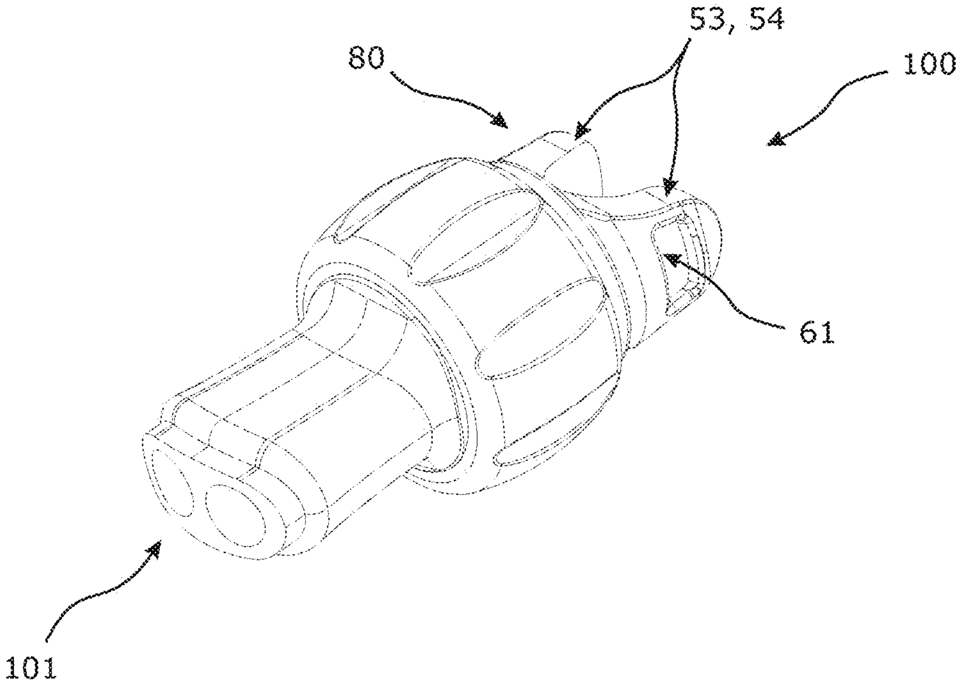
Figure 30:
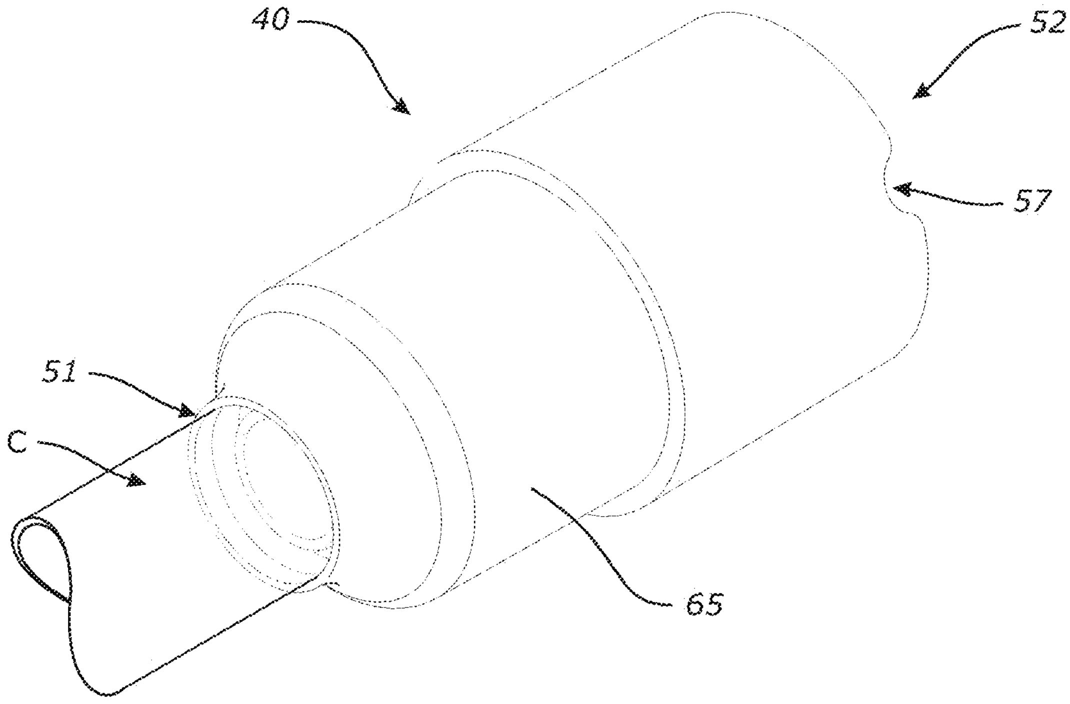
FIG. 30 is a cross-section of another connector embodiment, additionally illustrating a swivel-type arrangement in combination with a cuff arrangement.
Figure 31:
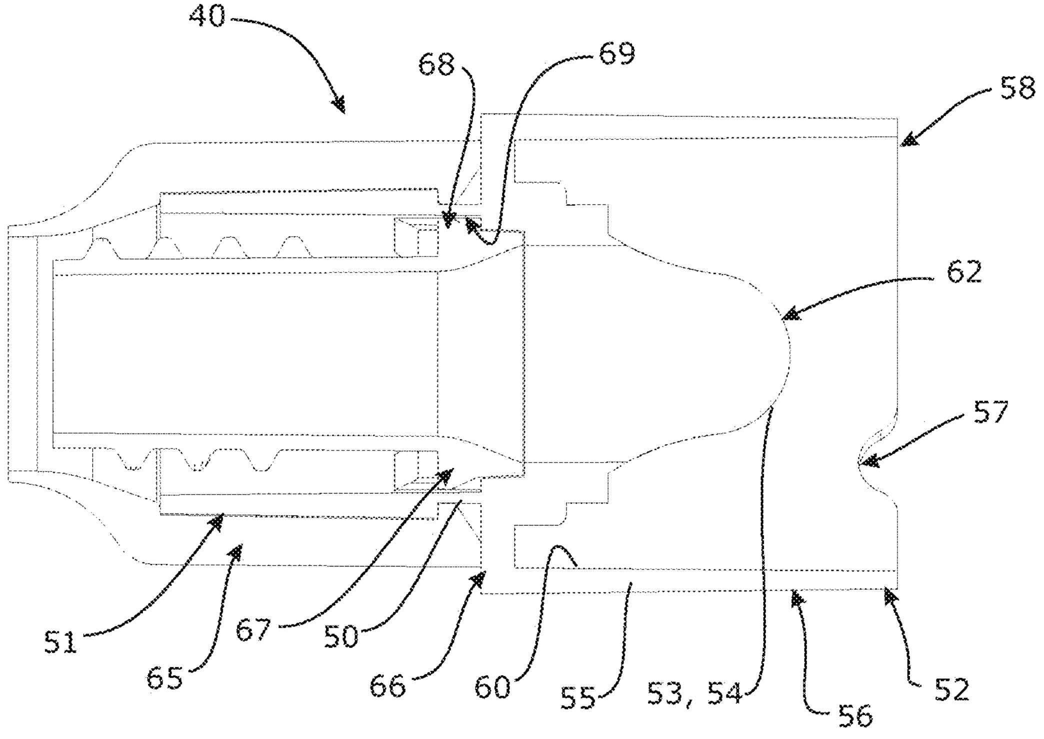
FIG. 31 is an external perspective view of the connector of FIG. 30.

The second end 6 of the connector 1 is, in use, to be engaged or engageable with another connector. For example, in various preferred embodiments, the second end 6 of connector 1 may be put into engagement with a suitably configured end of another connector. Suitably configured other connectors as shown herein are illustrated by:

- the second end 52 of a connector 200 (see for example FIGS. 21-25),
- the second end 100 of a connector 80 (as shown in FIGS. 26, 27) which provides for a pair of male connection fingers 53 in the form of a pair locking fingers 54 (such a connector 80 is already known from PCT/NZ2012/000142 published as WO 2013/022356 to the common applicant, Fisher & Paykel Healthcare Limited, the contents of which are incorporated herein),
- the second end 5 of a connector 40 (as shown in FIGS. 30, 31)

An internal surface 8 of the body comprises one or more internal connection features 9 configured for connection with another connector which is to be, in use, received internally.

An external surface 10 of the body 4 comprises one or more external alignment feature(s) 11 configured for aligning said connector or another connection into an externally aligned connection therebetween. Optionally, or in addition, there may be one or more external visual aid(s), at least a part of which may form the item indicated as 12 that are configured for providing an externally visible guide for alignment of the connector 1 or another connector (for example the recess or cut out 57 of the connectors labelled as 200, 40) into an aligned connection therebetween. Such visual aid(s) may also be configured to provide dual function as an alignment feature. For example, a visual aid can be of a sufficient bulk or tapered dimension so as to transition from being a visual aid to being an alignment feature itself.

The one or more connection features 9 is/are surface feature(s) that extend radially inward from the inner surface 8 of an internal side wall of the body 4.

The one or more internal connection features 9 can be one or more tabs, where a tab is a raised protrusion extending from the inner surface 8.

In particular embodiments, the connection features 9 can be oriented so as to be radially aligned with respective external alignment features 11 and/or the corresponding external visual aids 12.

Although the figures show a pair of connection features 9, it will be appreciated further connection features may be provided about the inner surface 8.

In order to facilitate relative ease of assembly, at least one of the connection features 9 may include a longitudinally extensive channel or recess 13, or the connection feature may be split into two more parts to allow for such a channel or recess 13 (or slot). Such a channel or recess 13 is configured to locate, retain, or position a printed circuit board (PCB) arrangement (not shown) which may be inserted into such a slot. It will also be appreciated that a channel or recess 13 (or slot) may be provided at other locations about the inner surface 8.

In order to facilitate ease and improved or correct connection by another connector with the connection features 9, the internal surface 8 can include one or more internal alignment features 14. Such internal alignment features are configured for aligning a connection feature of another connector (e.g. one or more male lock fingers that may extend into the internal space of the body 4) that is placed in contact therewith, for example when the connector feature of another connector is inserted into or is received internally of the body 4 at the second end. In such a mode, the connection feature of another connector is oriented (such as by being rotated) to be brought into an aligned connection orientation with the internal connection features 9 of connector 1. For example, the internal surface 8 has the one or more internal alignment features 14 configured to, in use, rotatably orient a male connection feature of another connector into an aligned connection orientation for connection with the connector, or at least into connection with one or more of the internal connection features 9 located on or about the internal or inner surface 8 of the body 4.

It will be appreciated the internal alignment feature(s) 9 may be surface feature(s) that extend in a radially inward direction from the surface of an internal side wall of the body 4, or the inner surface 8. The internal alignment feature(s) may be of the form of one or more tab(s), where a tab is advantageously a raised protrusion.

Each tab may be shaped so as to provide a pair of shoulders, each shoulder sloping away from each other and away from an end (for example an apex, or rounded apex, or a flat or curved surface, such as that shown by FIGS. 1A, 2A, 17, 20) at the intersection of the shoulders. Such an end of the shoulders being located substantially more toward a terminal end of the second end of the connector. In this manner, such a tab can guide or encourage a male connection feature that comes into contact with the shoulders to slide down the slope of each shoulder, thereby being auto-rotated.

In an alternative, the internal alignment feature(s) 14 may be one or more ribs extending substantially in a longitudinal direction of the connector 1, and along the internal surface 8. Optionally, there may be any number of ribs, but for example there may be: 1-10 ribs, or 2-8 ribs, or 4-6 ribs, or 2 ribs, or 3 ribs, or 4 ribs, or 6 ribs, or 8 ribs, or 10 ribs. In particular, there may be two sets of such ribs, each set comprising of 3 such ribs.

There could also be two or more sets of internal alignment features 14 provided on or about the internal surface 8 of the body 4, although most advantageously there may be two sets of such alignment features (which may be generally circumferentially opposing).

Where a set of internal alignment features 14 are to be provided, each set may have an equal (i.e. same) number of such internal alignment features as another set.

In one preferred embodiment, there is a pair of internal alignment features 14, that in use, rotatably align a pair of fingers (i.e. male locking fingers) that extend from another connector when inserted into or placed into engagement or surface contact with said internal surface of the connector 1.

As previously discussed, the first end 5 is configured for engagement with the terminal end of a breathing conduit. Such a first end can include a sleeved portion 15 to be attached to the terminal end of the breathing conduit, with which a suitable connection, such as a pneumatic connection can be made. At least a part of the sleeved portion 15 is configured to be insertable into or to be located or housed within an interior surface of the lumen of the terminal end of the breathing conduit (i.e. an internal connection is made), or alternatively the sleeved portion may be receivable upon or to be located or housed upon an exterior surface of the terminal end of the breathing conduit (i.e. an external connection is made).

Turning to the external alignment feature(s) 11 and/or the external visual aid(s) 12, these can be external surface features which extend radially outwardly from the outer surface 10 of an external side wall of the body 4. For example, these may be in the form of a tab or raised protrusion.

In one configuration, the external alignment feature(s) 11 or visual aids 12 may include one or more ribs extending substantially in a longitudinal direction with the connector and along the external surface 10 of the body 4. For example, there may be any number or ribs, although particularly preferred may be: 1-10 ribs, or 2-8 ribs, or 4-6 ribs, or 2 ribs, or 4 ribs, or 6 ribs, or 8 ribs, or 10 ribs.

Figure 2:
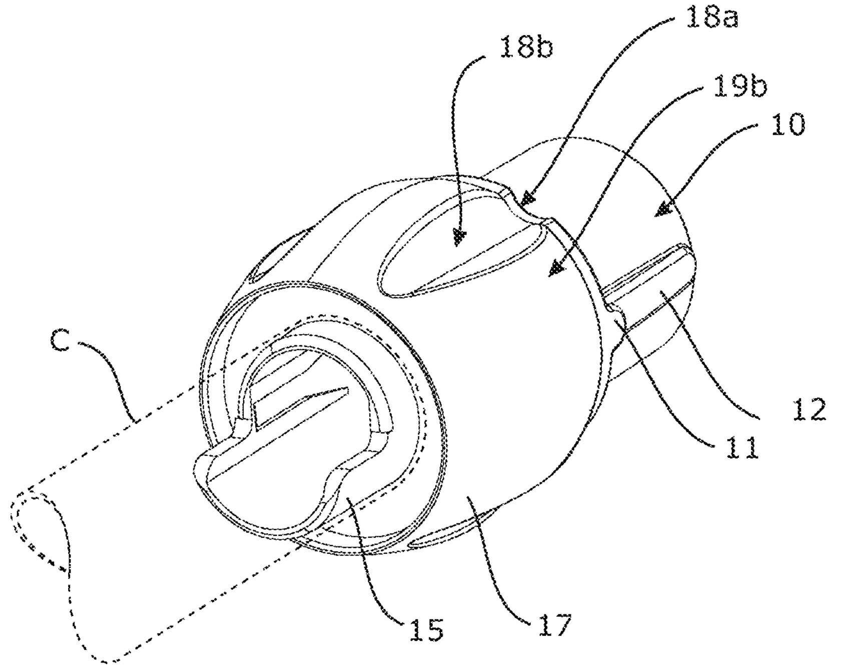
FIG. 2 is a perspective view from the other end of the connector of FIG. 1.
Figure 1A:
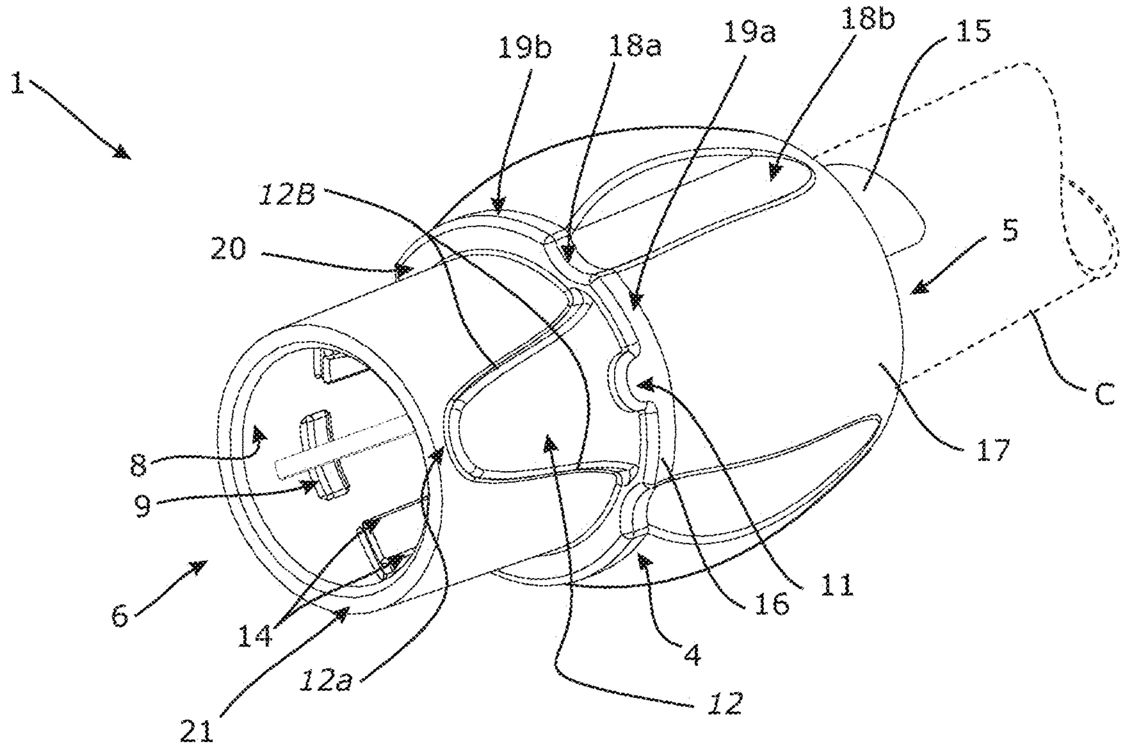
FIG. 1A is a perspective view of a connector from a second end (connector connecting end).
Figure 2A:
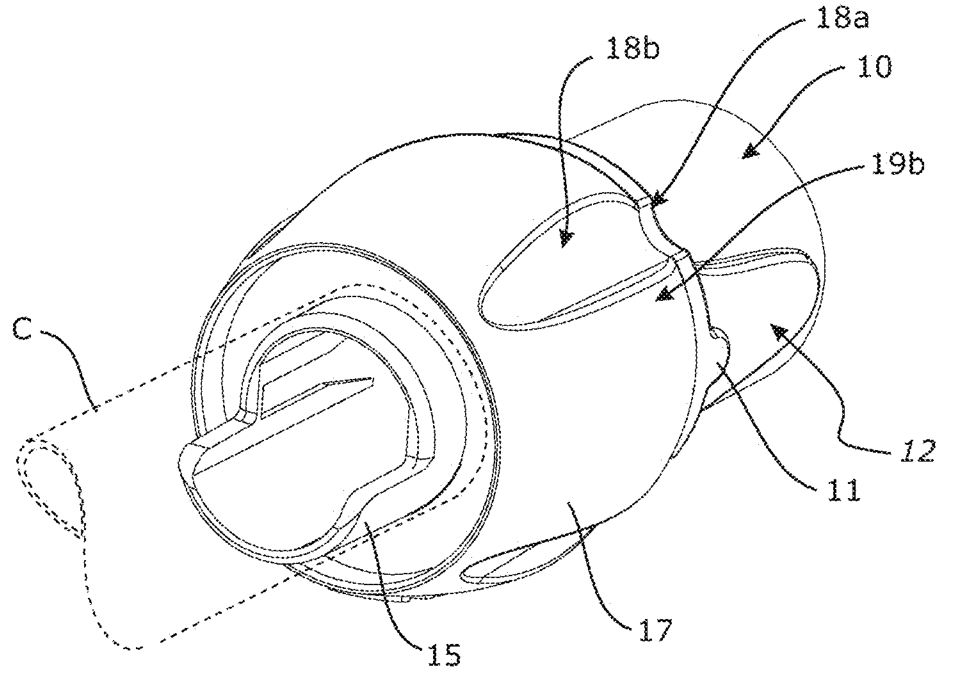
FIG. 2A is a perspective view from the other end of the connector of FIG. 1A.

FIGS. 1A and 2A show an alternative configuration of the external visual aid(s) 12 of the connector. The external visual aid(s) 12 comprise a raised protrusion with an end 12A (for example an apex, or rounded apex, or a flat or curved surface) and a pair of shoulders 12B. The shoulders 12B are arranged to slope away from each other and away from an end at the intersection of the shoulders. The end 12A is located toward a second end 6 of the connector, and the shoulders are located nearer the first end 5 of the connector (than to the second end 6), for example near the flange or lip 16.

The external visual aid(s) 12 may optionally be substantially tongue shaped, and/or substantially triangular and/or substantially taper toward an end.

Figure 2B:
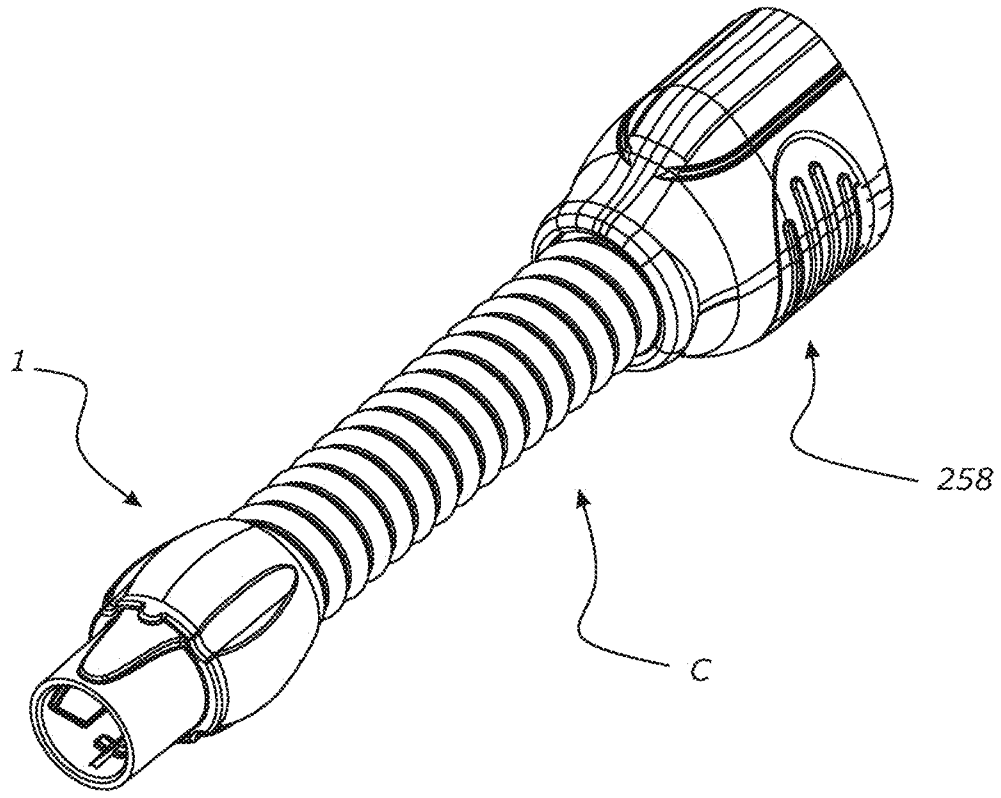
FIG. 2B shows the connector of FIGS. 1A and 2A as part of an assembly with a conduit and another connector.

FIG. 2B shows an assembly comprising the connector 1, a conduit C, and another connector 258. The another connector 258 may, for example, be the connector as described in U.S. Ser. No. 62/252,149 and/or U.S. Ser. No. 10/452,448 (as U.S. Pat. No. 6,953,354) to the common applicant, Fisher & Paykel Healthcare Limited, the contents of both of which are incorporated herein.

Figure 15:
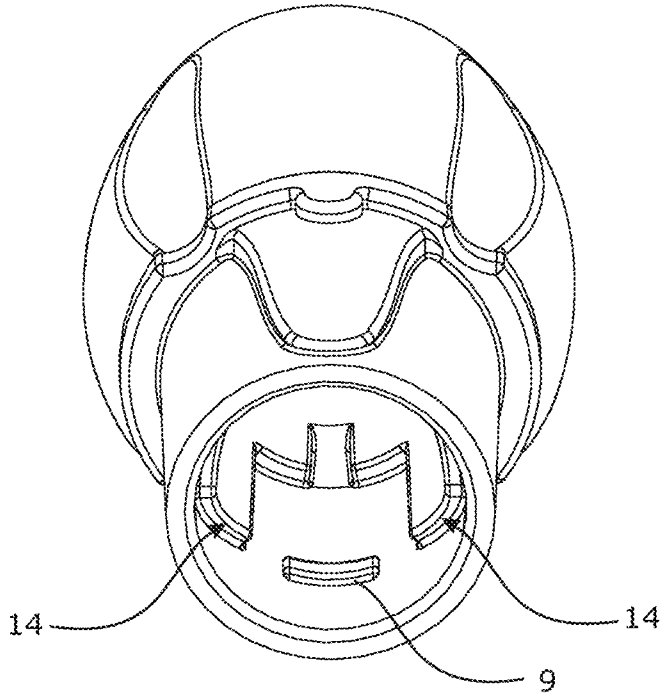
FIGS. 15 and 17 illustrate the same views as FIGS. 14 and 16, yet with respect to the connector of FIGS. 1A and 2A
Figure 16:
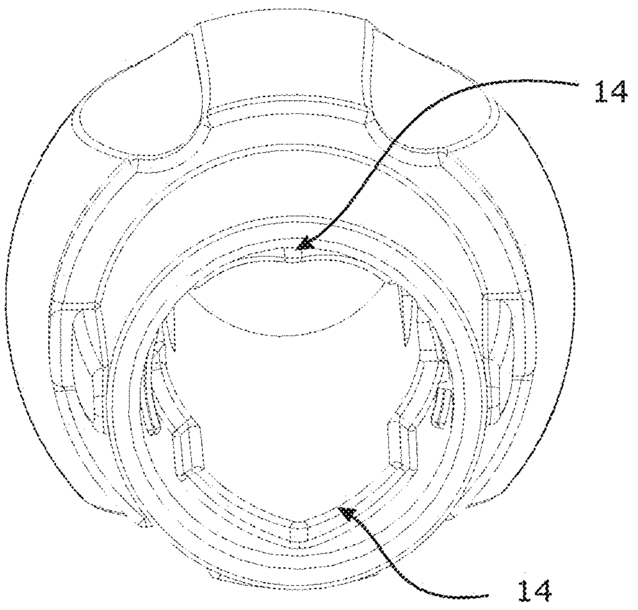
Figure 17:
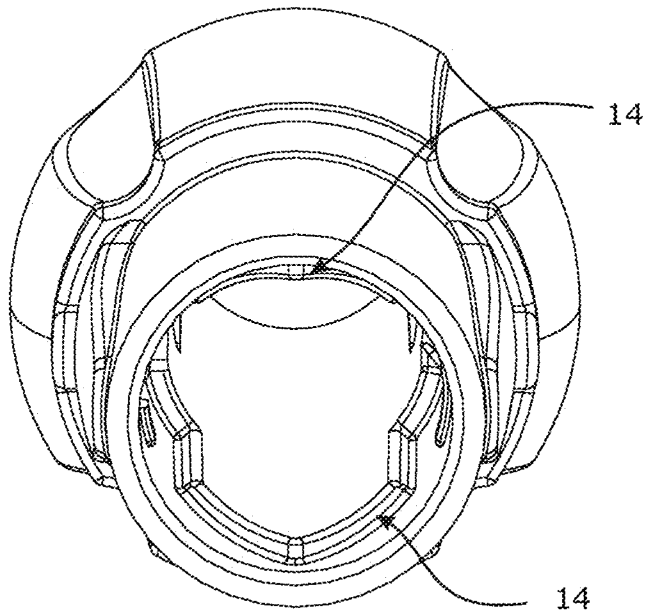
Figure 18:
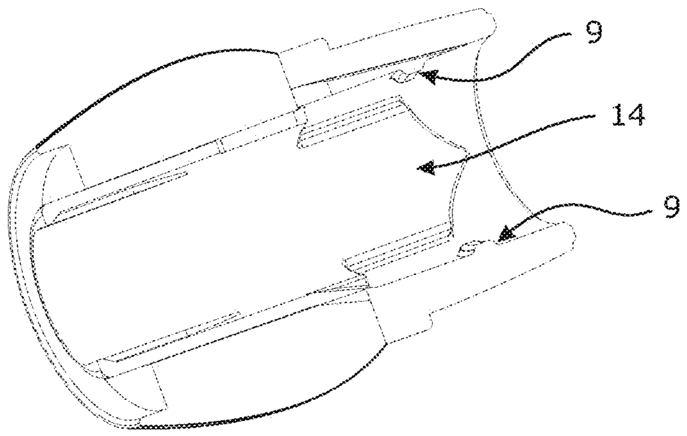
FIG. 18 is a cross-section through the connector of FIG. 11 showing internal features.
Figure 19:
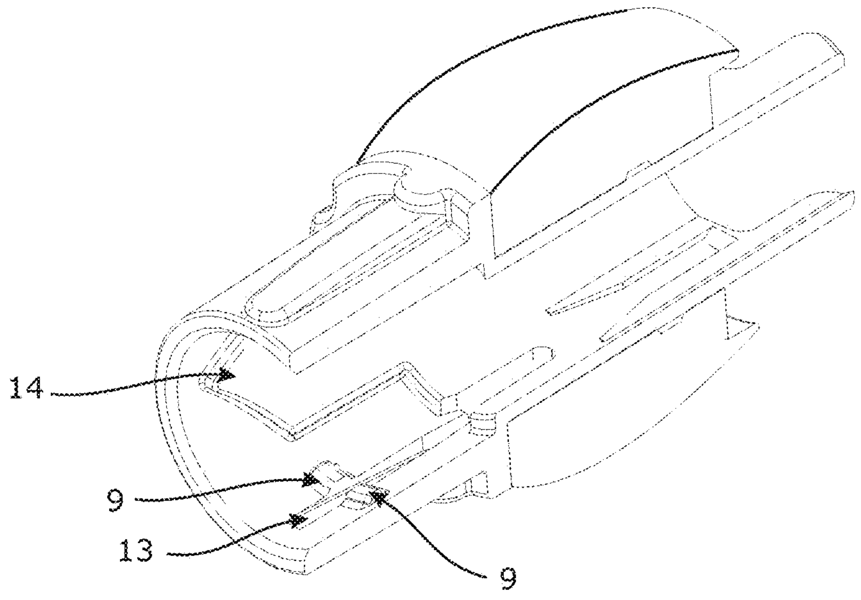
FIG. 19 is another sectional view through the connector of FIG. 11.

FIGS. 15 and 17 show end views of the connector of FIGS. 1A and 2A.

Figure 20:
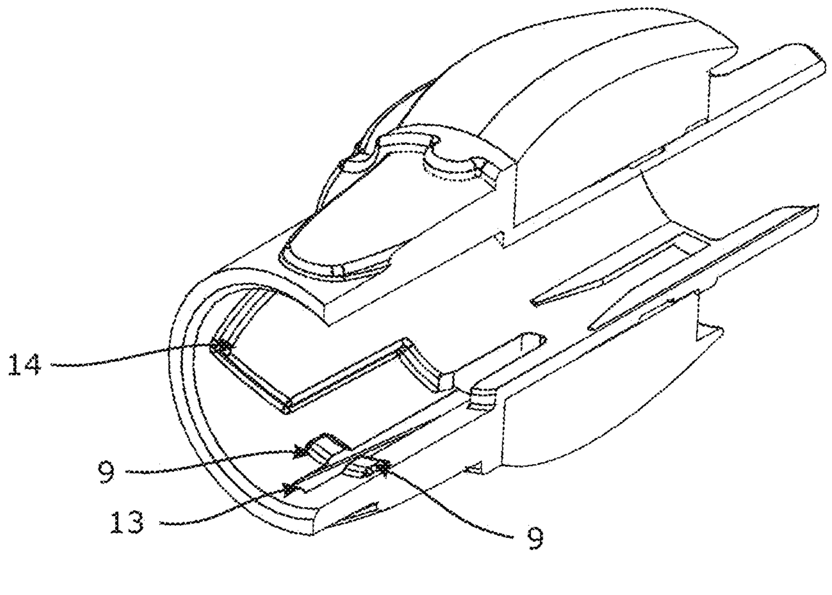
FIG. 20 is a sectional view through the connector of FIGS. 1A and 2A.
Figure 21:
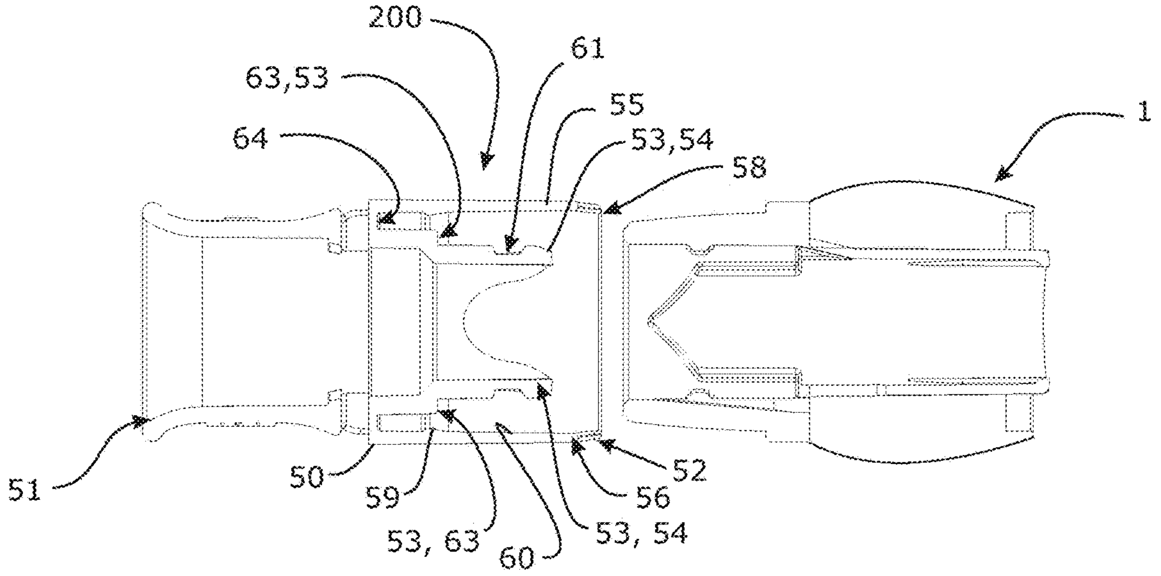
FIGS. 21-23 illustrate a sequence in which the connector of FIGS. 11, 12, 13, 14, 16 and 19 is connected or engaged with another connector (being the connector illustrated by FIGS. 28-29).
Figure 22:
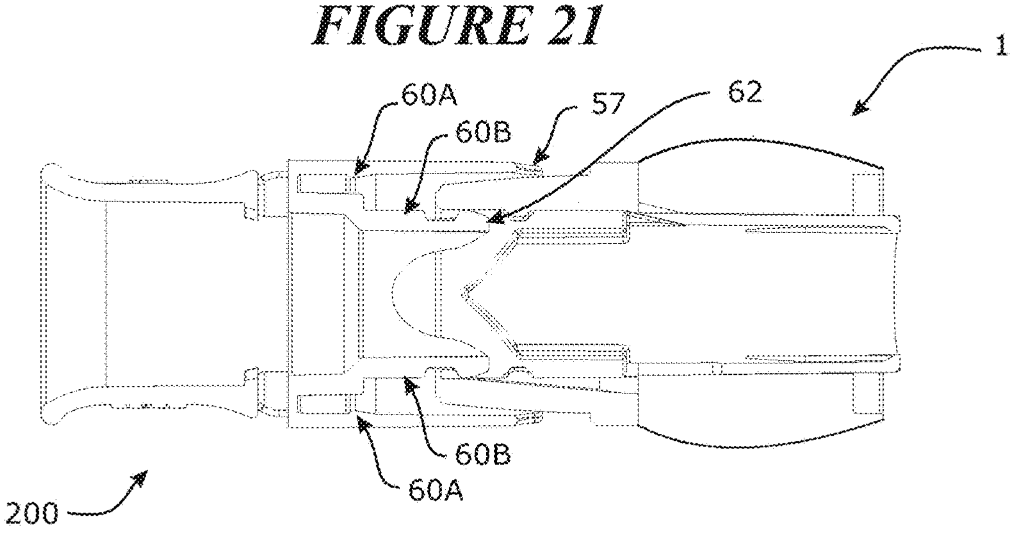
Figure 23:
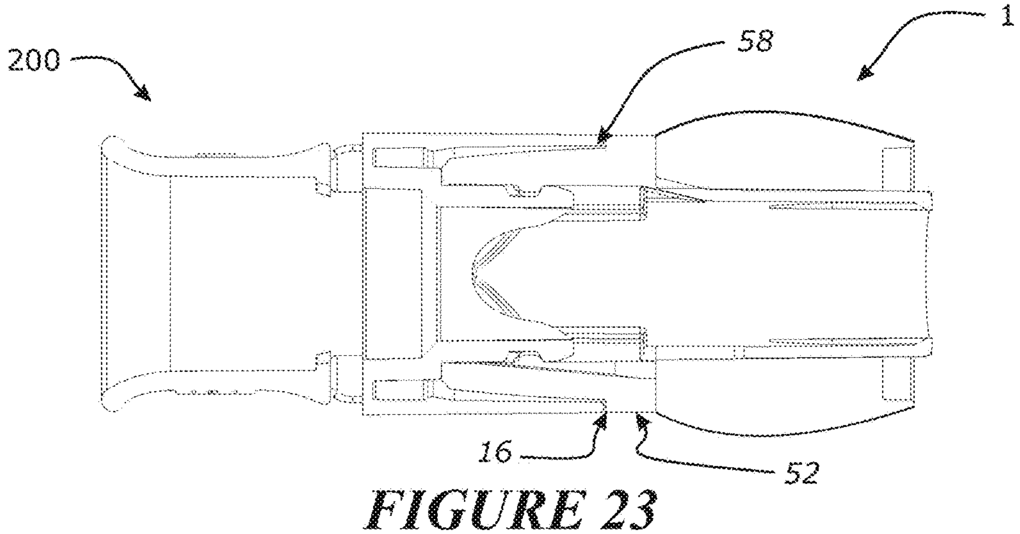
Figure 24:
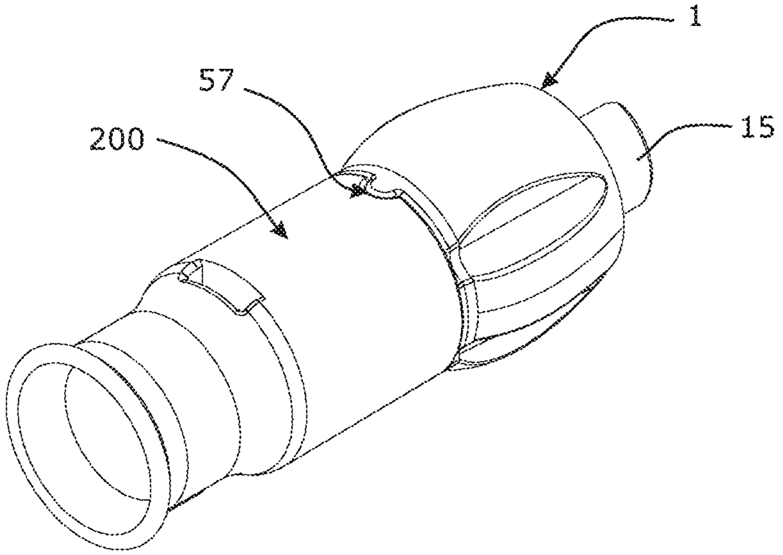
FIG. 24 shows a perspective view of the engagement made by the connectors shown in FIGS. 21-23.
Figure 25:
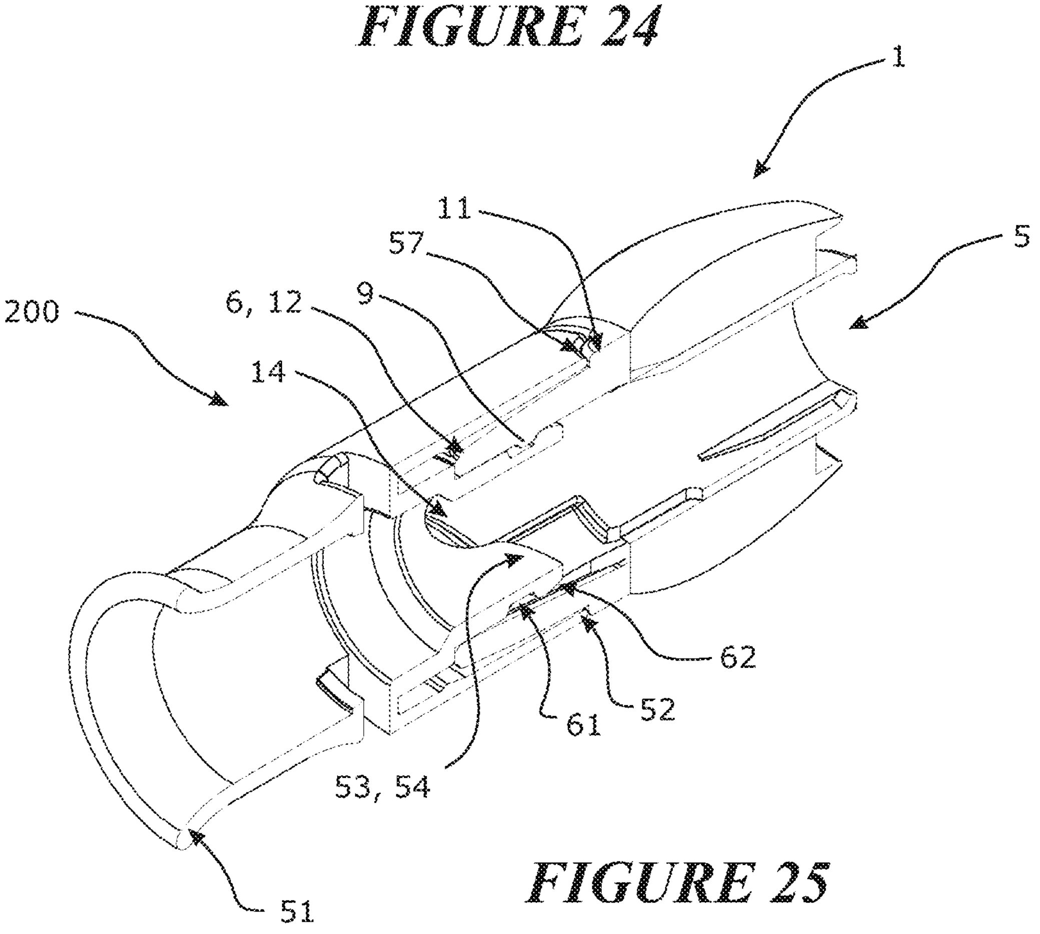
FIG. 25 shows a cross-section of the inter-connecting features of the engagement when made shown by FIGS. 21-23.

FIG. 20 shows a cross-section of the connector of FIGS. 1A and 2A.

The external alignment features (and/or visual aids) can be spaced, arrayed or arranged evenly or equidistantly from each other about the circumference or a radius of the external surface 10.

In another configuration, the external alignment feature 11 and/or visual aid 12, may be a projection of a length that extends in a substantially longitudinal direction of the connector and along the external surface 10, with a height of the projection from the external surface varying along its length. For example, the height of the external alignment feature and/or visual aid can taper along this length.

Where a taper is provided, the height of the projection may taper either so the height:

a. reduces in a direction extending from a base of the external alignment feature toward a terminal end of the second end of the connector, or b. increases in a direction extending from a base of the external alignment feature toward a terminal end of the second end of the connector.

Figure 3:
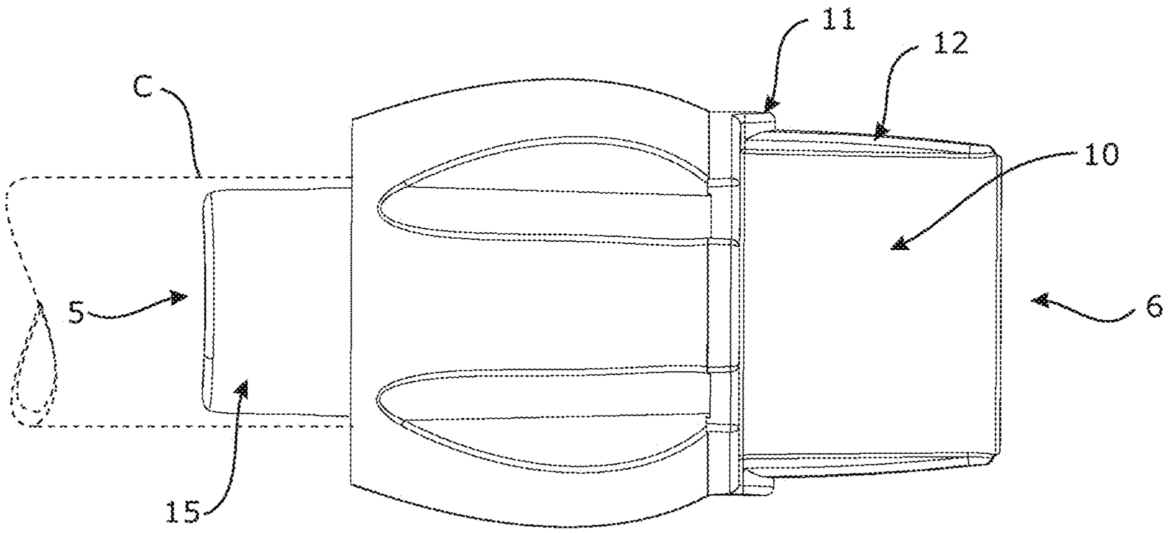
Figure 4:
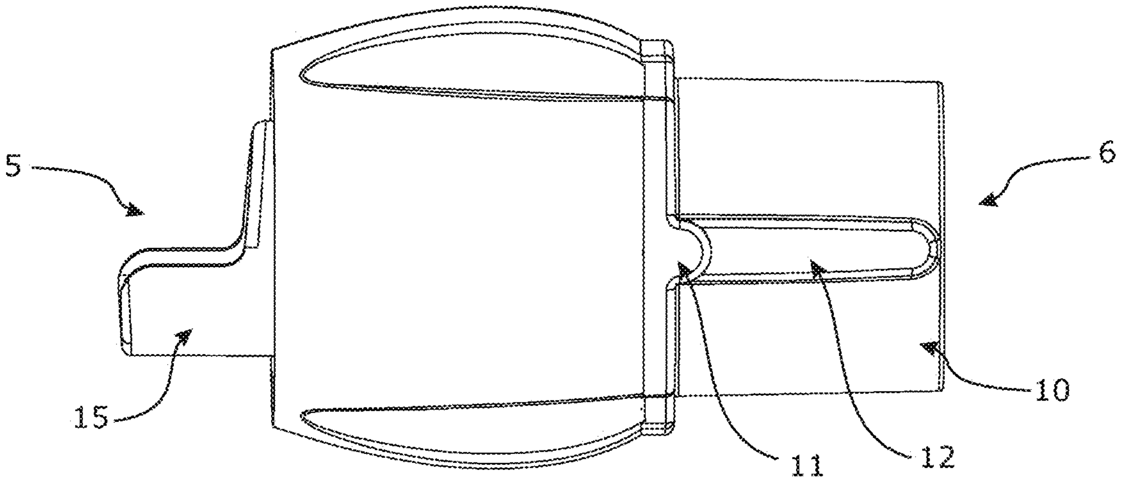
FIG. 4 is another side view where the connector has been rotated through 90°.
Figure 5:
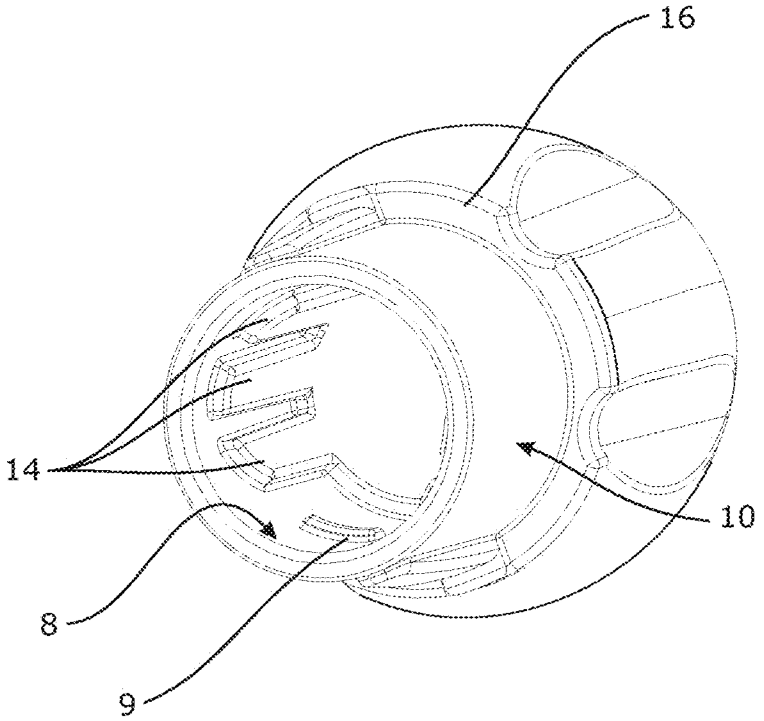
FIGS. 5-7 are each different views showing the interior of the second end of the connector of FIG. 1.
Figure 6:
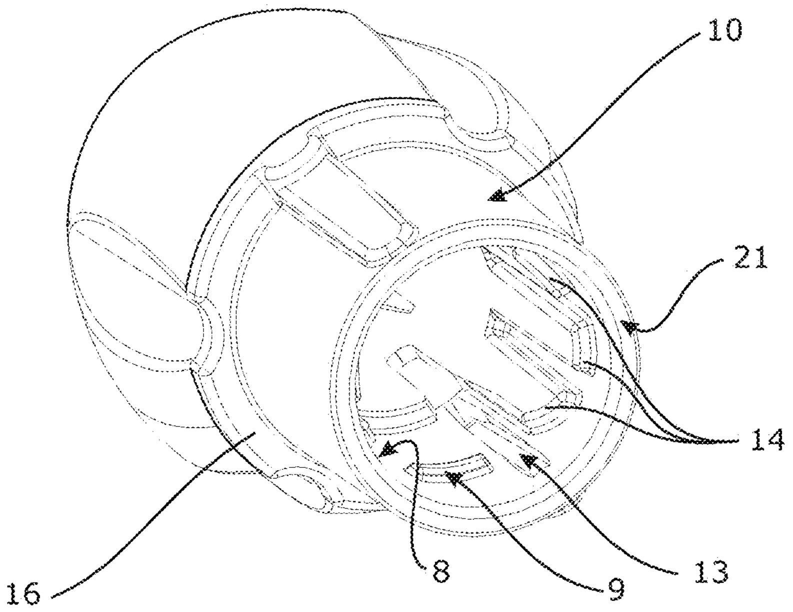
Figure 7:
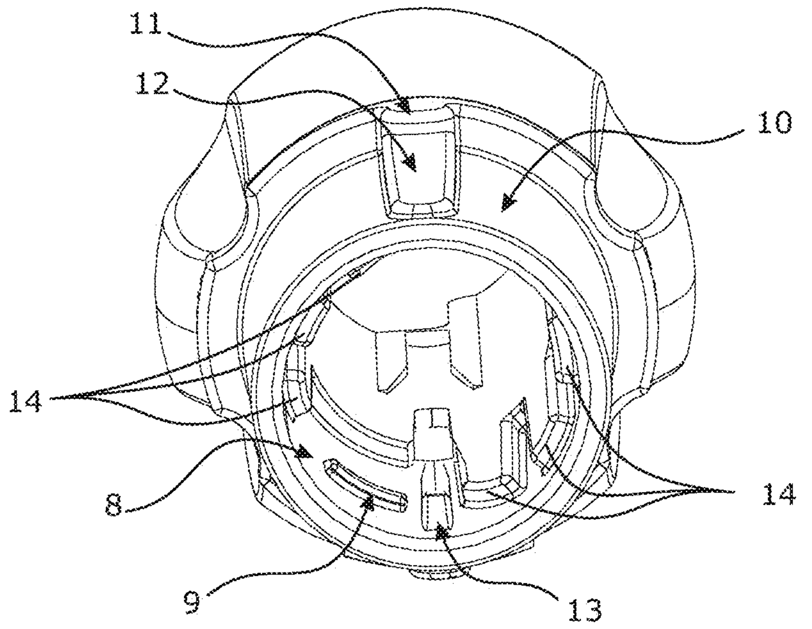
Figure 8:
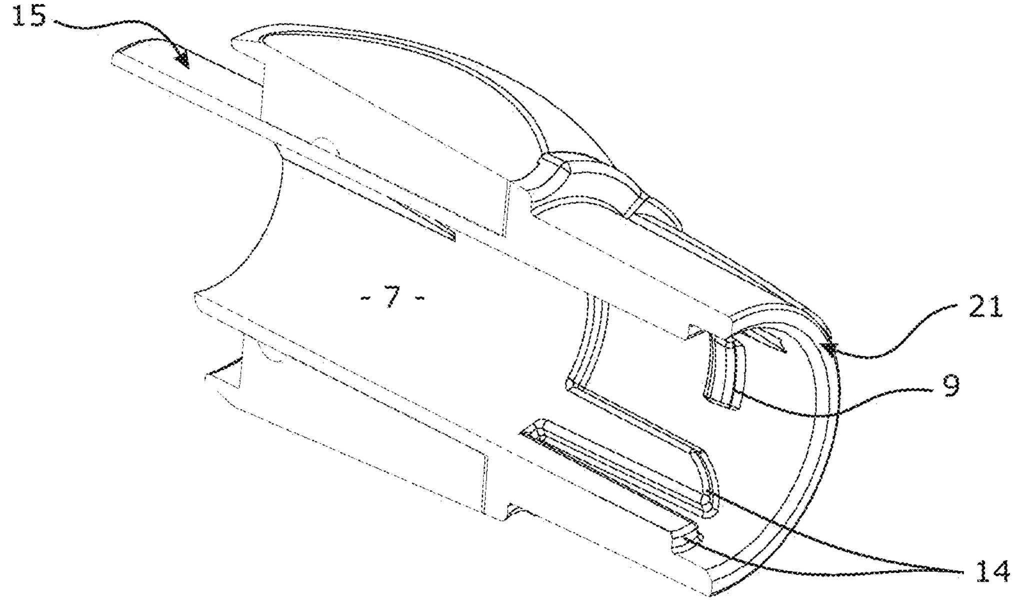
FIG. 8 is a cross-section through the c centre or mid-line of the connector of FIG. 1.
Figure 9:
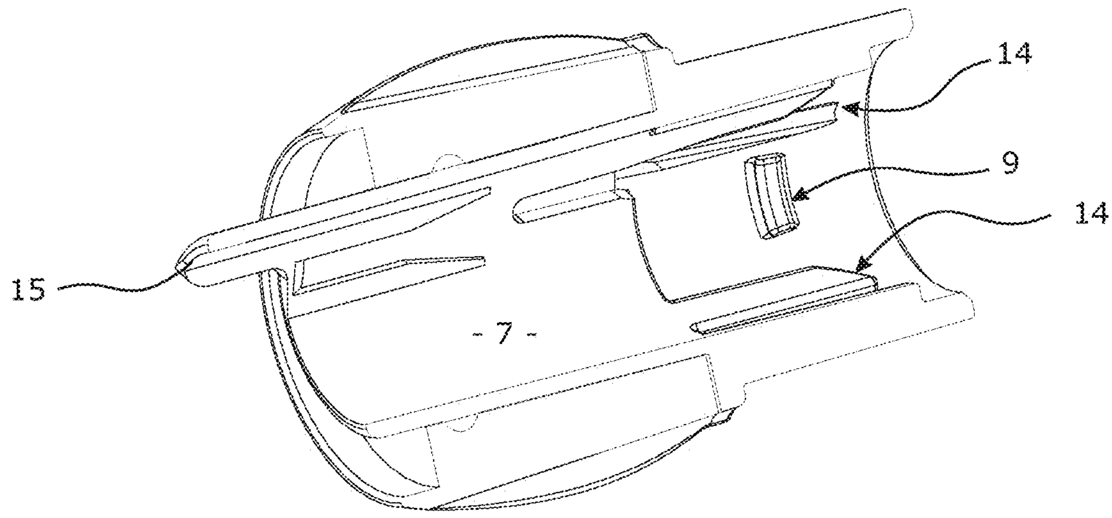
FIG. 9 is another cross-section of the connector of FIG. 1, axially rotated relative to FIG. 8.
Figure 10:
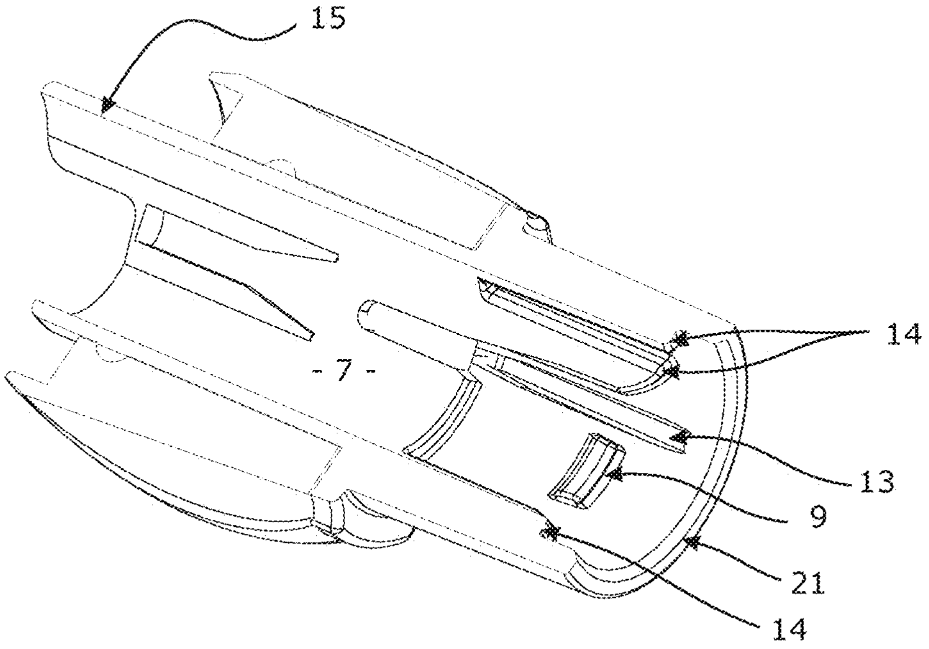
FIG. 10 is yet another cross-section of the connector of FIG. 1, axially rotated relative to FIGS. 8 and 9.
Figure 11:
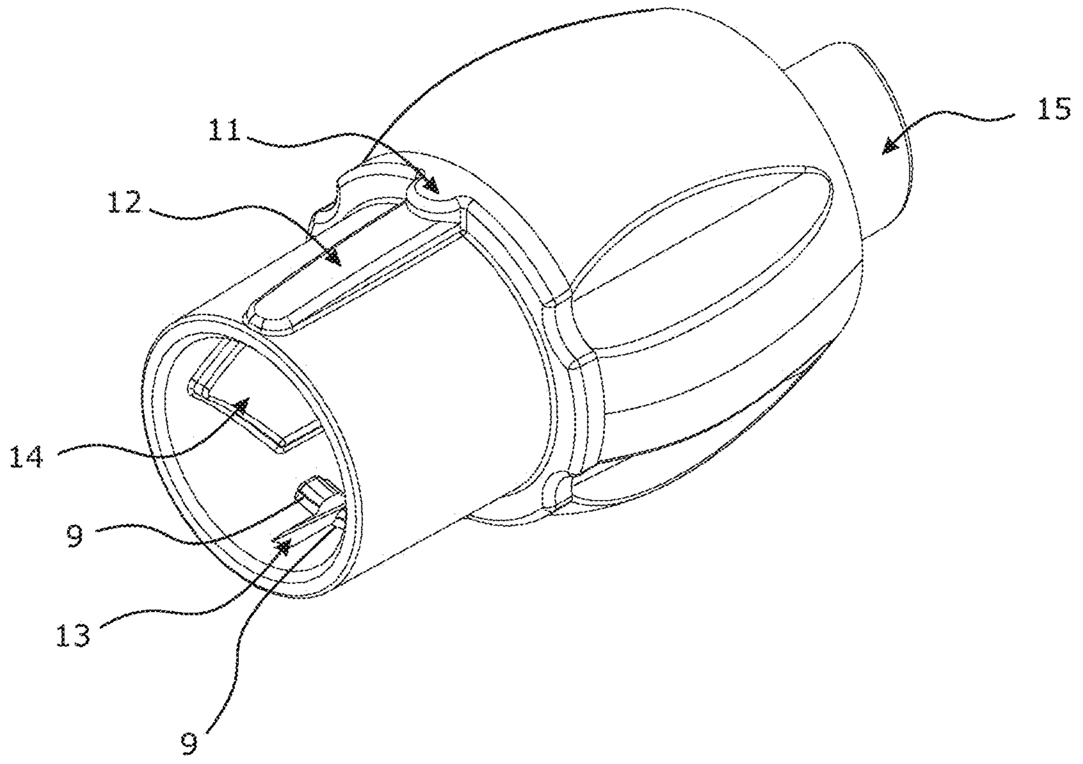
FIG. 11 is a perspective view of an alternative embodiment connector to that of FIG. 1.
Figure 12:
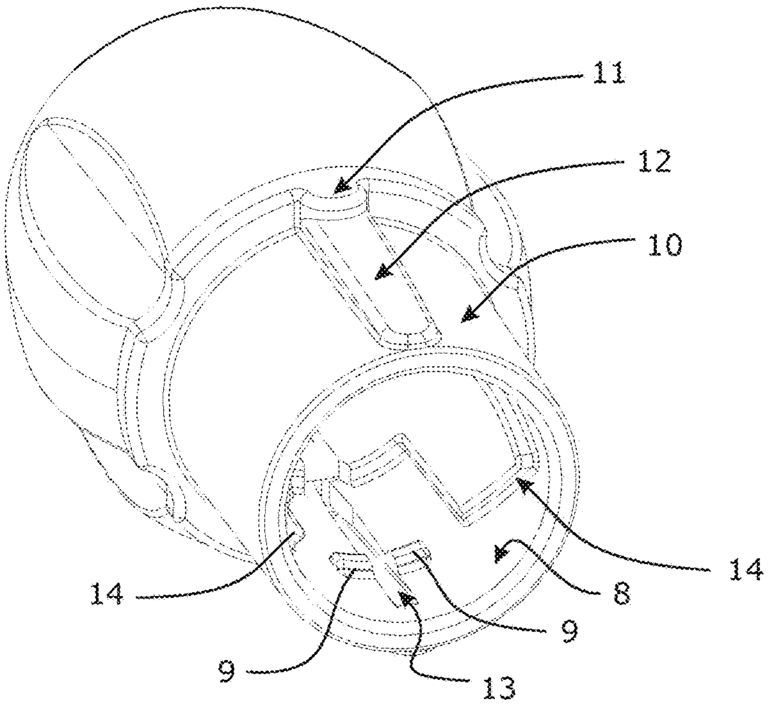
FIGS. 12, 13, 14, and 16 are different views of the second end of the connector of FIG. 11.
Figure 13:
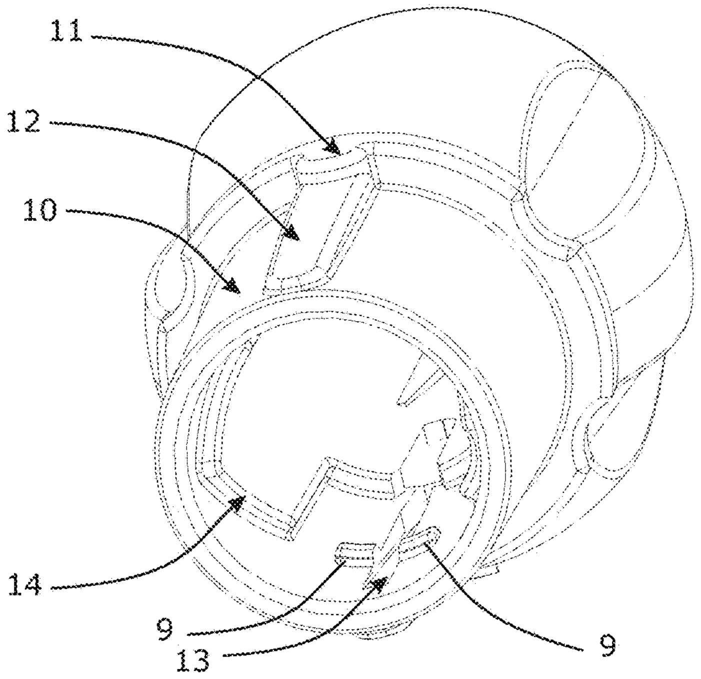
Figure 14:
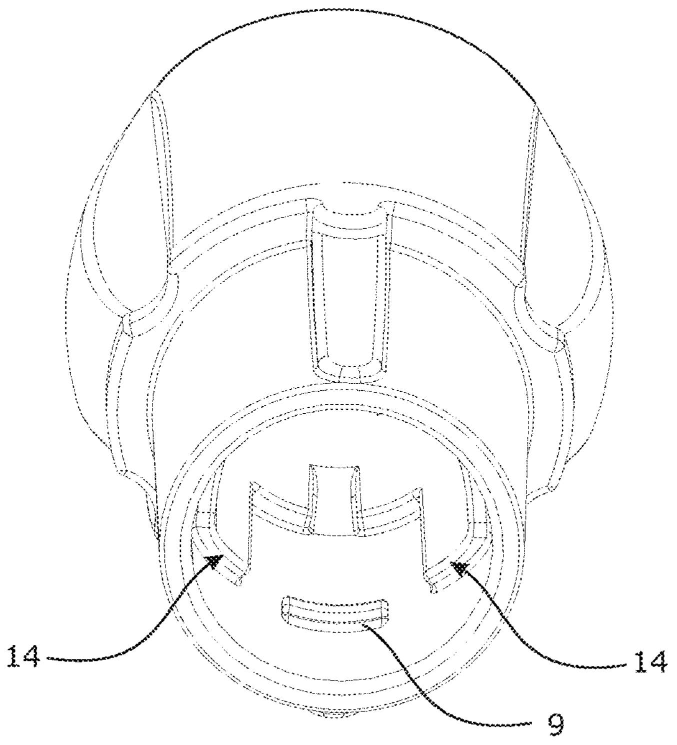

FIG. 3 in particular illustrates a tapered arrangement matching a) above (i.e. a taper that reduced in height as the projection progresses toward the terminal end of the second end 6).

In other configurations, provided substantially at or toward a base of a or each external alignment feature is a stepped protrusion that may form the external alignment feature identified as item 11 in the figures. The stepped protrusion being a more radially outwardly extending projection than an adjacent portion of the external alignment feature.

The stepped projection can be configured to co-locate or provide for co-location of a suitably shaped part which may be keyed therewith. The stepped projection allows for keying with a reciprocally shaped recess or cut-out of at least a part of a sleeved portion of another connector when brought to bear or into contact for connection between the connector 1 and another connector.

In an alternative, provided substantially at or toward a base of a or of each external alignment feature is a recess or cut-out, the recess or cut-out configured for receiving a protrusion or projection of a reciprocally shaped portion of another connector. Such an arrangement allows for the reciprocal type keying as mentioned above. In such a situation, the recess or cut-out can be configured to be co-located or co-locatable for keying with a reciprocal protrusion or projection of at least a part of a sleeved portion of another connector. Such a recess or cut-out effectively acts as a keyway for a key which may be brought to bear upon it.

Various shapes or profiles for the key or keyway may be used. It will be appreciated any suitable shape can be employed, although particularly preferred shapes or profiles include: semi-circular, triangular, rectangular or other recti-linear or geometric shapes, elliptical, wedge shapes.

The connector 1 may further comprise of a radially extensive flange or lip 16 that projects outwardly or away from the external surface 10 of the body 4.

Such a flange or lip 16 may effectively define a stop end for a point or length of maximum engagement by another connector when made with the external surface 10 of the connector 1. The flange or lip may optionally also provide for a sealing surface upon which another connector may make substantially a pneumatic connection therewith.

The flange or lip 16 may additionally comprises one or both of: 1) one or more radially and/or longitudinally recessed or grooved regions 18*a*, or 2) one or more radially and/or longitudinally extending projection regions 19*a*.

The flange or lip 16 may also be sufficiently longitudinally extensive so as to be configured for an engagement with the terminal end of the breathing conduit, or a component to be associated with the terminal end of the breathing conduit.

The external alignment feature(s) 11 of the connector 1 may be shaped or configured to prevent connection of the internal connection features 9 of the connector with another connector (for example connector 40), when the external alignment feature(s) of the connector 1 and an external alignment feature of another connector (for example connector 40) are in an unaligned orientation.

Additionally or alternatively the external alignment feature(s) 11 of the connector 1 may be shaped or configured to allow connection of the internal connection features 9 of the connector with another connector (for example connector 40), when the external alignment feature(s) 11 of the connector 1 and an external alignment feature of another connector (for example connector 41) are in an aligned orientation.

Optionally, a sheath 17, such as an overmoulding, may surround or provide for an engagement (whether pneumatic or not) about an external surface of the body 4. Such a sheath 17 may be provided for the one or more radially and/or longitudinally recessed or grooved regions 18*b*, and/or the one or more radially and/or longitudinally extending projection regions 19*b*.

The various recessed or grooved regions 18*b* and/or said extending projection regions 19*b* of the sheath may be wholly or at least partially aligned with the recessed or grooved regions 18*a* and/or said extending projection regions 19*a* of the flange or lip 16.

In still further configurations, an internal surface 8 of the body 4 can provide for, toward the second end 6 of the connector 1, the locating, retention, or positioning of a printed circuit board (PCB) arrangement. For example a PCB may be provided upon a relatively planar plate and may be inserted within the body 4. The PCB may be used for various reasons, may in some particular configurations facilities circuitry for: control, sensing (e.g. temperature, humidity, flow rate), heating (e.g. heater wires) or other electronic components for a breathing conduit to be used as a part of a breathing circuit.

The connector 1 may provide for a sealing surface upon which separate connections with separate other connectors may be made.

Figure 29:
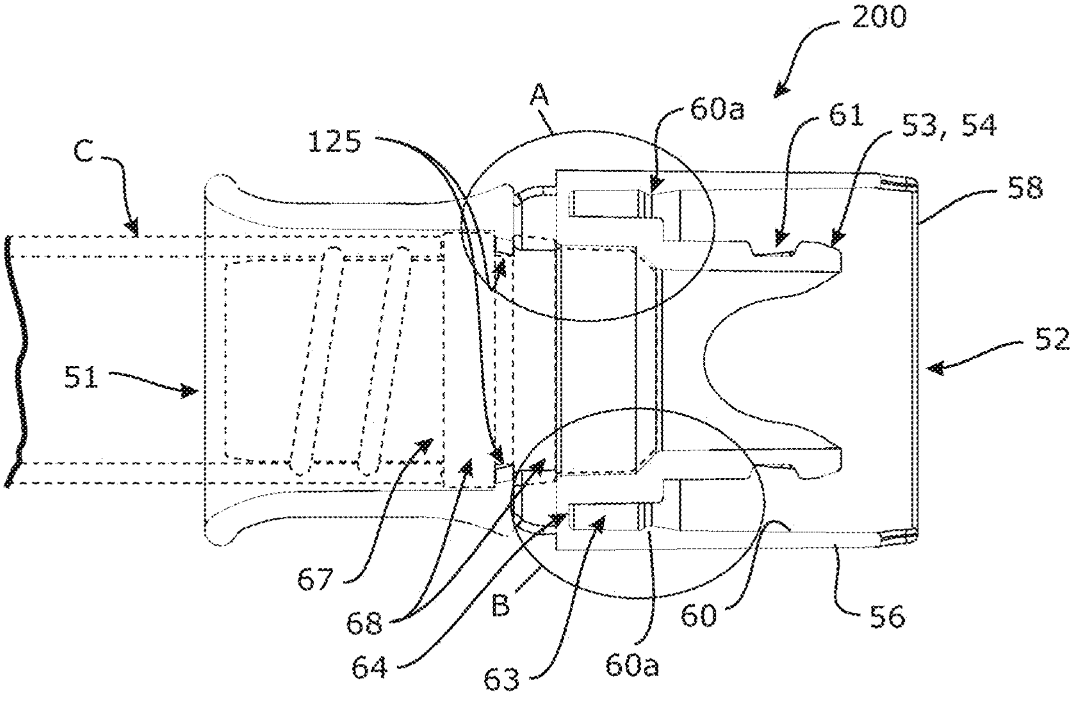
FIG. 29 is an external perspective view of the connector of FIG. 28.

In a first sealing mode, the connector 1 may be configured to provide a first separate surface for sealing upon when a separate connection is made thereto by another connector, the first surface defined by one or both of:

- a side wall surface 20 of a radially extensive flange or lip 16 projecting from the external surface 10 of the body 4, the side wall 20 to face a terminal end face of another connector which may be brought to bear substantially upon the side wall 20, or
- an inner surface 8, substantially at or toward the terminal end of the second end of the connector 1 when brought to bear upon a radially outward facing surface of another connector, such as a radially outwardly facing surface 160 (as for example see in FIG. 29B) of another connector.

For example, when the connector 1, is configured in a first sealing mode where the surface for sealing is provided for, at least in part, by said side wall surface 20, such a first mode of sealing would require the removal, or avoidance, of providing for the radially and/or longitudinally extensive grooves from at least the flange or lip 16 and optionally also from the sheath (or cuff) 17.

In a second sealing mode, the connector 1 may be configured to provide a body of the second end, for sealing upon a second sealing surface of another connector 200, the second sealing surface defined by:

- an internal side wall surface 60 provided substantially at or toward a base end 64 of the second end of the another connector 200, the body of the second end of the connector 1 is brought to bear substantially upon the internal side wall surface or a location along the internal side wall surface at or toward the base end of another connector 200. For example see item 180 in FIG. 29B.

In a third sealing mode, the connector 1 may be configured to provide a body of the second end for sealing upon a third sealing surface of another connector 200, the third sealing surface defined by:

- an internal side wall surface 60 of a protrusion 60A extending radially inwardly of the internal side wall surface 60 of the second end 52 of the another connector 200, when said body of the second end of the connector 1 is brought to bear substantially upon the surface or a location along the surface of the protrusion 60A of the another connector 200. For example, see item 140 in FIG. 29A.

In a fourth sealing mode, the connector 1 is configured to provide a body of the second end for sealing upon a fourth sealing surface of another connector 200, the fourth sealing surface defined by:

- an internal side wall surface 60 of the second end 52 of the another connector 200, where the internal side wall surface extends as a shoulder 63 radially outwardly from one or more male connection features (such as the one or more locking fingers 54), a part of the body of the second end of the connector 1 being brought to bear substantially upon a radially outward surface of the shoulder. For example, see item 170 in FIG. 29B.

In a fifth sealing mode, the connector 1 is configured to provide a body of the second end for sealing upon a fifth sealing surface of another connector 200, the fifth sealing surface defined by:

a radially outward surface of one or more male connection features, in particular a radially outward surface of one or more locking fingers located within the second end 52 of the another connector 200. For example, see item 160 in FIG. 29B.

Figure 29A:
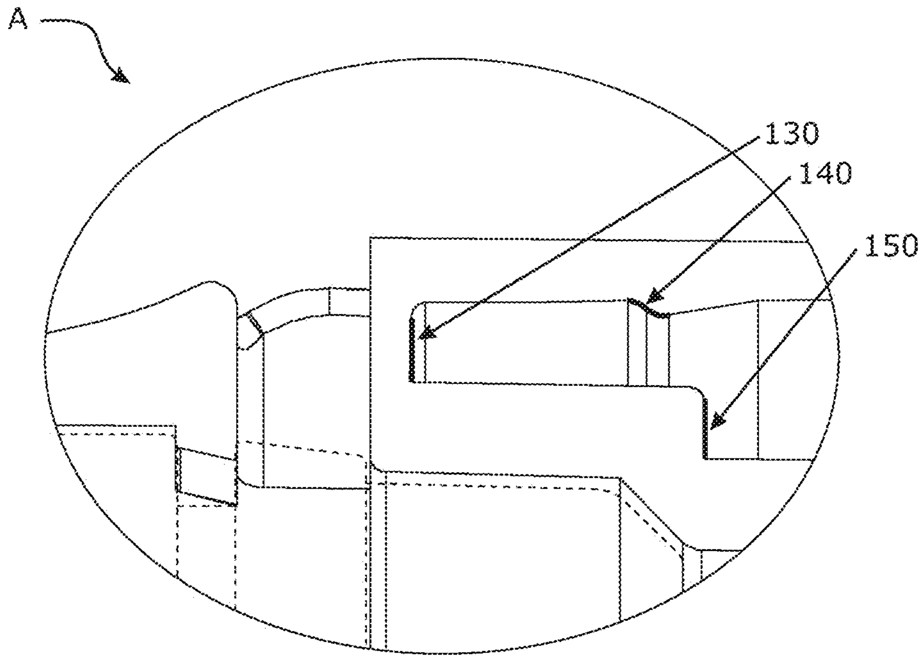
FIGS. 29A and 29B are close-up views of the regions encircled as items 'A' or 'B' in FIG. 29.
Figure 29B:
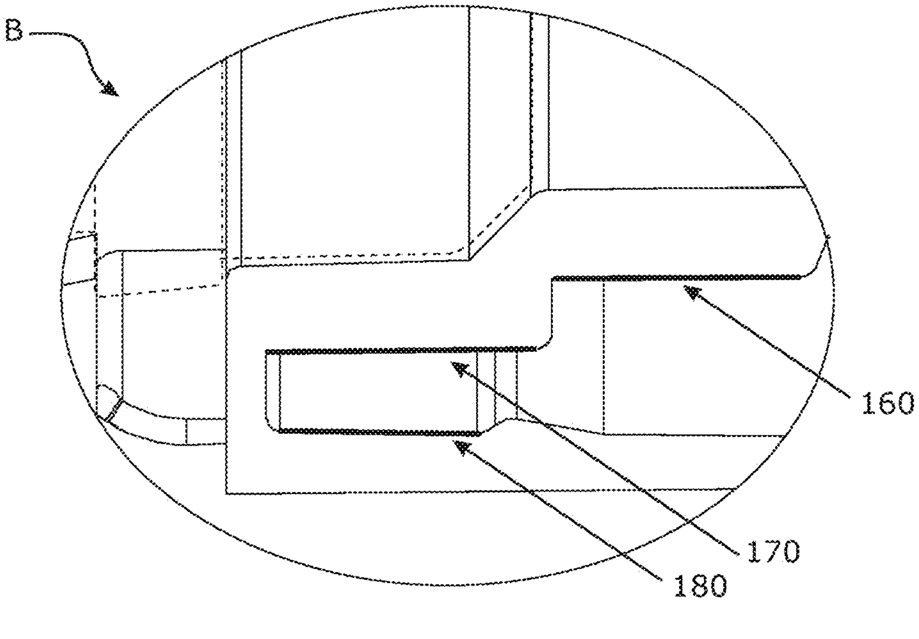

In a sixth sealing mode, the connector 1 is configured to provide a body of the second end, for sealing upon a sixth sealing surface of another connector 200, the sixth sealing surface defined by one or both of:

a lateral face or ledge of a shoulder extending radially outwardly from one or more male connection features, in particular a radially outwardly extensive face or ledge extending radially outwardly from one or more locking fingers located within the second end 52 of another connector 200, for example see item 150 in FIG. 29A, or a lateral face or a base extending as a floor between an outward periphery of a shoulder extending radially outwardly from one or more male connection features of another connector 200, such a lateral face or base extending as a floor being located within a second end of another connector 200, for example see item 130 in FIG. 29A.

The connector 1 as described herein has particular application to being an upstream connector component attached to the terminal end of a breathing conduit which is to supply gas to a patient interface. The connector 1 is capable of operating to be both a female and a male type connector, thereby improving the useability and ability to connect to other types of connectors (where those other connectors provide for male connection features or female connection features).

The connector 1 may have particular application as a connector for a breathing conduit providing a supply of gas from a source. The 'another connector' described above, may be, but without limitation, be a downstream patient interface end connector for a breathing conduit which provides the supplied gas to a patient interface (such as, but not limited to full face masks, nasal cannula, oro-nasal masks, nasal masks—and whether each of these are of a sealing or non-sealing type).

FIGS. 21-25 show a connection made by a connector 200 with the connector 1.

Also disclosed is another connector (as referred to above) or second connector, configured to be engaged or engagable with the connector. The another connector may be bought into mating and/or connection and seal with at least one of the following surfaces of the connector 1:

at least an external surface 10 of the body 4.

at least a side wall of a radially extensive flange or lip. For example the another connector may seal with the side wall 20, of the radially extensive flange or lip 16, projecting from the external surface 10 of the body 4 at least an external surface of a cuff or sleeve 17 provided about the first end of the connector 1.

Figure 36:
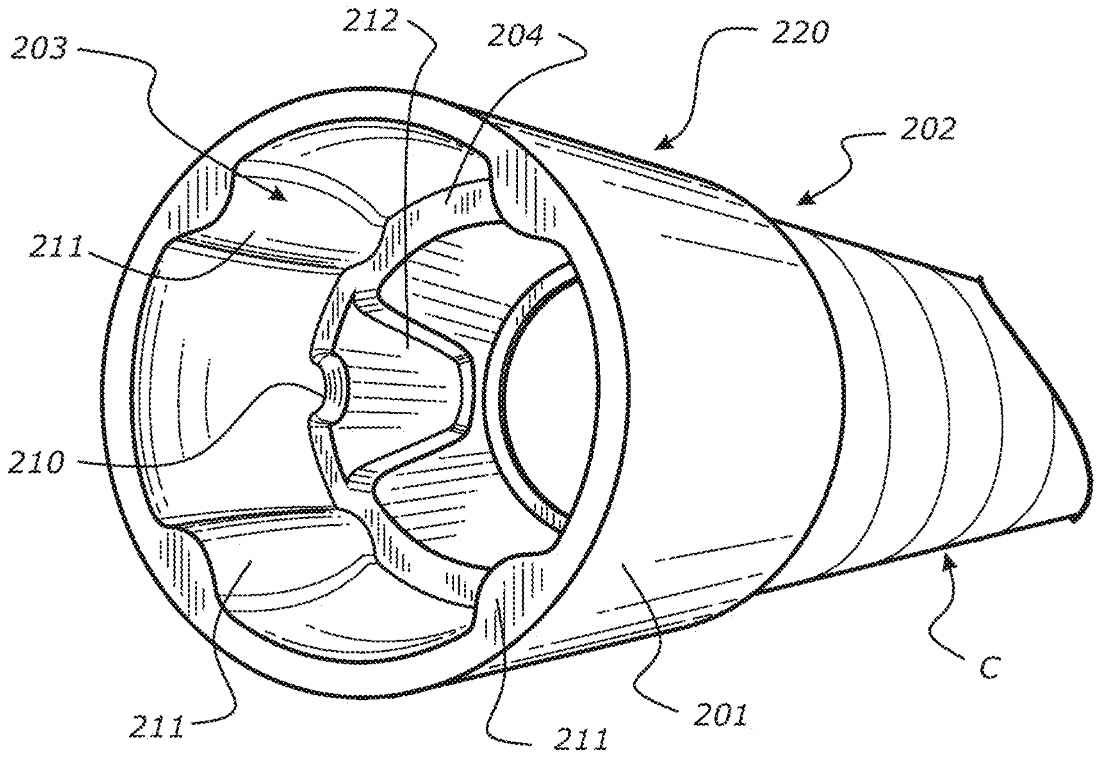
FIG. 36 is a perspective view of a connector.
Figure 36A:
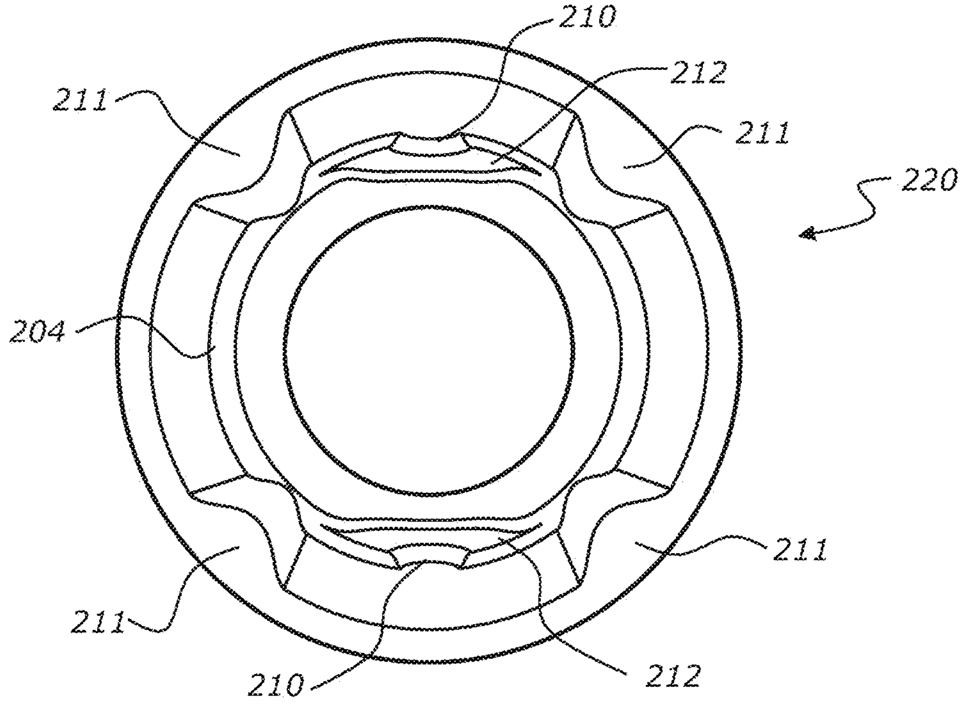
FIG. 36A is an end view of the connector of FIG. 36.

FIGS. 36 and 36A disclose a connector to be coupled or mated in a sealing arrangement with a second connector (for example connector 1.) This connector 220 may be the another connector as described above.

The connector 220 may be provided at a terminal end of a breathing conduit C. Alternatively or additionally, the connector 220 may form part of adapter, which may facilitate the connection of two connectors, i.e. the connection of the connector 1, and any other connector.

The connector has a body 201, comprising a first end 202 and a second end 203. The first end 202, is engaged or engageable with the terminal end of the breathing conduit C or at least a component to be associated with the terminal end of the breathing conduit or tube (for example an adapter as described above.) The second end 203 of the connector 220, is engaged or engageable with a second or another connector (for example, the connector 1). The connector 220 comprises an internal lumen or passage way to receive the second connection internally.

The internal surface of the body 201 may comprise one or more internal connection and/or alignment features 210, 211, 212. The internal connection and/or alignment features 210, 211, 212 may facilitate sealing (pneumatic or otherwise) and/or alignment of the connector and a second connector (for example connector 1) when connected or during connection. The internal connection and/or alignment features 210, 211, 212, may also provide for a visual indication of alignment so a user may more easily align and connect the connector 220, with a second connector. The internal connection and/or alignment features may also provide for retention of the connector 220 with a second connector when connected therewith.

The internal connection and/or alignment features 210, 211, 212 may comprise a rib or protrusion 211 projecting radially inward from the body 201 of the connector 220, or from a notional or actual internal wall or surface of the body 201. The protrusion(s) or rib(s) 211 may extend in a substantially longitudinal direction along a side wall of the internal surface of the body 201 of the connector 220. The protrusion(s) or rib(s) 211 may extend substantially from at or near a second end 203 (for example terminal end of the second end of the connector) in a direction toward the first end 202 of the connector 220.

The internal connection and/or alignment features 210, 211, 212 may comprise a recess 210, 212 projecting radially outward from a notional or actual internal wall or surface. The at least one recess 210, 212 may be located in a side wall or an internal surface of the body 201 of the connector. In some embodiments, the at least one recess may be configured to accommodate an associated projection(s) of a second connector (for example projection 11 of connector 1) when said second connector is brought into a mating or connection with said connector 220.

The internal connection and/or alignment features 210, 211, 212 may provide for, at least in part, sealing, or a sealing surface, between the connector and another connector. For example the internal connection and/or alignment features 210, 211, 212 themselves, or in combination with an inner surface of the body of the connector, may seal with the second connector (for example connector 1)

The internal connection and/or alignment features 210, 211, 212 may be shaped so as to match corresponding features of the second connector. The ribs 211, of the connector may be configured to match with corresponding recesses (for example longitudinally recessed or grooved regions 18*b* of the connector 1 of a cuff or sleeve 17) of a second connector (for example connector 1). The recesses 210, 212 may be configured to match with corresponding ribs or protrusions (for example visual alignment features 12 or protrusion 16) of a second connector.

The internal connection and/or alignment features 210, 211, 212 may be co-located or co-locatable for keying with a reciprocally shaped projection or recess of a portion of a second connector. This may be one mechanism of providing an alignment function between the connector 220 and a second connector. The internal connection and/or alignment features 210, 211, 212 may be shaped to facilitate correct orientation for coupling, so that when the connector 220 is brought into contact with the second connector the connectors are aligned, to ensure the internal connection and/or alignment features 210, 211, 212 line up with the corresponding ribs or protrusion, and/or recess on the second connector. The keying may also prevent rotation of the components relative to each other when in a coupled state.

The internal connection and/or alignment features 210, 211, 212 may be arranged circumferentially around the internal surface of the connector. The internal connection and/or alignment features 210, 211, 212 (for example the ribs and/or protrusions) may be spaced equidistantly around the circumference of the internal surface of the body 201 of the connector 220. Alternatively, the internal connection and/or alignment features 210, 211, 212 may be arranged so that they are not equidistant (i.e. non-symmetrical about a plane), this may only allow connection between the connector 220 and a second connector in a particular orientation.

There may be one or more or a plurality of internal connection and/or alignment features 210, 211, 212 (ribs and/or recesses), optionally there are 2, or 3, or 4, or 5, or 6 ribs and/or recesses. In the embodiment as shown in FIG. 36, there are four ribs 211.

There may be a pair of recesses 210, 212. The pair of recesses 210, 212 may be located so they are spaced equidistantly around the circumference of the internal surface of the body 201 of the connector 220. Alternatively, the recesses 210, 212, 212 may be arranged so that they not equidistant (i.e. non-symmetrical about a plane). The recesses 210, 212 may be arranged to be overlapping such that one, at least partially, fits within the other or one is at least partially defined by the other.

The internal surface of the body 201 of the connector 220 may comprise at least one sealing surface or surface for sealing. The sealing surfaces as mentioned herein are labelled, for convenience and clarity, as the first, second and third sealing surfaces. However, it will be appreciated a connector may comprise a for example third, or second sealing surface without necessarily comprising a first sealing surface. To be clear, the inclusion of a particularly numbered sealing surface does not require the inclusion of the earlier numbered sealing surface(s).

The connector 220 may provide at least a first internal surface for sealing upon an external part of a said second connector, when a connection or mating is made thereto by or with said second connector. The first internal surface is provided by a circumferential portion of the internal surface of the body 201. The circumferential portion may be located at or near the second end 203 of the body 201 of the connector 220. The first sealing surface may be provided so as to be substantially continuously and substantially circumferentially locatable about an external part of a second connector (for example a cuff or sleeve 17 of the connector 1.)

FIGS. 37-40A illustrate examples of a connector 220, which seal with a second connector (being connector 1), by at least a first internal sealing surface.

The internal connection and/or alignment features 210, 211, 212 may form at least part of the first internal surface of the body. The recess(es) and/or rib(s) or protrusion(s) may form at least part of the first internal surface. The protrusion (s) or rib(s) 211 may extend in a substantially longitudinal direction along the internal surface of the body 201 of the connector 220. Optionally, the protrusion(s) or rib(s) 211 may extend substantially from at or near a second end 203 (for example terminal end of the second end of the connector) in a direction toward the first end 202 of the connector 220. It will be appreciated that the ribs and/or protrusions 211 of the connector 1 may extend only part way into or along the channel 18*b*.

The first internal surface of the body 201 of the connector 220 may be substantially curved when viewed in cross section (as shown in the cross sections of FIGS. 37A, 38A, 39A and 40A). Additionally or alternatively, the profile of the first internal surface (e.g. the radius of curvature and location of a curve of the first internal surface) may match an external profile (e.g. an external curve or curvature) of a cuff or sleeve 17 of a second connector. The profile of the first internal surface may allow for sealing between the first internal surface and a cuff or sleeve 17 of a second connector. FIGS. 37-40A illustrate where the first internal surface is profiled to match the profile of a cuff or sleeve 17 of a second connector (for example connector 1).

FIGS. 37 to 40A show a series of embodiments of the connector 220 where the ribs or protrusions 211 extend into the recesses or longitudinal channels 18*b* of the sleeve 17.

Figure 37:
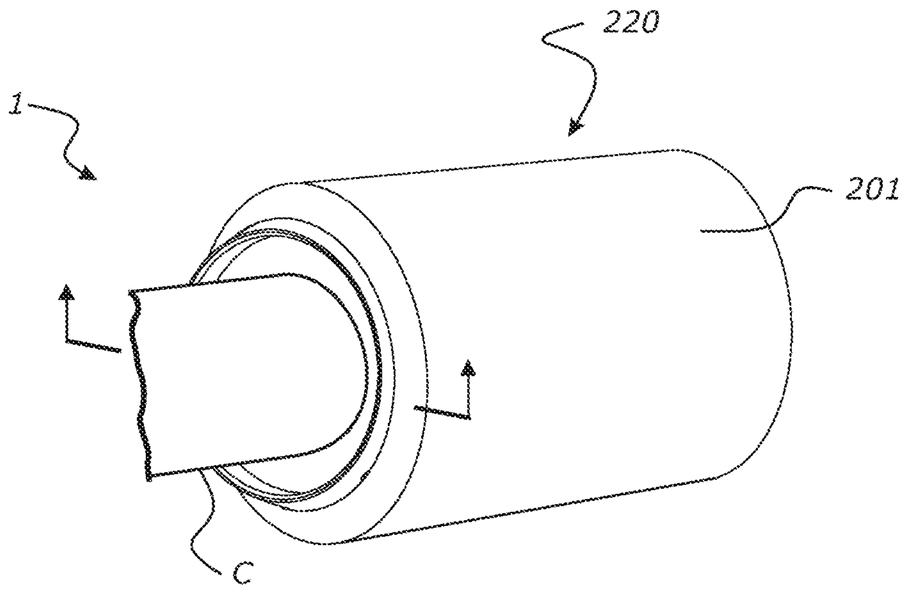
FIG. 37 shows a connector in engagement with a second connector.
Figure 37A:
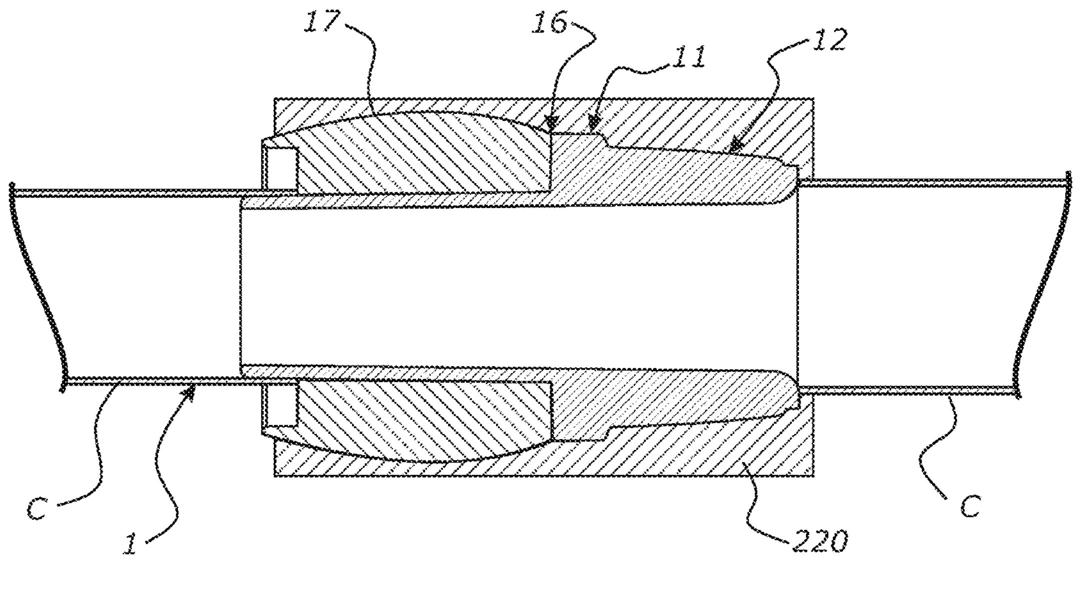
FIG. 37A shows a cross-section of FIG. 37.

FIG. 37 shows a connector 220 where the first internal surface and the ribs or protrusions 211 extend to the end, or substantially near the end of the cuff or sleeve 17 of the connector 1. FIG. 37A shows a cross section of the connector 220 in completed connection with the second connector, being connector 1. It is also envisaged that the first internal surface may extend past the end of the cuff or sleeve 17 of the connector 1.

Figure 38:
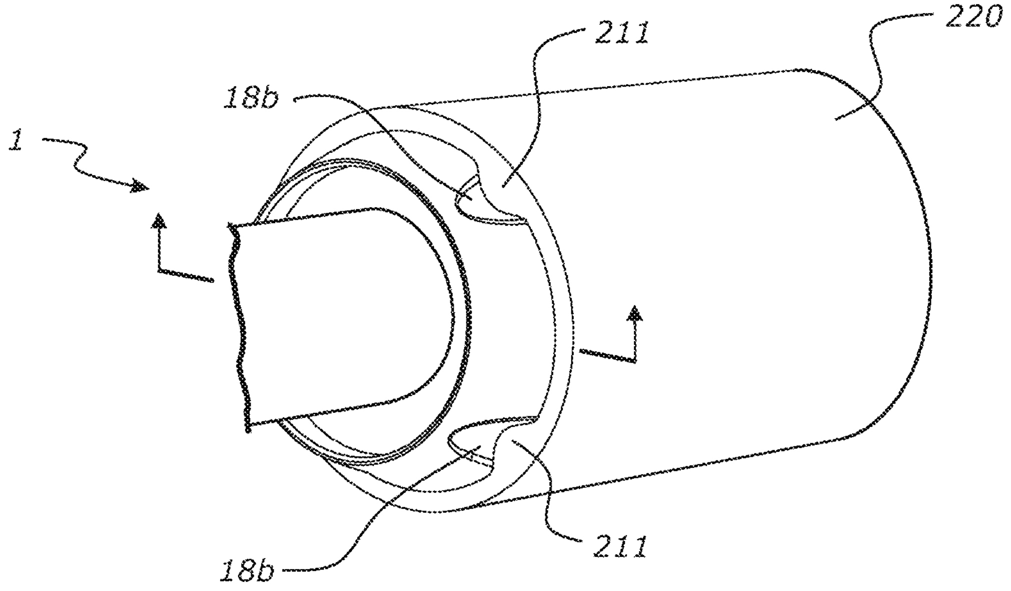
FIG. 38 shows a connector in engagement with a second connector.
Figure 38A:
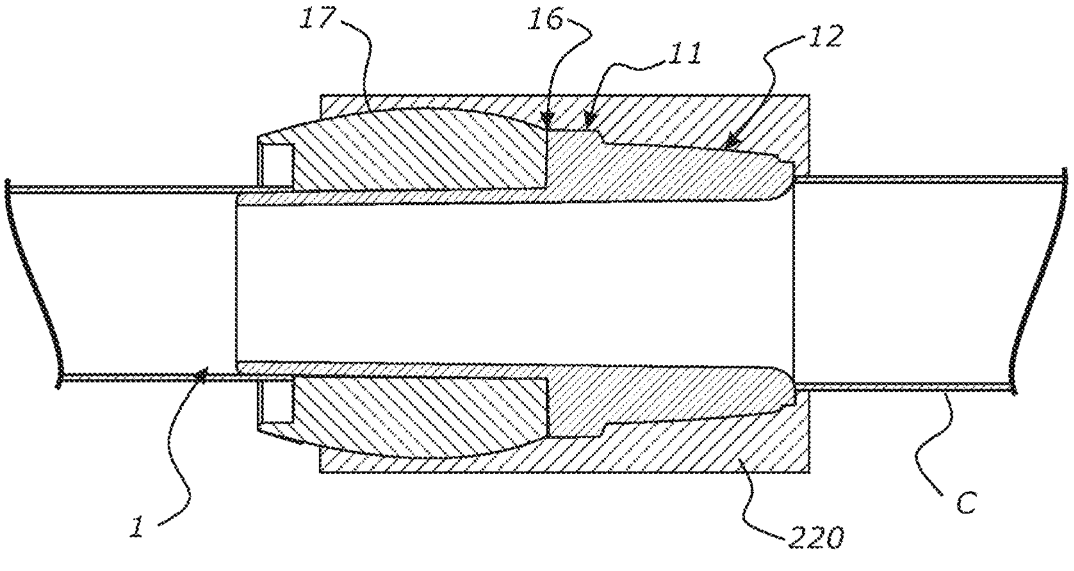
FIG. 38A shows a cross-section of FIG. 38.

FIG. 38 shows a connector 220 where the first internal surface and the ribs or protrusions 211 extend to a position between an outer-most apex of the external profile of the cuff of sleeve 17 of the second connector 1 and the end of the cuff or sleeve 17 nearest the terminal end (connected to conduit C) of the second connector. FIG. 38A shows a cross section of the connector 220 in completed connection with the second connector (being connector 1.)

In the embodiments of FIGS. 37-38A the connector 220 may be made from a soft rubberised material, so, the second end of the connector can be stretched over the apex of the sleeve 17. The embodiments of FIGS. 39-42A may also be made of a soft of rubberised material.

In the embodiments where the connector does not extend beyond the largest diameter of the cuff (for example FIGS. 39-42A) the connector may be made of a rigid material.

Figure 39:
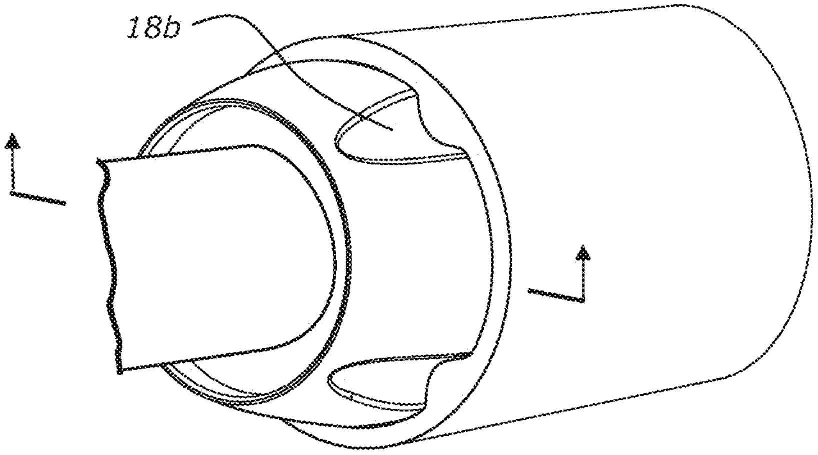
FIG. 39 shows a connector in engagement with a second connector.
Figure 39A:
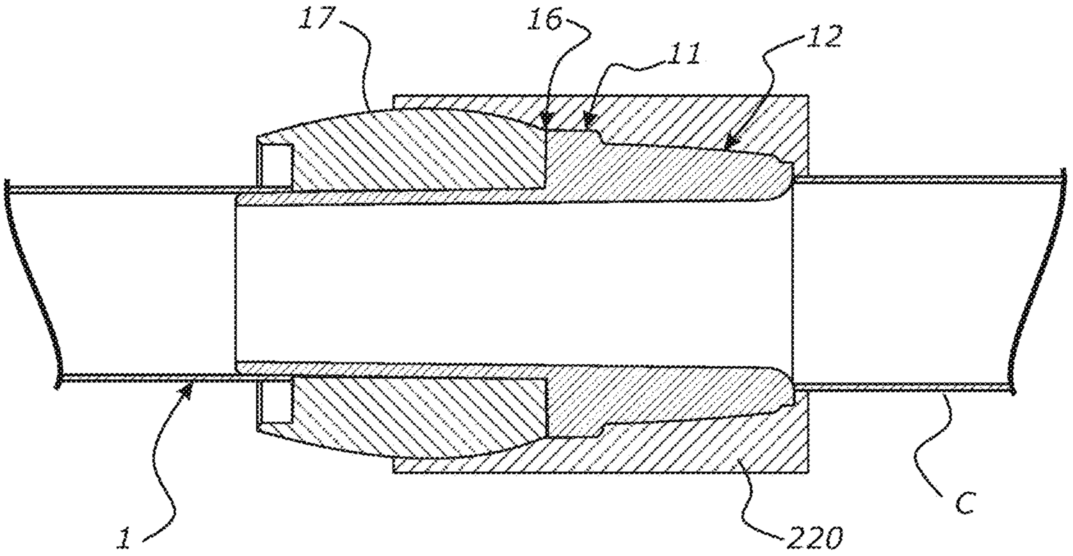
FIG. 39A shows a cross-section of FIG. 39.

FIG. 39 shows a connector 220, where the first internal surface and the ribs or protrusions 211 are of a sufficient dimension so as to, in use, extend substantially to an outer-most apex of the external profile defined by the sleeve 17 of the connector 1.

Figure 40:
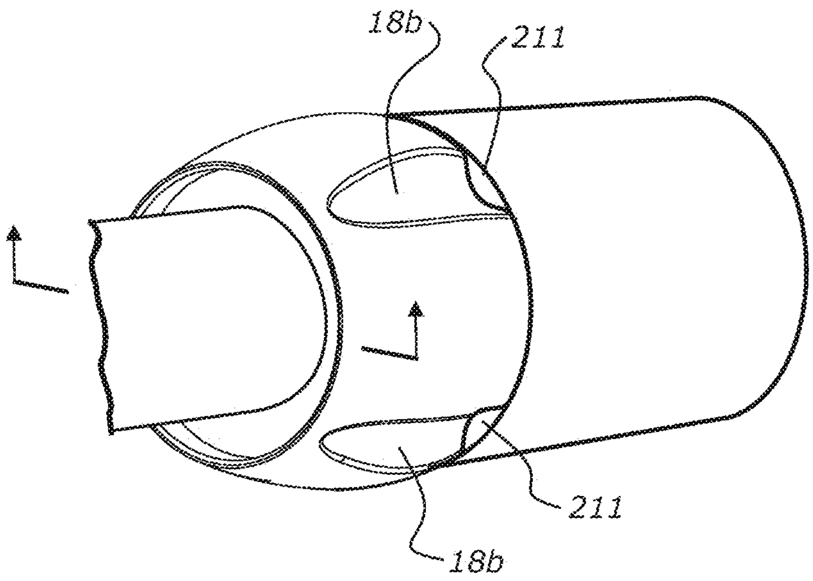
FIG. 40 shows a connector in engagement with a second connector.
Figure 40A:
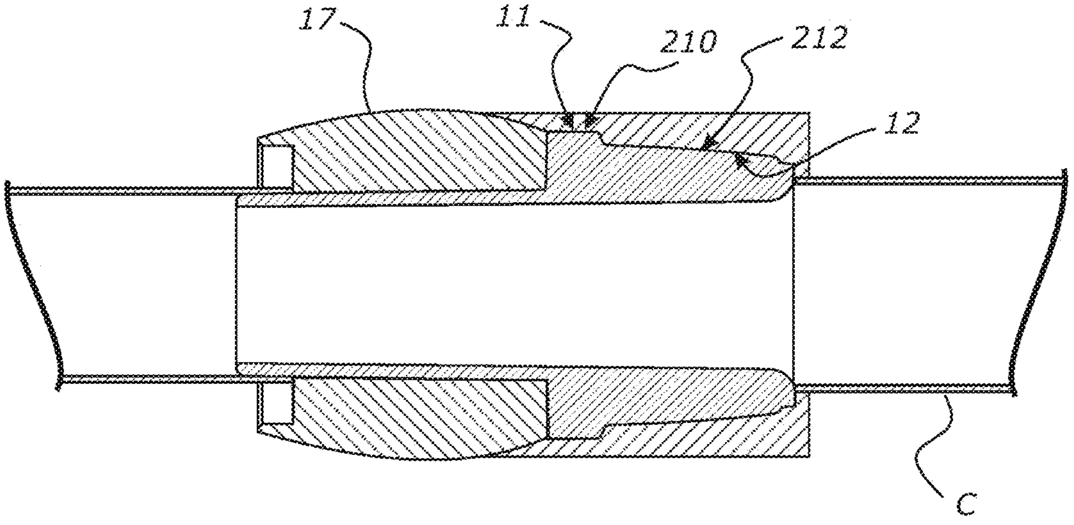
FIG. 40A shows a cross-section of FIG. 40.

FIG. 40 shows a connector 220 where the first internal surface and the ribs or protrusions 211 extend to a position between the outer-most apex of the external profile of the cuff of sleeve 17 of the second connector 1 and the end of the cuff or sleeve 17 nearest the end of the second connector 1 not connected to a conduit C. FIG. 40A shows a cross section of the connector 220 in completed connection with the second connector, being connector 1.

The connector 220 may provide a second internal surface for sealing upon when a connection or mating is made thereto by or with said another connector. The second surface being defined by a substantially radially extensive flange or lip 204 (for example as shown in FIGS. 36 and 36A). The flange or lip 204, projects radially inward from the internal surface of the body as a side wall surface. The flange or lip 204 may provide a face, upon which a respective face (for example flange or lip 12, or a terminal end) of the second connector seals.

The radially extensive flange or lip 204 may comprise at least one of said internal connection or alignment feature. The at least one connection or alignment feature may be a rib or protrusion, or a recess. The at least one recess may be located in flange or lip 204, or be a depression or other surface relief feature provided upon the face of the flange or lip 204. Optionally the depression or other surface relief feature is a cut-out of the face.

The internal connection and/or alignment feature(s) may be to be co-located or co-locatable for keying with a reciprocally shaped projection or recess of a portion of a second connector. In the embodiments as shown in FIGS. 37-41A the connector 220 may comprise ribs 211, which are co-locatable with recesses 18*a* of the connector 1. The connector 220 may also comprise at least one recess 210 located in flange or lip 204, the at least one recess 210 being co-locatable with ribs or projections 11 of the second connector (being connector 1).

The recess may be configured to accommodate or be receivable of an associated projection or other shaped feature of a second connector when the second connector is brought into a mating or connection with said second internal surface. The at least one protrusion may be located in a side wall or an internal surface of the connector, the at least one protrusion to accommodate recesses of said another connector.

The face of the flange or lip 24 may be configured to provide for a substantially planar surface upon which a portion or a surface of the second connector can mate or engage with. The face may be oriented to substantially face toward said second end 203 of said connector 220. The face may mate or seal upon a side wall, or ledge, or lip or base, or end of a second connector. When the second connector is connector 1, the face may seal with a corresponding face of the flange or lip 16 of the connector 1.

The connector may also provide at least a third internal surface for sealing upon an external part of a second connector, when a connection or mating is made thereto by or with the second connector. The third internal surface is provided by a circumferential portion of the internal surface of the body, optionally said circumferential portion located at or near the first end of the body of the connector and provided so as to be substantially continuously and substantially circumferentially locatable about an external part of a said another connector to which the third internal surface is to be put into connection or a mating arrangement therewith.

Figure 41:
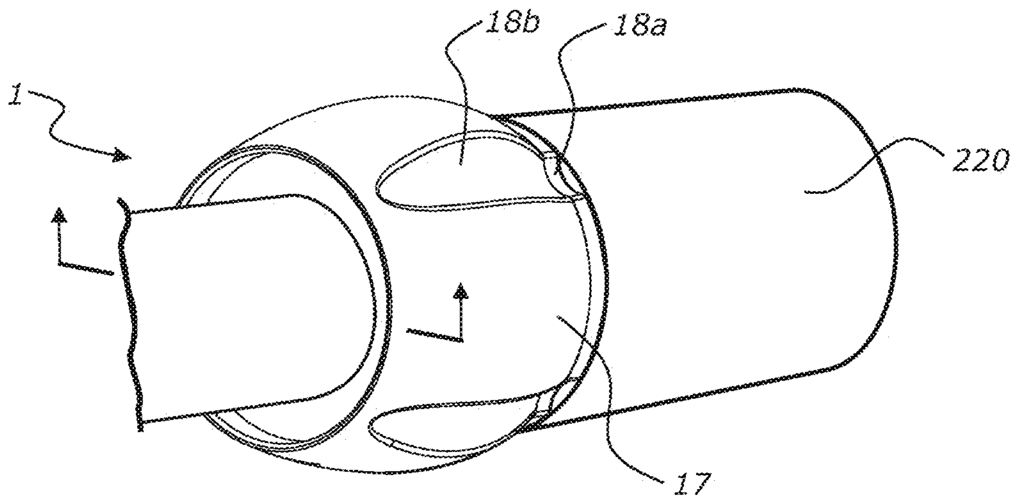
FIG. 41 shows a connector in engagement with a second connector.
Figure 41A:
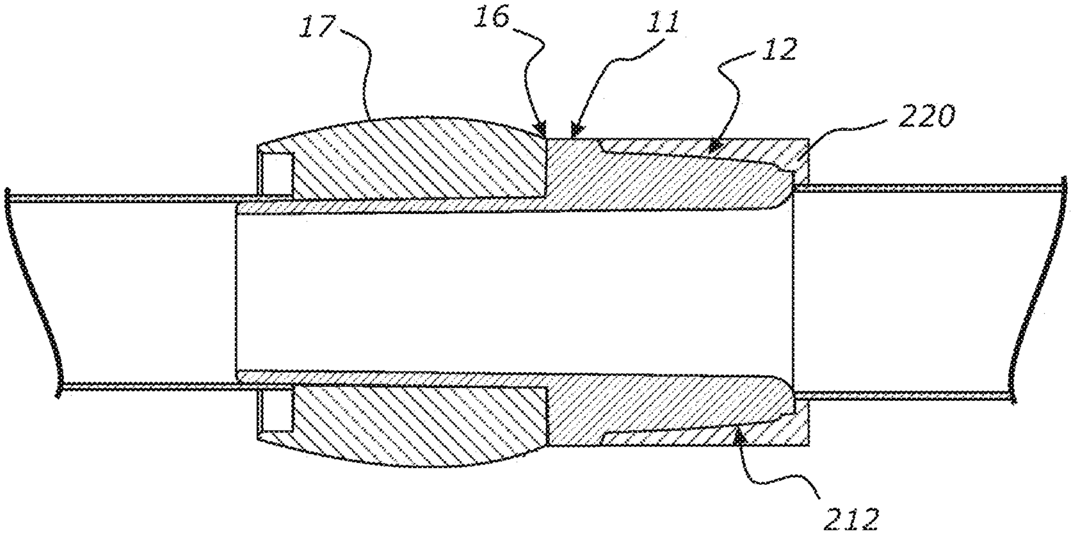
FIG. 41A shows a cross-section of FIG. 41.
Figure 42:
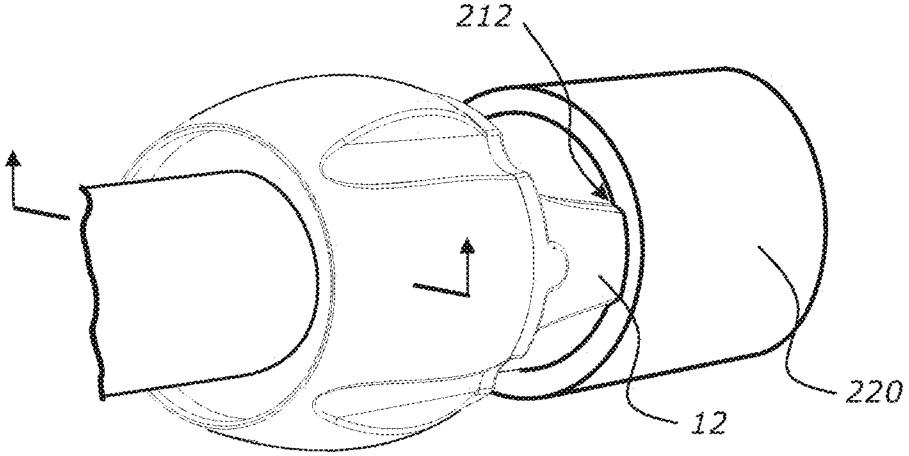
FIG. 42 shows a connector in engagement with a second connector.
Figure 42A:
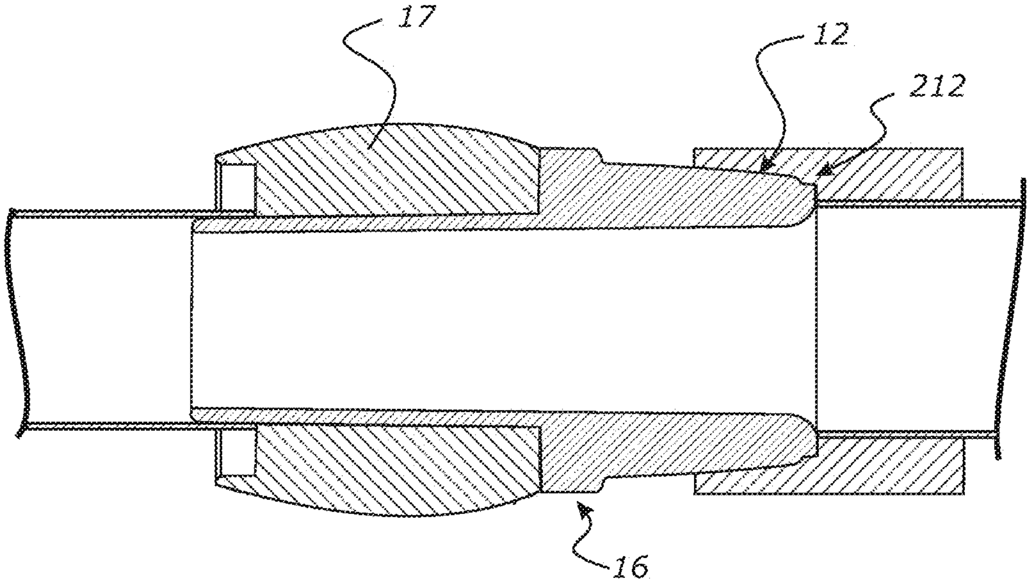
FIG. 42A shows a cross-section of FIG. 42.

The connector 220 may provide at least a third internal surface for sealing upon an external part of a said second connector, when a connection or mating is made thereto by or with said second connector. The third internal surface is provided by a circumferential portion of the internal surface of the body 201. The circumferential portion may be located at or near the first end 202 of the body 201 of the connector 220. Alternatively, in other embodiments (such as that as shown in FIGS. 41-42A) the third internal surface is located near the second end 203 of the body 201. The first sealing surface may be provided so as to be substantially continuously and substantially circumferentially locatable about an external part of a said second connector (for example an external surface 10 of the body 4 of the connector 1.)

The alignment or connection feature may form at least part of the third internal surface of the body. For example as shown in FIGS. 41-42A, the recess 212 forms part of the third internal surface for sealing. The at least one recess may be shaped so as to accommodate projections of said second connector for example the visual indicator 12.

The recess may be configured to accommodate and seal with at least part of the projection of the second connector. The remaining internal surface of the body of the connector 220 may then seal with at least part of the external surface 10 of the body 4 of the second connector 1.

The recess may comprise a pair of shoulders, sloping away from each other and away from an end (for example an apex) at the intersection of the shoulders. The end of the recess being located substantially more toward the first end of the connector 220 than the shoulders. The at least one recess may be substantially tongue shaped, and/or substantially triangular and/or substantially tapers toward an end. The recess may extend only part of the way into the body of the connector 220 (as shown in FIG. 42.) As such when the connector 220 is connected to the second connector 1, the body 201 of the connector 220 may extend only part of the way onto the second connector 1.

Alternatively or additionally, the recess may be a longitudinal channel (for example to accommodate the ribs 12 of FIG. 1)

FIGS. 42-42A show connectors 220, which seal, at least in part, with a second connector (being connector 1) by a third sealing surface. In the embodiment of FIGS. 42-42A, the connector 220 seals with part of the external surface 10 of the body 4 of the second connector 1, including part of the rib or protrusion 12.

Figure 43:
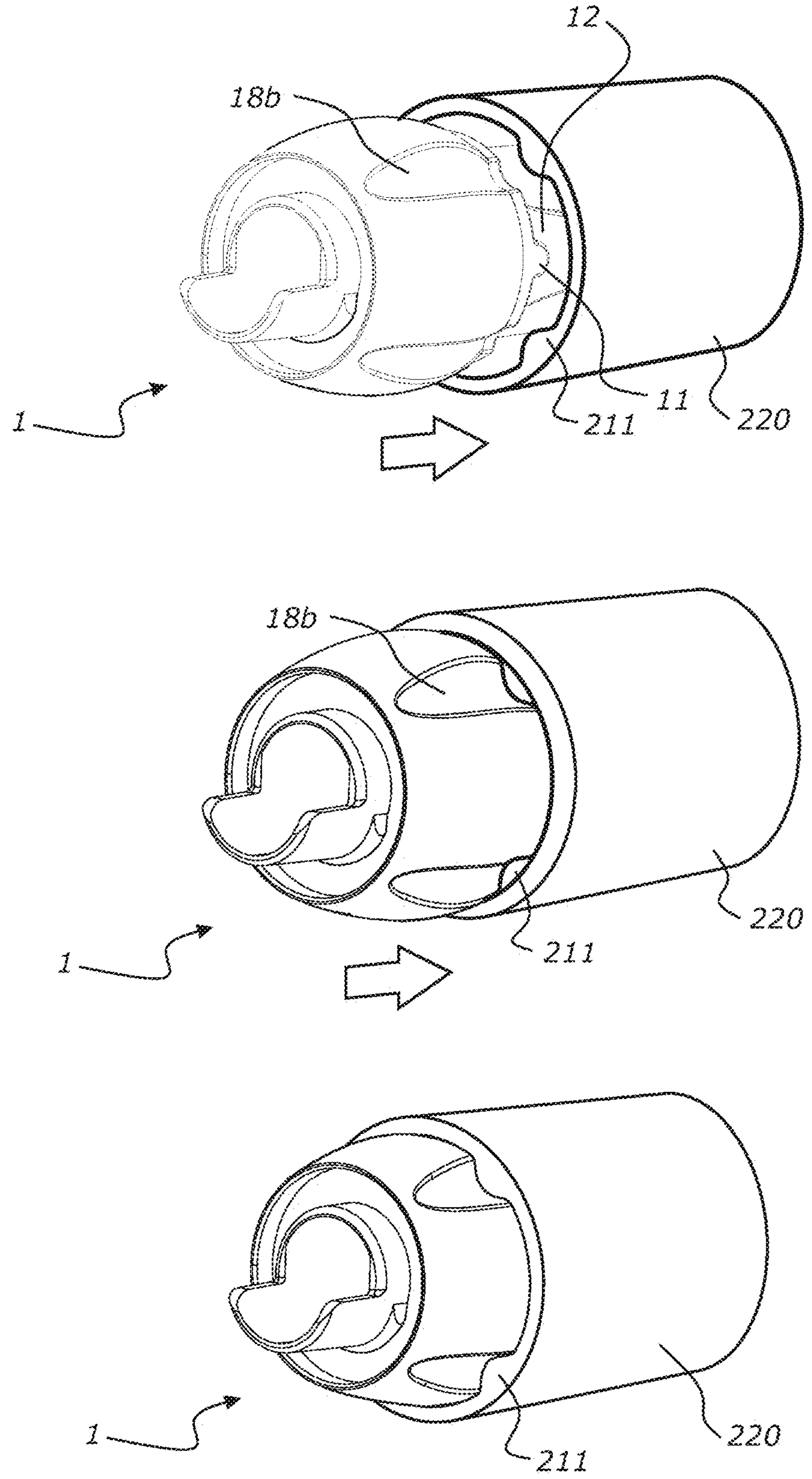
FIG. 43 shows engagement between a connector and a second connector

FIG. 43 shows the connection of the connector 220 with a second connector (for example connector 1). The second connector 1 is inserted into the connector 220, such that the external alignment feature(s) 11 or visual aids 12 are mated and optionally seal with their corresponding internal connection/alignment features 210, 212. As the connectors are mated together the recessed or grooved regions 18B mate (and optionally seal) with the ribs 211.

It will be appreciated that the connector may comprise any combination of the first, second and third sealing surfaces as described above.

It will also be appreciated that the second connector may be a single piece as shown in FIGS. 37-41, or made from multiple pieces as shown in FIGS. 42 and 42A (and with reference to the connector 1 as described above.)

Notwithstanding the above description, there may be provided further connectors 200 and 40 which are operationally compatible with the connector 1. The following description is provided primarily with reference to the connectors 200 and 40, as seen in FIGS. 21-25 and 28-35B.

Accordingly, there is provided a connector 200, 40 for use with a conduit to supply gases to a user.

Figure 28:
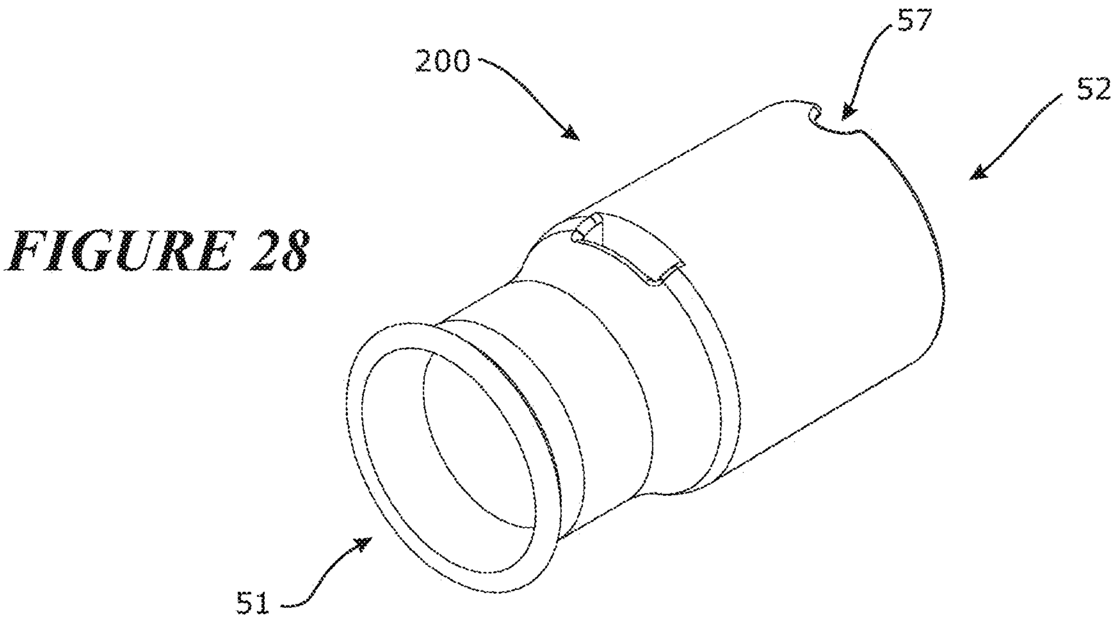
FIG. 28 is a cross-section through the left-hand end connector of the connector arrangements shown in FIGS. 21-23.

The connector 200, 40 to be provided at a terminal end of a breathing conduit. The connector 200, 40 comprises a body 50, the body comprising a first end 51 and a second end 52, the body 50 internally defining a lumen 53 for the passage of gas therethrough between each of the first and second ends. The first end 51, in use, being engaged or engageable with the terminal end of the breathing conduit or at least a component to be associated with the terminal end of the breathing conduit. The connector 200 may be connected to the terminal end of the breathing conduit by a swivel-type connector connected to the body of the connector. The second end 52, in use, to be engaged or engageable with another connector (such as the connector of item 1 previously described herein). An internal surface of the body comprises one or more internal male connection features 53 extending therein configured for connection with a female end or female part of another connector receivable of said male connection features 53. The male internal connection features 53 comprising one or more (optionally a pair) of locking fingers 54. The connector 200, 40 comprising one or both of:

a. surrounding of the one or more internal male connection features 53 is an outer wall 55, an exterior surface 56 of the outer wall being tapered, tapered in a direction substantially longitudinally with the connector (for example, see FIG. 30 to illustrate a tapered arrangement), b. surrounding of the one or more internal male connection features 53 is an outer wall 55, the outer or at least an exterior surface 56 of the outer wall, comprising: one or more external alignment feature(s) 57 configured for aligning the connector 40 or another connector into an externally aligned connection therebetween, and/or one or more external visual aid(s) is/are configured for, in use, providing an externally visible guide for alignment of the connector or another connector into an aligned connection therebetween (for example, see FIGS. 28-29 to illustrate such an arrangement).

In some embodiments the first end of the connector 51 comprises a sleeve portion that flares outwardly. The outwardly flared portion allows for movement of a connected breathing conduit relative to the connector 40, so that the breathing conduit may flex and bending without damage from the connector. Additionally, the outwardly flared sleeve portion also allows the user to better grip the connector for easier connection and disconnection with other connectors.

Figure 28A:
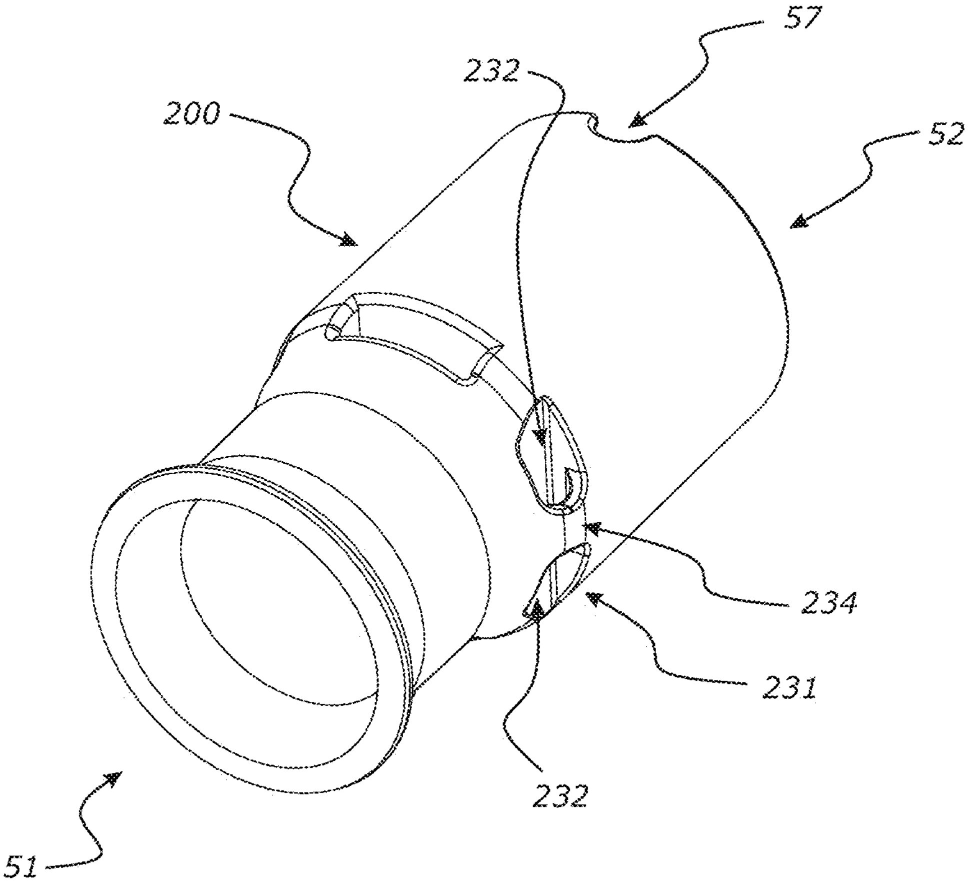
FIG. 28A shows a perspective view of a connector.

The connector may comprise at least one securement feature 231. FIG. 28A shows an embodiment of the connector 200 where the securement 231 is formed by a recessed region 232 and a bridging portion 234. The bridging potion 234 allows for the connection of a lanyard (or a part of a lanyard) to be fastened to the connector 200. Other structural features (forming the securement feature 231) for attaching the lanyard to the connector 200 are envisaged such as an integral loop or clip.

FIG. 28B1 shows a side view of the connector 200 of FIG. 28A. The connector 200 may comprise a pair of securement features 231 (although in the side view of connector 200 only a single securement feature 231 is shown, the second securement feature 231 being hidden from view), and they may be, for example, disposed equidistantly around a perimeter of connector 200. FIG. 28B2 shows a top view of the connector 200 of the connector 200 of FIG. 28A comprising a pair of securement systems 231. The pair of securement systems 231 are located in an opposing manner, such that the securement systems 231 are located on opposite sides of the connector 200. A lanyard 240 may be connected to one or both of these securement systems 231.

Figure 28C:
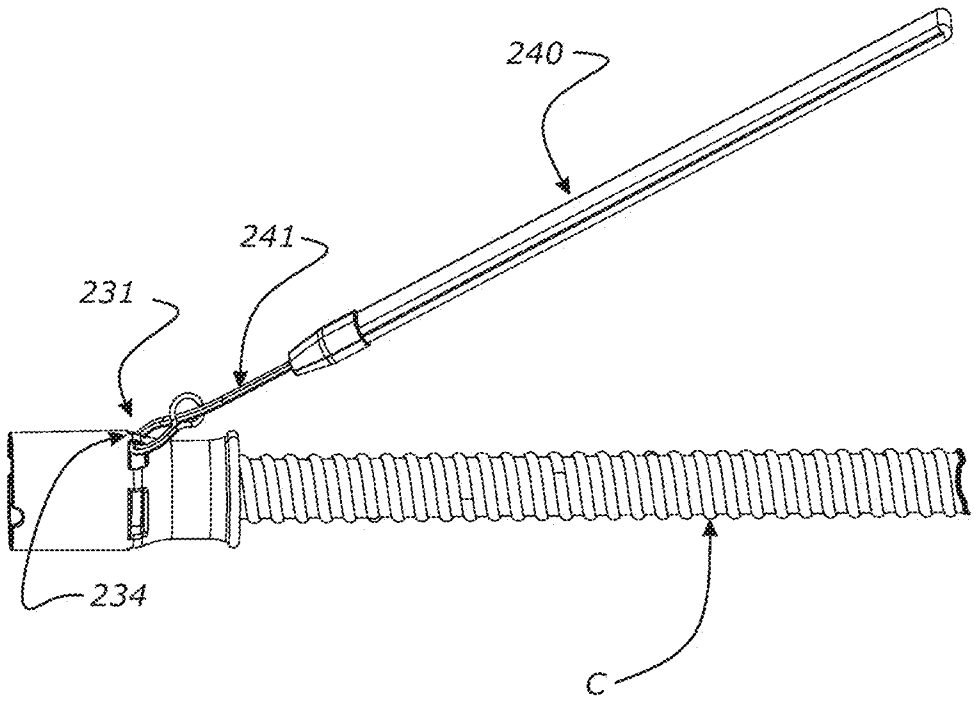
FIG. 28C shows a lanyard connected to the connector of FIGS. 28A-28B2.

FIG. 28C shows a lanyard 240 fastened or engaged with the securement feature 231 of the connector 200. The lanyard 240 comprises a looped portion 241 which can be fastened around the bridge 234 and then pulled through itself to securely associate the lanyard 240 to the connector 200. The lanyard 240 can then be placed around a user's neck, or a feature of the environment to take or support at least some of the weight of the connector 200, attached conduit, and/or interface.

Figure 28F:
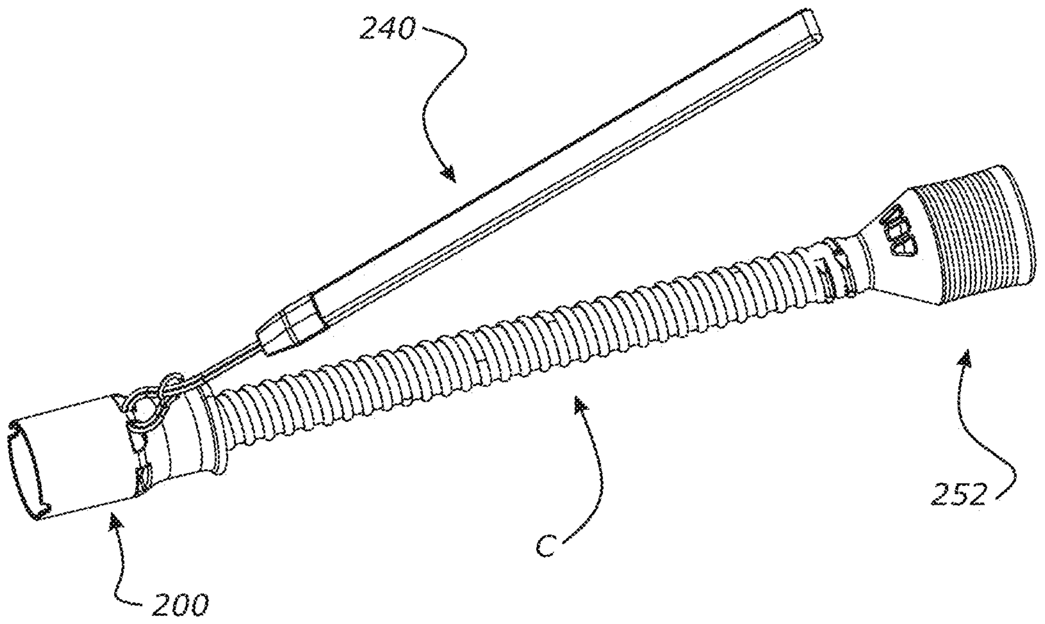
FIG. 28F shows an assembly of the connector of FIGS. 28A-28B2 with a lanyard and connected to a connector.
Figure 28E:
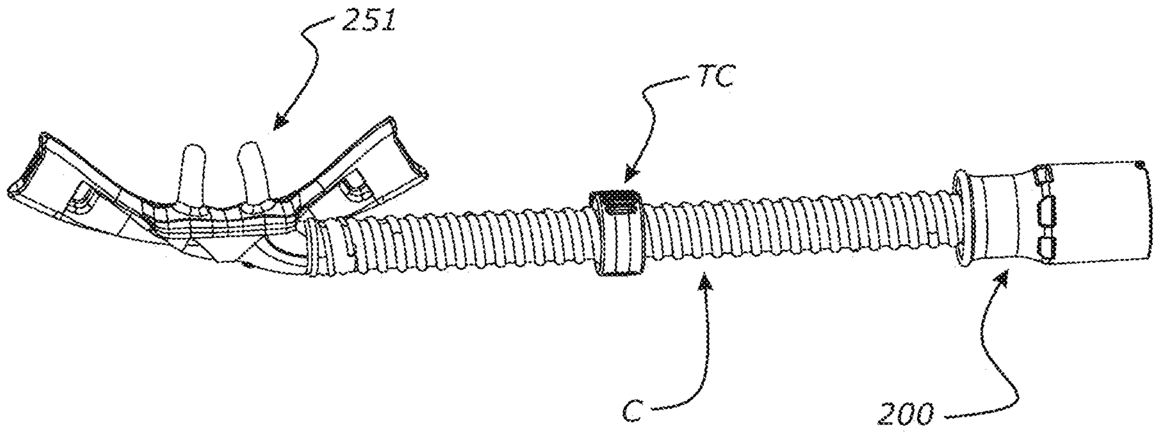
FIG. 28E shows an assembly of the connector of FIGS. 28A-28B2 connected to a patient interface as a nasal cannula.
Figure 28D:
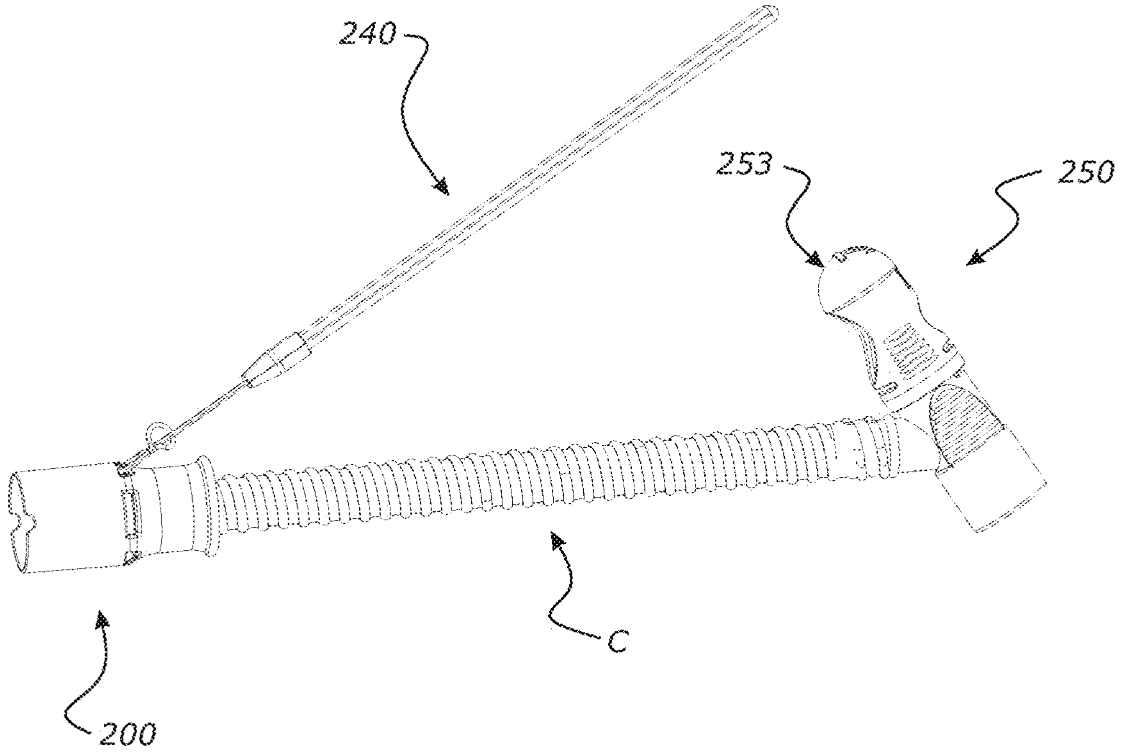
FIG. 28D shows an assembly of the connector of FIGS. 28A-28B2 with an attached optional lanyard, and a patient interface as a tracheostomy interface.

FIG. 28D shows the connector 200 with an attached lanyard 240 (optional), and a patient interface as a tracheostomy interface 250 via a conduit C. The tracheostomy interface is connected to a tracheostomy guard 253. The tracheostomy guard 253 may be, for example, that as described in U.S. Ser. No. 62/329,638 to the common applicant, Fisher & Paykel Healthcare Limited, the contents of which are incorporated herein.

FIG. 28E shows the connector 200 without a lanyard and connected to a patient interface such as a nasal cannula 251 via a conduit C. An optional tube clip TC may be utilised and provided along a conduit C. The tube clip TC may comprise features for being attached to an item in the environment to thereby assist with support of the conduit C, the interface 251 or other parts of a breathing circuit. In this way the weight of the part of the breathing circuit close to a patient or user can be supported.

FIG. 28F shows the connector 200 with a lanyard 240 and connected to a connector 252 via a conduit C.

Accordingly, and with reference for example to FIGS. 30-31, there is also provided a connector 40 for use with a conduit to supply gases to a user. The connector comprises a body 50, the body 50 comprising a first end 51 and a second end 52. The body 50 internally defining a lumen for the passage of gas therethrough between each of the first and second ends. The first end 51, in use, being engaged or engageable with the terminal end of the breathing conduit (such as a tube leading to a patient interface) or at least a component to be associated with the terminal end of the breathing tube. The second end 52, in use, to be engaged or engageable with another connector. An external surface of the body 50 comprises a cuff 65 provided at least substantially about the first end 51 of the connector body 50 (optionally at least partially overlapping of a portion of the second end 52 of the connector body 50), said cuff 65 extending substantially longitudinally down at least a part of a length of the breathing tube to be engaged or engageable with the first end 51, and wherein said cuff is an elasticised or elastic-type material, such as silicone or a thermoplastic elastomers (TPE) type material.

A diameter of the second end's 52 outer wall 55 is smallest at a terminal end 58 of the second end (i.e. being the external diameter), with the (external) diameter increasing in a direction extending away from the terminal end 58 of the second end 52 towards the first end 51.

The one or more locking fingers 54 are housed substantially within the second end 52 of the connector 200, 40.

A space 59 is defined between an outer surface of the one or more internal male connection features 53 (or locking fingers 54) and an inner surface 60 of the outer wall.

The outer wall 55 is configured to provide for one or more alignment feature(s) 57 and/or one or more external visual aid(s). The one or more alignment feature(s) 57 assist in aligning the outer wall with a reciprocally shaped feature on another connector. External visual aids may include graphics or other visual indicators for a user to correctly align and position the alignment feature on the outer wall with a reciprocal feature of another connector which is brought to bear upon the alignment feature(s) 57.

In some configurations, the one or more internal male connection features 53 is/are oriented so as to be radially aligned with the external alignment features 57 and/or the external visual aids. Each of these things in combination providing visual indicators, as well as physical aides to ensure a correct alignment of once connector with another connector.

As shown in various figures, but for example see FIGS. 24-25, 30-31, the external alignment feature(s) 57 may be one or more cut-outs at a terminal end 58 or face of the outer wall 55 of the second end 52. The cut-outs can be configured to be received by a substantially reciprocally shaped portion on a connector to which said outer wall is to be placed into contact.

The various external alignment features 57 can be spaced, arrayed or arranged evenly or equidistantly from each other about the circumference a terminal end face of the outer wall of the second end.

The external alignment features 57 are configured to be co-located or co-locatable for keying with a reciprocally shaped projection of a sleeved portion of another connector when brought to bear into connection during a connection between a terminal face 58 of the second end 52 of the connector 200, 40 and another connector.

The external alignment feature(s) 57 of the connector 40 may be shaped or configured to prevent connection of the internal connection features 53 of the connector with another connector (for example connector 1), when the external alignment feature(s) of the connector 40 and an external alignment feature of another connector (for example connector 1) are in an unaligned orientation.

Additionally or alternatively the external alignment feature(s) 57 of the connector 40 may be shaped or configured to allow connection of the internal connection features 53 of the connector with another connector (for example connector 1), when the external alignment feature(s) 57 of the connector 40 and an external alignment feature of another connector (for example connector 1) are in an aligned orientation.

The locking fingers 54 may comprise a recess 61 on an outer surface of each finger 54. Such a recess 61 provided for receiving or engaging with an internal connection feature, such as a raised protrusion or tab such as a locking tab 14 of a connector such as that indicated as item 1. The recess 61 can be shaped for receipt of the internal connection feature (e.g. item 14) of another connector (e.g. the connector indicated as item 1 herein).

A tip 62 of the locking fingers may be of an at least partially chamfered configuration, preferentially to assist in the locking fingers 54 being able to be received into engagement by a connection feature such as that itemised as 14.

Various shapes of the alignment feature 57 as a cut out may be provided, for example: semi-circular, triangular, rectangular or other recti-linear or geometric shapes, elliptical, wedge shaped.

In various configurations, the outer wall 55 operates as a sleeve, for being brought into a sleeved connection with another connector (whether as a male or female connection). In one embodiment, the outer wall is configured for use as a 22 mm male taper connector to another connector comprising a female connection facility, and in another the outer wall is a sleeve, configured for use as a 22 female taper connector to another connector comprising a male connection facility.

The connectors or at least their body may be formed of any medically suitable materials, however particularly preferred is Polycarbonate (PC), Polyethylene (PE), Acrylonitrile Butadiene Styrene (ABS) or polypropylene (PP).

Figure 32:
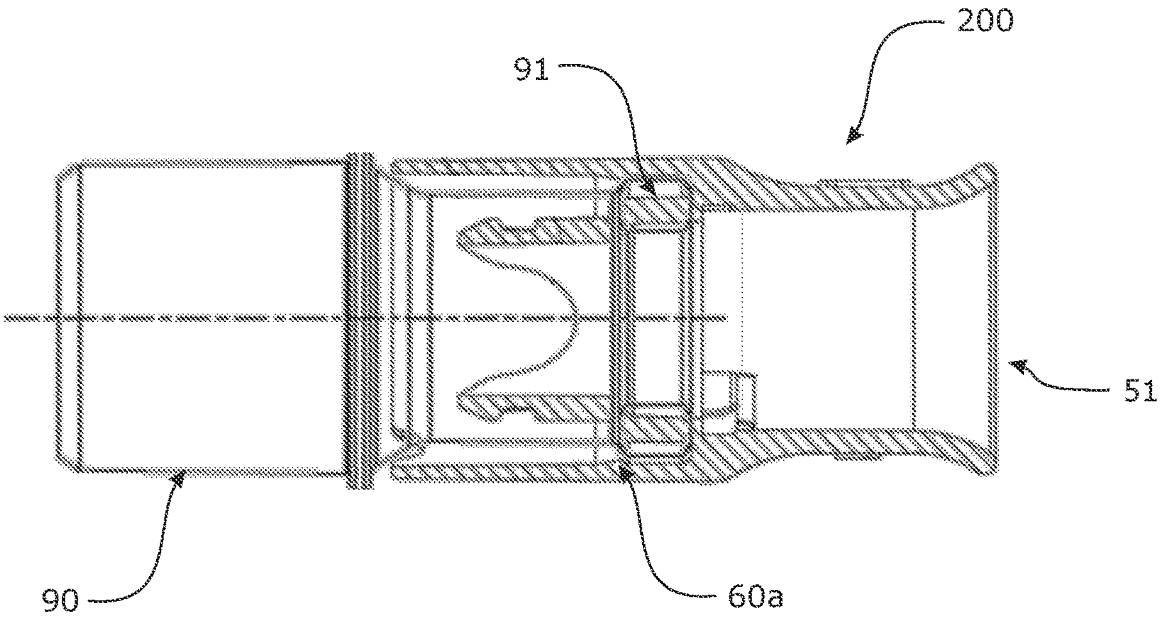
FIG. 32 shows a connection in particular by a flange or lip with a male connection feature of a connector as shown by FIGS. 28-29.

The internal surface of the second end 52 of the body may further comprise a protrusion for an engagement (e.g. an interference fit) with a commensurately shaped portion of another connector to be received by or within the internal surface bounded by the outer wall 55. For example, such a protrusion can extend as a shoulder 63 radially outwardly from the one or more locking fingers 54, or from a base 64 extending as a floor from the inner surface of the outer wall 55. The shoulder may also optionally also extending longitudinally in a direction toward an open end of the second end of the connector. Or, alternatively or in addition, an inner surface of the outer wall may comprise of a radially inwardly extending protrusion 60*a*. A space 59 is defined between a radially outward surface of the shoulder 63 and an inner surface of the outer wall or the inwardly extending protrusion 60*a*, such a space being sized and shaped so as to be receivable of a terminal end of another connector, such as a lip or flange part of another connector. The terminal end of the another connector can be received in the space as an interference fit between the outward surface of the shoulder and the inner surface of the outer wall or the protrusion 60*a*. For example see FIG. 32 shows an assembly of a lip or flange (or a shoulder) 91 of another connector 90 which can be brought into such an interference fit in the space 59 with a connector such as that itemised as connector 200. In this manner, the lip or flange 91 can be retained or held in place by the interference fit, and can also provide for a suitable pneumatic seal between each of these parts.

Alternatively or additionally, substantially adjacent to, or at least in part abutting the shoulder 63 and the inner surface of the outer wall, is a base 64, the base extending as a floor between an outward periphery of the shoulder and the inner surface of the wall. The base 64 may define a sealing surface upon which a terminal end or a face of a terminal end of another connector may become engaged therewith, optionally forming a pneumatic connection.

The connector 200 is configured to provide for a plurality of separate sealing surfaces upon which seals may be made, whether as a seal between component parts along the entirety of a surface or a point or particular location along that surface. As such, the connector 200 provides for six separate and different sealing surface options. Each of which are described below.

In a first sealing mode, the connector 200 may be configured to provide a first separate surface for sealing upon when a separate connection is made thereto by another connector (such as connector 1), the first surface defined by:

- a terminal face 58 of the second end 52 of the connector 200 when brought to bear upon a flange or lip 16 (or shoulder) that projects outwardly or away from an external surface of the body of another connector 1. For example, see FIG. 23 for such a sealed surface.

In a second sealing mode, the connector 200 may be configured to provide a second separate surface for sealing upon when a separate connection is made thereto by another connector (such as connector 90), the second surface defined by:

- an internal side wall surface 60 provided substantially at or toward a base end 64 of the second end of the connector 200, a part of another connector 90 (such as a lip or flange 91, optionally which may include a shoulder) being brought to bear substantially upon the internal side wall surface or a location along the internal side wall surface at or toward the base end. For example see item 180 in FIG. 29B.

In a third sealing mode, the connector 200 may be configured to provide a third separate surface for sealing upon when a separate connection is made thereto by another connector (such as connector 90), the third surface defined by:

- an internal side wall surface 60 of a protrusion 60A extending radially inwardly of the internal side wall surface 60 of the second end 52, a part of another connector 90 (such as a lip or flange 91, optionally which may include a shoulder) being brought to bear substantially upon the surface or a location along the surface of the protrusion 60A. For example, see item 140 of FIG. 29A.

In a fourth sealing mode, the connector 200 is configured to provide a fourth separate surface for sealing upon when a separate connection is made thereto by another connector (such as 90), the fourth surface defined by:

an internal side wall surface 60 of the second end 52 of the connector 200, where the internal side wall surface extends as a shoulder 63 radially outwardly from said one or more male connection features (such as the one or more locking fingers 54), a part of another connector 90 (such as a lip or flange 91, optionally which may include a shoulder) being brought to bear substantially upon a radially outward surface of the shoulder. For example, see item 170 of FIG. 29B.

In a fifth sealing mode, the connector 200 is configured to provide a fifth separate surface for sealing upon when a separate connection is made thereto by another connector (such as 90), the fifth surface defined by:

a radially outward surface of the one or more male connection features, in particular a radially outward surface of one or more locking fingers located within the second end 52 of the connector 200. For example, see item 160 of FIG. 29B.

In a sixth sealing mode, the connector 200 is configured to provide a sixth separate surface for sealing upon when a separate connection is made thereto by another connector (such as 90), the sixth surface defined by one or both of:

a lateral face or ledge of a shoulder extending radially outwardly from the one or more male connection features, in particular a radially outwardly extensive face or ledge extending radially outwardly from one or more locking fingers located within the second end 52 of the connector 200 (for example see item 150 FIG. 29A); or a lateral face or the base extending as a floor between an outward periphery of a shoulder extending radially outwardly from one or more male connection features, and the inner surface of the wall (for example see item 130 of FIG. 29A).

In still further configurations, optionally a cuff 65 may be provided about the first end 51 of the connector body 50, and may optionally at least partially overlap a portion of the second end 52 of the connector body. Such a cuff 65 may be typically an overmoulded material, overmoulded about the connector body 50, or the cuff may be a pre-formed component which is assembled into position. Alternatively, the cuff may be pre-formed, so that it can then be slipped over or placed onto the connector body into position.

The cuff 65 can be dimensioned to as to provide for a relatively smooth or uninterrupted outer surface contour with an exterior surface of the outer wall substantially abutting or substantially adjacent to an intersection 66 with the cuff.

The cuff may include an indicator of the connector to which it (i.e. the cuff) is in place therewith, or may provide an indication for a particular component or size of a component to be associated with the connector (optionally for example where the component is a patient interface, such as a nasal cannula or mask or other such interfaces). Such an indicator may be by way of colour.

The cuff 65 can be dimensioned to transition from a substantially circular exterior surface contour form, when substantially abutting or substantially adjacent to or with an exterior surface of the outer wall of the connector, to a substantially square exterior surface contour form provided substantially (optionally wholly) about the first end of the connector body. In this manner, a user may be able to apply more torque or force so as to disengage such a connector 40 from a connected engagement with another connector.

Figure 34A:
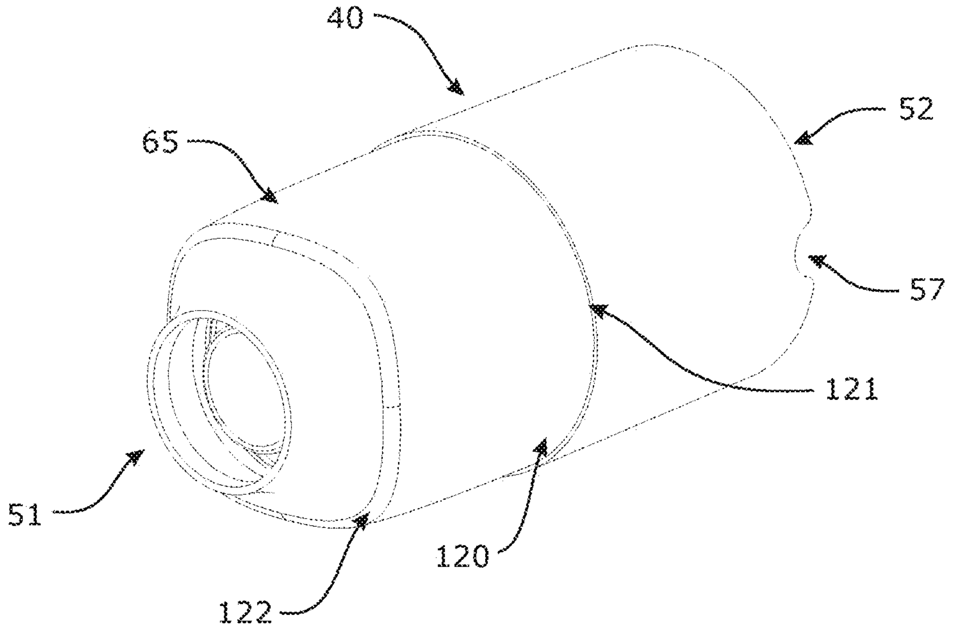
Figure 34B:
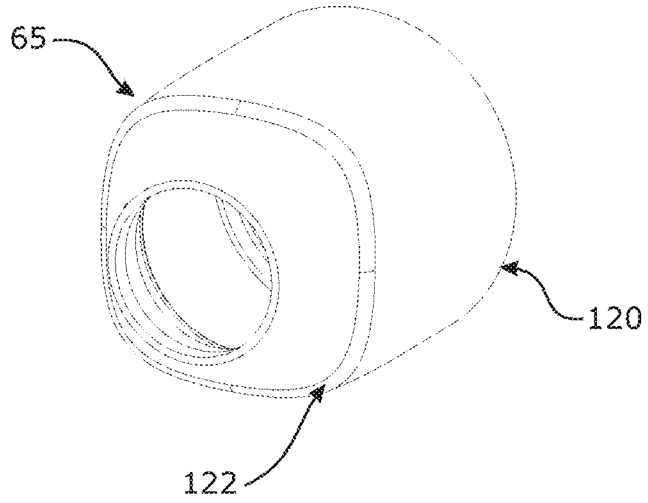
FIGS. 34B and 34C are different end perspective views of the cuff shown in FIG. 34A.
Figure 34C:
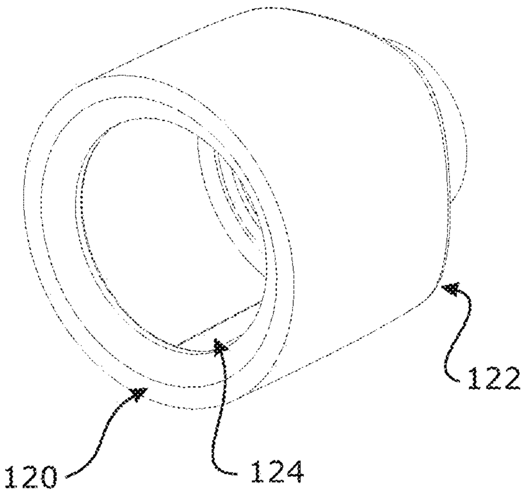

For example, as shown with particular reference to FIGS. 34A-C, it can be seen cuff 65 transitions from a substantially circular profile (indicated by item 120) in the region 121 where the cuff 65 intersects or is provided substantially adjacent with the body of the connector 40, to be a substantially more square or recti-linear shape in the region 122.

Figure 35:
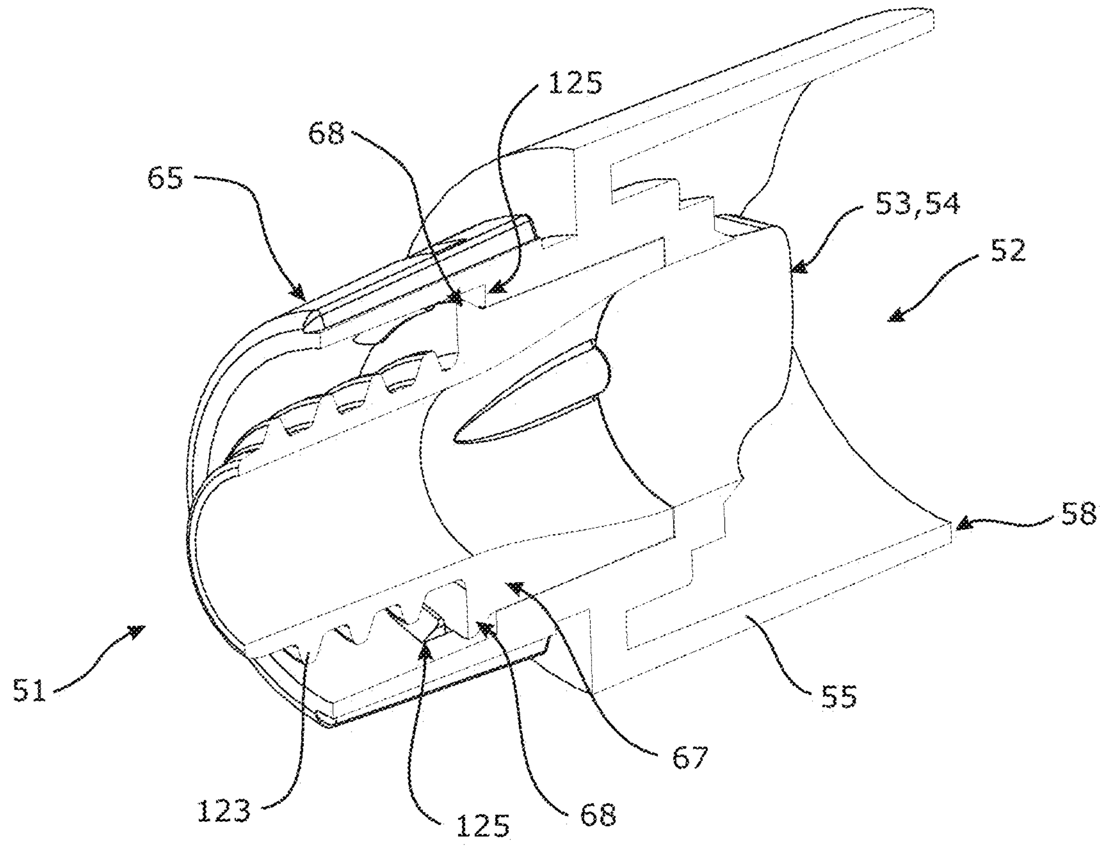
FIG. 35 is a cross-section through the centre or mid-line of the connector of FIG. 34A illustrating internal parts, including a swivel-type connector component.

FIGS. 30 and 35 additionally illustrate a swivel-type connector component 67 having a thread 123 for being threadably engaging of a terminal end of a conduit to be brought into engagement therewith, and so therefore into fluid communication with the lumen of the connector 40.

The cuff 65 may extend from substantially the second end 52 of the connector body 50 to overlap upon an exterior surface of a breathing tube or conduit to which said connector is to be, in use, engaged or be engageable, or said cuff extends to overlap upon at least a portion of a component to be associated with the terminal end of the breathing tube.

The outer surface of the cuff may be textured or otherwise surface treated to increase friction or grip to allow a user to apply a force or torque to the cuff (and in turn the connector).

Figure 33A:
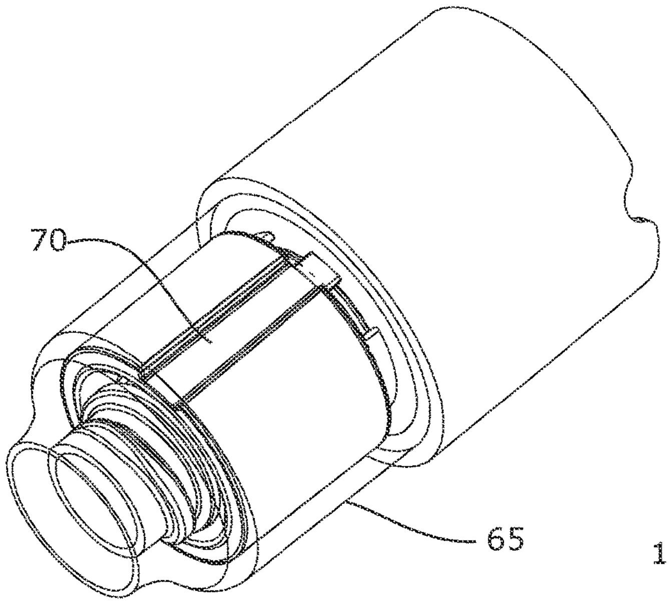
Figure 33B:
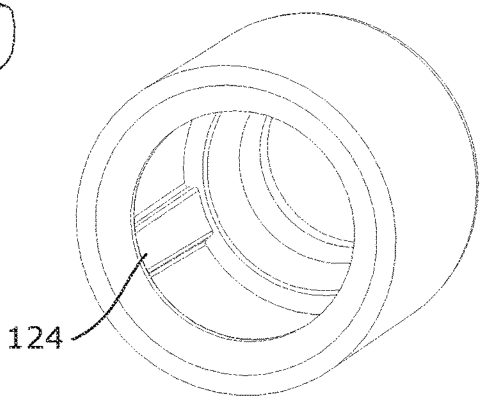
FIG. 33B shows the cuff which is to be placed upon the body.

The cuff may comprise of one or more splines 124 or other inwardly projecting portions on an inside surface for engagement or fitting into a suitably shaped recess or groove 70 on an outer surface of the body 50 to which the cuff is to be put into connection therewith. For example see FIG. 33A in which the cuff has been made partially see-through, and a groove 70 is then provided in an outer surface of the body 50 of the connector 40. In this way, the cuff 65 is more accurately located upon the body, yet also reduces the chances of the cuff inadvertently rotating about the body when a user applies a torque (e.g. when the user is trying to disconnection such a connector 40 from a connection with another connector, such as a connector 1). FIGS. 33B and 34C show the cuff 65 arrangement on its own and splines 124 or other projections are more evident.

It will be appreciated the cuff 65 may be an elastic or elasticised-type material, for example may be a silicone or a thermoplastic elastomer (TPE).

In various configurations, the cuff 65 may facilitate for at least in part a relief of strain otherwise imparted to an engagement or connection made between the breathing conduit and said first end or a component to be associated with the first end 51.

A further component (for example swivel-type connector component 67 as shown in FIG. 29) which may be associated with the connector 200, 40 is a swivel type arrangement. The purpose being to provide for a connection to the terminal end of a conduit, yet a swivel (or axially rotatable) type connection with the connector 200, 40 and the connector body 50.

As such, a swivel-type connector component 67 is, in use, connected with at least a part of the body 50 of a connector. The swivel-type connector 67 can be configured to connect with the terminal end of a conduit, and the swivel-type connector is configured to connect with the first end 51 of the connector.

The swivel-type connector component 67 can connect or engage with the terminal end of a conduit via a thread or threaded type engagement.

The swivel-type connector component 67 can connect to the body of the connector, such that relative movement of the connector body and swivel-type connector is allowed rotationally, yet prevented axially.

In various embodiments, the swivel-type connector component 67 can comprise a surface or surfaces 68 which forms a rotatable seal with the inner surface 69 of the connector body. For example, the inner surface 69 of the connector 40 may comprise of a pair of wall portions 125 which act to bound to locate the surface 68 within in a manner which allows for an axially located orientation of the swivel-type connector component 67 with the connector body, and which allows for the surface or surfaces 68 to rotate radially. In this way, a swivel type connection is made with the connector body.

Figure 35A:
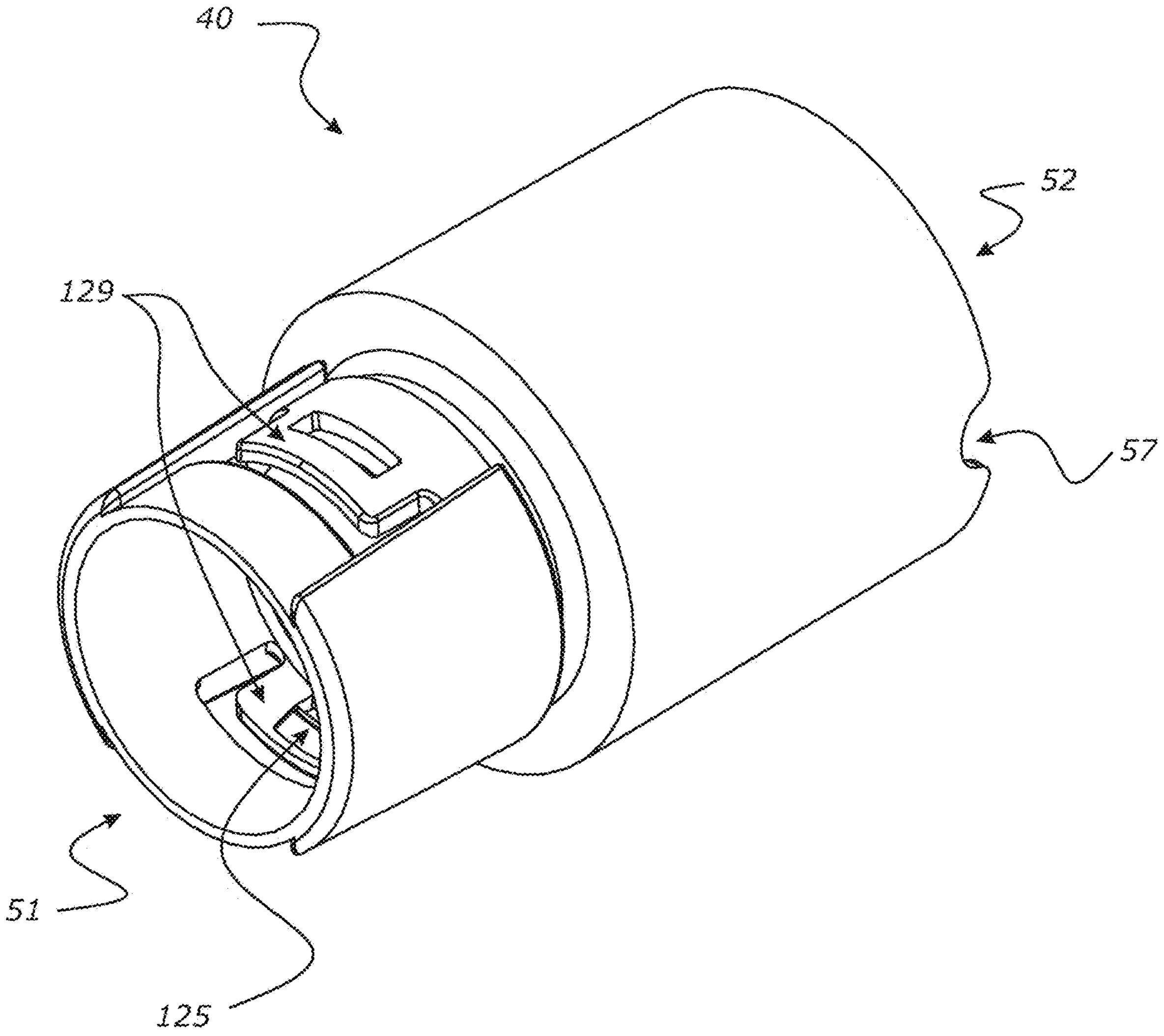
FIG. 35A is a perspective view of a connector.
Figure 35B:
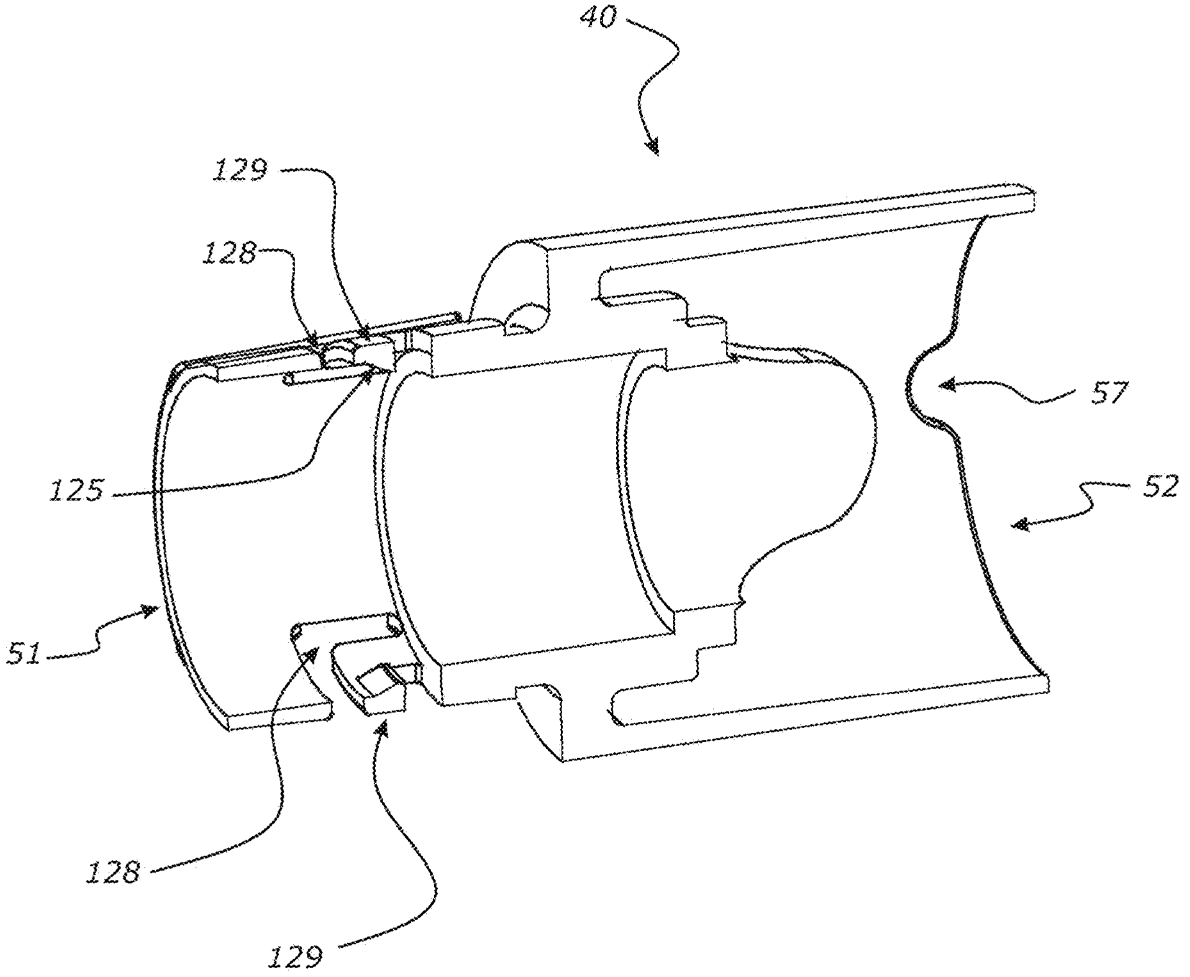
FIG. 35B is a cross-section of connector of FIG. 35A.

FIGS. 35A and 35B show a connector 40 where the body of the connector 40 comprises an attachment arm 129, for attachment of the swivel-type connector component 67 with the connector 40. The attachment arm 129 may comprise at least one wall portion or attachment barb or retaining protrusion 125, the protrusion 125 may engage with a corresponding lip or flange or at least part of the body of the swivel-type connector component 67, to retain the swivel-type connector component 67 in a axial direction while allowing rotation of the swivel-type connector component 67 relative to the connector body. The retaining protrusion 125 may include a ramped surface in a direction away from the first end 51 of the connector. The ramped surface may allow for insertion of the swivel-type connector component 67. The protrusion 125 may also comprise a substantially flat side optionally in a direction perpendicular to the body of the connector, configured prevent relative axial movement of the swivel-type connector component 67.

The attachment arm 129 may be cantilevered from part of the body so as to bend or flex relative the body. The cantilevered construction of the attachment arm 129 may allow for easier insertion of the swivel-type connector component 67, as the attachment arm 129 may flex outwardly to accommodate the insertion of a swivel-type connector component 67.

The attachment arm 129 may be surrounded by a cut-out region 128, the cut out region allowing the attachment arm to flex relative to the connector body. The cut-out region 128 may be arranged around the attachment arm 129 to promote flexibility in at least a radially outward direction from the connector 40.

The attachment arm 129 may comprise a recess configured to receive part of the swivel-type connector component 67 (for example surface 68.)

The foregoing description of the invention includes preferred forms thereof. Modifications may be made thereto without departing from the scope of the invention.

The invention claimed is:

1. A connector to be provided at a terminal end of a breathing conduit, the connector comprising a body, the body comprising a first end and a second end, the body defining a lumen that extends between the first end of the body and the second end of the body, the first end of the body being configured to engage with the terminal end of the breathing conduit or at least a component to be associated with the terminal end of the breathing conduit;

the second end of the body being configured to engage with a second connector, in use, an internal portion of the second end of the body comprising two or more locking fingers, the two or more locking fingers being configured to connect with a female end of the second connector or a female part of the second connector, the female end or the female part being configured to receive the two or more locking fingers, the two or more locking fingers each comprising an outer surface and an inner surface opposite the outer surface, the inner surface defining at least a portion of the lumen, the outer surface of each of the two or more locking fingers comprising a recess engageable with a complementary portion of the second connector;

the body further comprising an outer wall surrounding the two or more locking fingers, the outer wall being configured to operate as a sleeve that, in use, is configured to be brought into a sleeved connection with the second connector, and the outer wall comprising an exterior surface and an interior surface, the interior surface of the outer wall being radially spaced apart from yet overlying the two or more locking fingers such that a gap is defined between the interior surface of the outer wall and the two or more locking fingers; and wherein the recess of the two or more locking fingers and the complementary portion of the second connector forms a catch or a latch, and wherein the two or more locking fingers of the connector and the complementary portion of the second connector prevent rotational movement when engaged.

2. The connector according to claim 1, wherein the outer wall comprises one or more external alignment features configured to align the body and the second connector into an externally aligned connection therebetween.

3. The connector according to claim 2, wherein the two or more locking fingers are oriented so as to be radially aligned with the one or more external alignment features.

4. The connector according to claim 2, wherein the one or more external alignment features comprise one or more cut-outs positioned on at least one of a terminal end or a face of the outer wall.

5. The connector according to claim 4, wherein the one or more cut-outs are configured to be received by a substantially reciprocally shaped portion of the second connector to which said outer wall is to be placed in contact, in use.

6. The connector according to claim 2, wherein the one or more external alignment features are arranged at least one of evenly and equidistantly about a circumference of a terminal end face of the outer wall at the second end.

7. The connector according to claim 2, wherein the one or more external alignment features are configured to be co-locatable for keying with a reciprocally shaped projection of a portion of the second connector when brought to bear into connection, in use, during a connection between a terminal face of the second end of the connector and the second connector.

8. The connector according to claim 2, wherein the one or more external alignment features are at least one of:

configured to prevent connection of the two or more locking fingers of the connector with the second connector when the one or more external alignment features of the connector and an external alignment feature of the second connector are in an unaligned orientation; and configured to allow connection of the two or more locking fingers of the connector with the second connector when the one or more external alignment features of the connector and the external alignment feature of the second connector are in aligned orientation.

9. The connector according to claim 2, wherein the one or more external alignment features comprise one or more of the following shapes: semi-circular, triangular, rectangular, other recti-linear, geometric shapes, elliptical and wedge-shaped.

10. The connector according to claim 1, wherein the outer wall comprises a male connection facility.

11. The connector according to claim 1, wherein a diameter of the outer wall at the second end is smallest at a terminal end of the second end, with the diameter of the outer wall increasing in a direction extending away from the terminal end of the second end towards the first end.

12. The connector according to claim 1, wherein the two or more locking fingers are housed substantially within the second end.

13. The connector according to claim 1, wherein a space is defined between an outer surface of the two or more locking fingers and an inner surface of the outer wall.

14. The connector according to claim 1, wherein each of the two or more locking fingers comprises an outer surface having a recess.

15. The connector according to claim 14, wherein the recess is configured to receive or engage with a raised protrusion or tab of the second connector.

16. The connector according to claim 1, wherein the connector is configured as an adapter to facilitate connection between two connectors.

17. The connector according to claim 1, wherein the two or more locking fingers comprise a length greater than a width.

18. The connector according to claim 1, wherein the two or more locking fingers extend in a direction of fluid flow.

19. The connector of claim 1, wherein the gap defined between the interior surface of the outer wall and the two or more locking fingers is configured to receive a portion of the second connector.

20. The connector of claim 1, wherein the wherein the two or more locking fingers of the connector and the complementary portion of the second connector are configured to prevent clockwise and counter-clockwise rotational movement when engaged.

21. The connector as claimed in claim 1, wherein the lumen is sized to pass gas therethrough for providing respiratory therapy to a user.

22. The connector as claimed in claim 1, wherein the catch or a latch is configured to provide quick-connect and quick-release connection with the second connection device.

23. A connector to be provided at a terminal end of a breathing conduit, the connector comprising a body, the body comprising a first end and a second end, the body defining a lumen that extends between the first end of the body and the second end of the body;

the second end configured to be engaged with an inspiratory conduit connector provided at an end of an inspiratory conduit;

the body comprising an internal portion, the internal portion including two or more locking fingers being configured to connect with a female part of the inspiratory conduit connector, the two or more locking fingers each comprising an outer surface and an inner surface opposite the outer surface, the inner surface defining at least a portion of the lumen, the outer surface of each of the two or more locking fingers comprising a recess engageable with a complementary portion of the inspiratory conduit connector; and the body comprising an outer wall radially spaced apart from and overlying the two or more locking fingers such that a gap is defined between the outer wall and the two or more locking fingers;

the outer wall operating as a sleeve that, in use, is brought into a sleeved connection with the inspiratory conduit connector; and wherein the recess of the two or more locking fingers and the complementary portion of the inspiratory conduit connector forms a catch or a latch and wherein the two or more locking fingers of the connector and the complementary portion of the second connector prevent rotational movement when engaged.

24. The connector according to claim 23 additionally comprising a patient interface comprising a non-sealing nasal cannula connected with the first end.

25. A respiratory system comprising:

a flow generator;

a humidifier;

an inspiratory conduit having an inspiratory conduit connector at one end with a female part;

a patient interface; and a connector configured to connect the inspiratory conduit with the patient interface, the connector comprising:

a body comprising a first end, a second end, and a lumen defined within the body, the lumen extending between the first end and the second end and the lumen configured to pass gas therethrough;

the first end being configured to be engageable with the patient interface;

the second end being configured to be engageable with the inspiratory conduit connector;

the body comprising an internal portion, the internal portion comprising two or more locking fingers being configured to connect with the female part of the inspiratory conduit connector, the female part being configured to receive said two or more locking fingers, the two or more locking fingers each comprising an outer surface and an inner surface opposite the outer surface, the inner surface defining at least a portion of the lumen, the outer surface of each of the two or more locking fingers comprising a recess engageable with a complementary portion of the inspiratory conduit connector;

the body also comprising an outer wall surrounding an entire length of the two or more locking fingers, the outer wall being configured to operate as a sleeve that, in use, is configured to be brought into a sleeved connection with the inspiratory conduit connector, and the outer wall comprising an exterior surface and an interior surface, the interior surface being radially spaced apart from yet overlying the two or more locking fingers such that a gap is defined between the interior surface of the outer wall and the two or more locking fingers; and wherein the recess of the two or more locking fingers and the complementary portion of the inspiratory conduit connector forms a catch or a latch, and wherein the two or more locking fingers of the connector and the complementary portion of the second connector prevent rotational movement in either direction when engaged.

26. The connector according to claim 23, wherein the two or more locking fingers comprise a length greater than a width.

27. The connector according to claim 23, wherein the two or more locking fingers extend in a direction of fluid flow.

28. The connector of claim 23, wherein the gap defined between the outer wall and the two or more locking fingers is configured to receive a portion of the inspiratory conduit connector.

29. The connector as claimed in claim 23, wherein the lumen is sized to pass gas therethrough for providing respiratory therapy to a user.

30. The connector as claimed in claim 23, wherein the catch or a latch is configured to provide quick-connect and quick-release connection with the female part of the inspiratory conduit connector.

31. The respiratory system according to claim 25, wherein patient interface comprises a non-sealing nasal cannula.

32. The respiratory system of claim 31, wherein the gap defined between the interior surface of the outer wall and the two or more locking fingers receives a portion of the inspiratory conduit connector.

33. The respiratory system of claim 31, wherein the recess of the two or more locking fingers is open on the outer surface of the two or more locking fingers.

34. The respiratory system as claimed in claim 31, wherein the lumen is sized to pass gas therethrough for providing respiratory therapy to a user.

35. The respiratory system as claimed in claim 25, wherein the catch or a latch is configured to provide quick-connect and quick-release connection with the female part of the inspiratory conduit connector.

* * * * *